United States Patent
Inoue et al.

(10) Patent No.: US 9,929,352 B2
(45) Date of Patent: Mar. 27, 2018

(54) ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Yui Yamada, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 112 days.

(21) Appl. No.: 14/976,443

(22) Filed: Dec. 21, 2015

(65) Prior Publication Data

US 2016/0190471 A1 Jun. 30, 2016

(30) Foreign Application Priority Data

Dec. 26, 2014 (JP) ................. 2014-265483

(51) Int. Cl.
*H01L 51/00* (2006.01)
*C07D 401/14* (2006.01)
*C09K 11/06* (2006.01)

(52) U.S. Cl.
CPC ........ *H01L 51/0067* (2013.01); *C07D 401/14* (2013.01); *C09K 11/06* (2013.01); *H01L 51/0058* (2013.01); *H01L 51/006* (2013.01); *H01L 51/0054* (2013.01)

(58) Field of Classification Search
CPC ....... C09K 11/06; H01L 51/00; H01L 51/006; H01L 51/0067; H01L 51/0051; H01L 51/0054; H01L 51/0058; C07D 401/14
USPC ............................ 257/40; 544/296; 428/690
See application file for complete search history.

(56) References Cited

U.S. PATENT DOCUMENTS

| | | |
|---|---|---|
| 8,771,840 B2 | 7/2014 | Suzuki et al. |
| 9,059,411 B2 | 6/2015 | Suzuki et al. |
| 2007/0224447 A1 | 9/2007 | Sotoyama et al. |
| 2007/0247063 A1 | 10/2007 | Murase et al. |
| 2010/0069647 A1 | 3/2010 | Suzuki et al. |
| 2010/0301318 A1 | 12/2010 | Kuma et al. |
| 2011/0233604 A1 | 9/2011 | Ikeda |

(Continued)

FOREIGN PATENT DOCUMENTS

JP 2009-184987 A 8/2009
KR 20120117693 A * 10/2012

*Primary Examiner* — Amanda C Walke
(74) *Attorney, Agent, or Firm* — Husch Blackwell LLP

(57) ABSTRACT

An object is to provide an organic compound having high heat resistance and a light-emitting element, a light-emitting device, an electronic device, and a display device each having high reliability. Provided are an organic compound having a 2,2'-(pyridine-2,6-diyl)bipyrimidine skeleton in which the 2-positions of pyrimidine skeletons are bonded to the 2- and 6-positions of a pyridine skeleton, and having a structure in which at least one aryl group having a fused structure with 10 to 16 carbon atoms is bonded to the 2,2'-(pyridine-2,6-diyl)bipyrimidine skeleton, and a light-emitting element, a light-emitting device, an electronic device, and a display device each containing the organic compound.

17 Claims, 19 Drawing Sheets

(56) References Cited

U.S. PATENT DOCUMENTS

| | | |
|---|---|---|
| 2012/0098417 A1 | 4/2012 | Inoue et al. |
| 2012/0126205 A1 | 5/2012 | Kawamura et al. |
| 2012/0126208 A1 | 5/2012 | Kawamura et al. |
| 2012/0126209 A1 | 5/2012 | Kawamura et al. |
| 2012/0153268 A1 | 6/2012 | Kawamura et al. |
| 2012/0264936 A1 | 10/2012 | Inoue et al. |
| 2012/0274201 A1 | 11/2012 | Seo et al. |
| 2013/0048964 A1 | 2/2013 | Takeda et al. |
| 2013/0088144 A1 | 4/2013 | Inoue et al. |
| 2013/0165653 A1 | 6/2013 | Inoue et al. |
| 2013/0281693 A1 | 10/2013 | Inoue et al. |
| 2013/0324721 A1 | 12/2013 | Inoue et al. |
| 2014/0034924 A1 | 2/2014 | Kawata et al. |
| 2014/0034931 A1 | 2/2014 | Inoue et al. |
| 2014/0291645 A1 | 10/2014 | Inoue et al. |
| 2014/0296538 A1 | 10/2014 | Suzuki et al. |
| 2014/0339522 A1 | 11/2014 | Nonaka et al. |
| 2014/0339524 A1 | 11/2014 | Shitagaki et al. |
| 2014/0339526 A1 | 11/2014 | Inoue et al. |
| 2015/0005496 A1 | 1/2015 | Inoue et al. |
| 2015/0073142 A1 | 3/2015 | Ohsawa et al. |
| 2015/0073144 A1 | 3/2015 | Inoue et al. |
| 2015/0108462 A1 | 4/2015 | Inoue et al. |
| 2015/0131302 A1 | 5/2015 | Inoue et al. |
| 2015/0340622 A1 | 11/2015 | Inoue et al. |
| 2015/0349278 A1 | 12/2015 | Inoue et al. |
| 2016/0013421 A1 | 1/2016 | Inoue et al. |
| 2016/0093817 A1 | 3/2016 | Inoue et al. |
| 2016/0093818 A1 | 3/2016 | Inoue et al. |
| 2016/0126463 A1* | 5/2016 | Kadoma ............ H01L 51/0054 257/40 |
| 2016/0343955 A1 | 11/2016 | Inoue et al. |
| 2017/0062735 A1* | 3/2017 | Takeda ................ H01L 51/0072 |

* cited by examiner

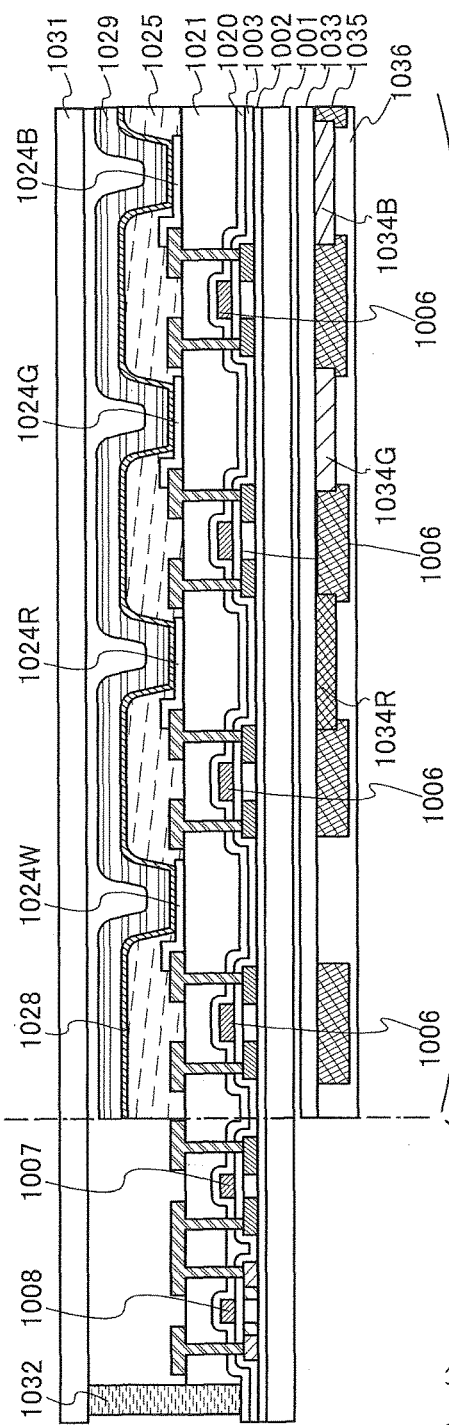
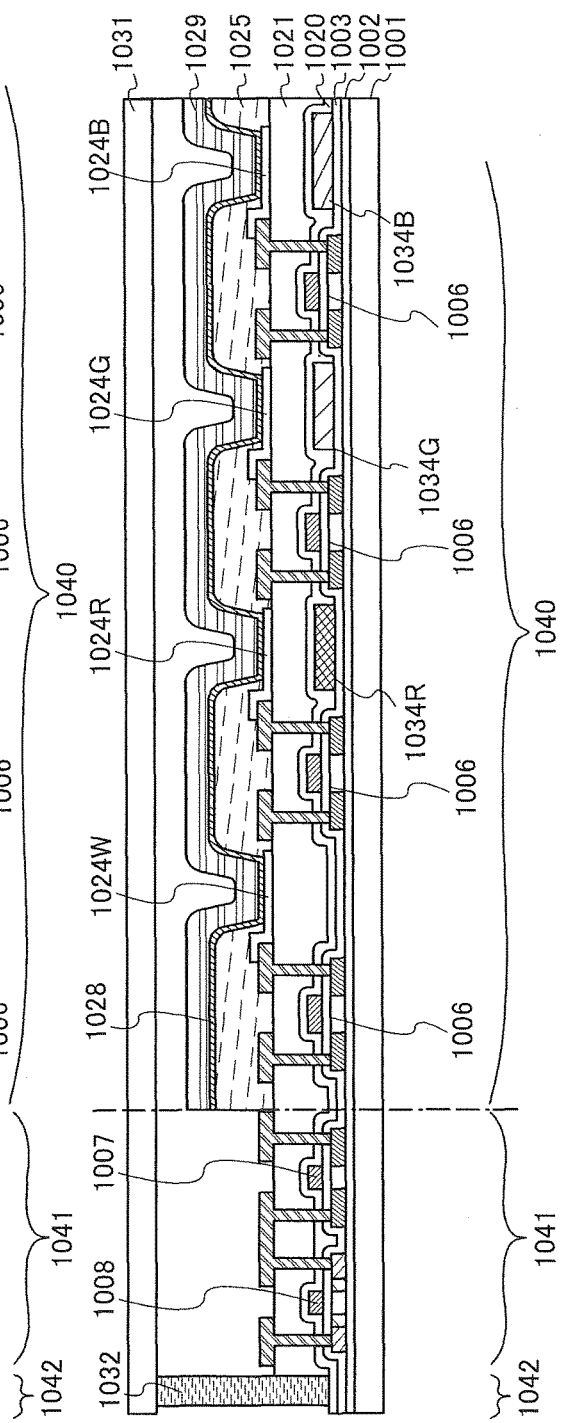
FIG. 3A
FIG. 3B

ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

BACKGROUND OF THE INVENTION

1. Field of the Invention

One embodiment of the present invention relates to an organic compound and a light-emitting element, a display module, a lighting module, a display device, a light-emitting device, an electronic device, and a lighting device in which the organic compound is used. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, an imaging device, a method for driving any of them, and a method for manufacturing any of them.

2. Description of the Related Art

Light-emitting elements (organic EL elements) including organic compounds and utilizing electroluminescence (EL) have been put to more practical use. In the basic structure of such a light-emitting element, an organic compound layer containing a light-emitting substance (an EL layer) is provided between a pair of electrodes. By voltage application to this element, light emission from the light-emitting substance can be obtained.

Since such light-emitting elements are of self-light-emitting type, light-emitting elements have advantages over liquid crystal displays when used as pixels of a display in that visibility of pixels is high and backlight is not required. Thus, light-emitting elements are suitable as flat panel display elements. A display including such a light-emitting element is also highly advantageous in that it can be thin and lightweight. Besides, very high speed response is one of the features of such an element.

Since light-emitting layers of such light-emitting elements can be successively formed two-dimensionally, planar light emission can be achieved. This feature is difficult to realize with point light sources typified by incandescent lamps and LEDs or linear light sources typified by fluorescent lamps. Thus, light-emitting elements also have great potential as planar light sources, which can be applied to lighting devices and the like.

Although displays or lighting devices including light-emitting elements can be suitably used for a variety of electronic devices as described above, their performance and cost competitiveness have plenty of room to improve. In order to achieve this, materials that have good characteristics and are easily handled are required. There are particularly great demands on heat resistance and reliability such as a lifetime.

Patent Document 1 discloses a pyrimidine- or triazine-based derivative, an electron-transport material containing the same, and an organic electroluminescent element containing the same.

REFERENCE

[Patent Document 1] Japanese Published Patent Application No. 2009-184987

SUMMARY OF THE INVENTION

An object of one embodiment of the present invention is to provide a novel organic compound. An object of another embodiment of the present invention is to provide a novel organic compound that can be used as an electron-transport material of a light-emitting element. An object of another embodiment of the present invention is to provide an organic compound that can be used as an electron-injection material of a light-emitting element. An object of another embodiment of the present invention is to provide an organic compound that can be used as an electron-injection material of a light-emitting element and that has high heat resistance. An object of another embodiment of the present invention is to provide an organic compound with which a light-emitting element having high reliability can be manufactured. An object of another embodiment of the present invention is to provide an organic compound with which a display device having less crosstalk can be obtained.

An object of another embodiment of the present invention is to provide a light-emitting device, a display device, and an electronic device each having less crosstalk.

An object of another embodiment of the present invention is to provide a light-emitting element, a display module, a lighting module, a light-emitting device, a display device, and an electronic device each having high reliability. An object of another embodiment of the present invention is to provide a light-emitting element, a display module, a lighting module, a light-emitting device, a display device, and an electronic device each having high display quality.

It is only necessary that at least one of the above-described objects be achieved in the present invention.

One embodiment of the present invention is an organic compound represented by the following general formula (G1).

[Chemical Formula 1]

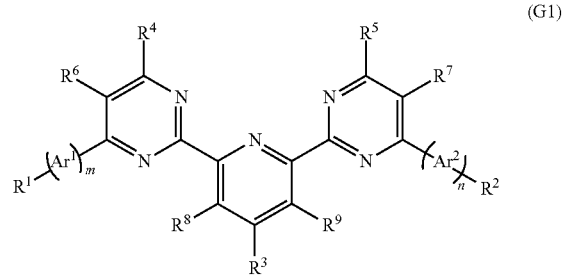

(G1)

In the general formula (G1), $Ar^1$ and $Ar^2$ represent a phenylene group, and n and m separately represent 0 or 1. $R^1$ to $R^3$ separately represent hydrogen or an aryl group having 6 to 16 carbon atoms, and at least one of $R^1$ to $R^3$ is an aryl group with a fused structure. $R^4$ to $R^9$ separately represent hydrogen, an alkyl group having 1 to 6 carbon atoms, or an aryl group having 6 to 10 carbon atoms.

Another embodiment of the present invention is an organic compound represented by the following general formula (G2).

[Chemical Formula 2]

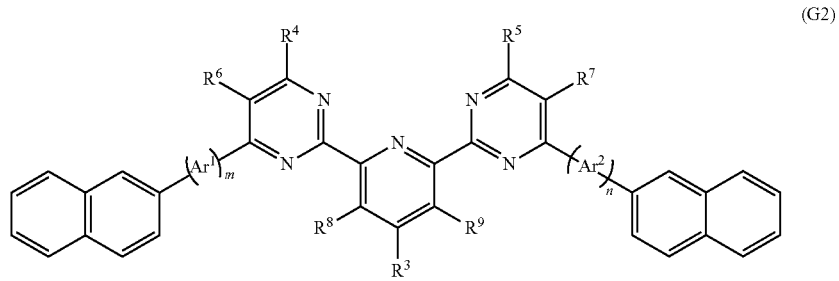

(G2)

In the general formula (G2), $Ar^1$ and $Ar^2$ represent a phenylene group, and n and m separately represent 0 or 1. $R^3$ to $R^9$ separately represent hydrogen, an alkyl group having 1 to 6 carbon atoms, or an aryl group having 6 to 10 carbon atoms.

Another embodiment of the present invention is any of the above-described organic compounds in which $R^3$ is hydrogen.

Another embodiment of the present invention is any of the above-described organic compounds in which m and n are 0.

Another embodiment of the present invention is any of the above-described organic compounds in which m and n are 1.

Another embodiment of the present invention is an organic compound represented by the following general formula (G3).

[Chemical Formula 3]

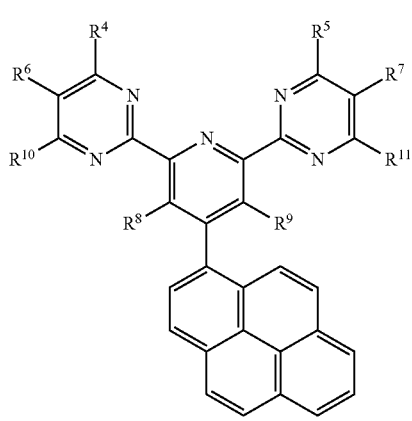

(G3)

In the general formula (G3), $R^4$ to $R^{11}$ separately represent hydrogen, an alkyl group having 1 to 6 carbon atoms, or an aryl group having 6 to 10 carbon atoms.

Another embodiment of the present invention is any of the above-described organic compounds in which $R^{10}$ and $R^{11}$ are each a phenyl group.

Another embodiment of the present invention is any of the above-described organic compounds in which $R^4$ and $R^5$ are each a phenyl group.

Another embodiment of the present invention is any of the above-described organic compounds in which $R^6$ to $R^9$ are each hydrogen.

Another embodiment of the present invention is an organic compound represented by the following structural formula (100).

[Chemical Formula 4]

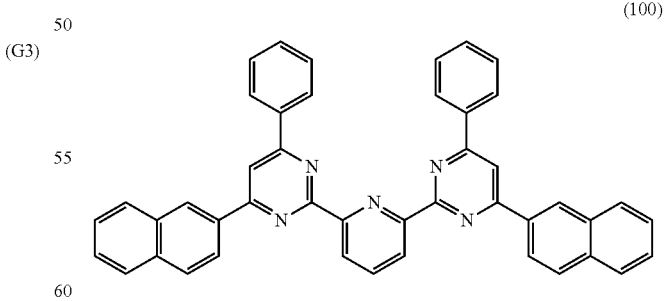

(100)

Another embodiment of the present invention is an organic compound represented by the following structural formula (200).

[Chemical Formula 5]

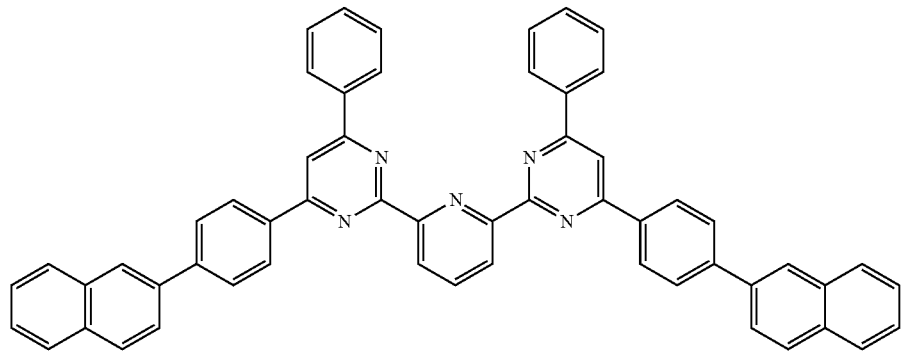

(200)

Another embodiment of the present invention is an organic compound represented by the following structural formula (300).

[Chemical Formula 6]

(300)

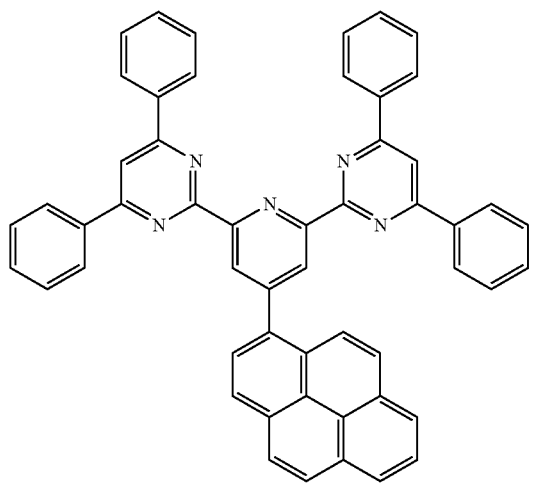

Another embodiment of the present invention is a light-emitting element that contains any of the above-described organic compounds.

Another embodiment of the present invention is a light-emitting element that contains any of the above-described organic compounds in an electron-transport layer.

Another embodiment of the present invention is a light-emitting element that contains any of the above-described organic compounds in an electron-injection layer.

Another embodiment of the present invention is a tandem light-emitting element that contains any of the above-described organic compounds.

Another embodiment of the present invention is a light-emitting element that contains any of the above-described organic compounds in a charge-generation layer.

Another embodiment of the present invention is a light-emitting element including an EL layer between a pair of electrodes. The EL layer includes a layer containing at least an alkali metal or an alkaline earth metal and a layer containing any of the above-described organic compounds in contact with the layer containing an alkali metal or an alkaline earth metal.

Another embodiment of the present invention is a light-emitting element including an EL layer between a pair of electrodes. The EL layer includes a layer containing at least an alkali metal or an alkaline earth metal and any of the above-described organic compounds.

Another embodiment of the present invention is either of the above-described light-emitting elements in which the alkali metal or the alkaline earth metal is lithium.

Another embodiment of the present invention is a display module including any of the above-described light-emitting elements.

Another embodiment of the present invention is a lighting module including any of the above-described light-emitting elements.

Another embodiment of the present invention is a light-emitting device including any of the above-described light-emitting elements and a unit for controlling the light-emitting element.

Another embodiment of the present invention is a display device including any of the above-described light-emitting elements in a display portion and a unit for controlling the light-emitting element.

Another embodiment of the present invention is a lighting device including any of the above-described light-emitting elements in a lighting portion and a unit for controlling the light-emitting element.

Another embodiment of the present invention is an electronic device including any of the above-described light-emitting elements.

Note that the light-emitting device in this specification includes, in its category, an image display device with a light-emitting element. The light-emitting device may be included in a module in which a light-emitting element is provided with a connector such as an anisotropic conductive film or a tape carrier package (TCP), a module in which a printed wiring board is provided at the end of a TCP, or a module in which an integrated circuit (IC) is directly mounted on a light-emitting element by a chip on glass (COG) method. The light-emitting device may be included in lighting equipment or the like.

One embodiment of the present invention is a novel organic compound. Another embodiment of the present invention is a novel organic compound that can be used as an electron-transport material of a light-emitting element.

Another embodiment of the present invention is an organic compound that can be used as an electron-injection material of a light-emitting element. Another embodiment of the present invention is an organic compound that can be used as an electron-injection material of a light-emitting element and that has high heat resistance. Another embodiment of the present invention is an organic compound with which a light-emitting element having high reliability can be manufactured. Another embodiment of the present invention is an organic compound with which a display device having less crosstalk can be provided.

Another embodiment of the present invention can provide a light-emitting device, a display device, and an electronic device each having less crosstalk.

Another embodiment of the present invention can provide a light-emitting element, a light-emitting device, a display device, and an electronic device each having high reliability. Another embodiment of the present invention can provide a light-emitting device, a display device, and an electronic device each having high display quality. Another embodiment of the present invention can provide a novel organic compound, a novel light-emitting element, a novel display module, a novel lighting module, a novel light-emitting device, a novel display device, a novel electronic device, and a novel lighting device.

Note that the descriptions of these effects do not disturb the existence of other effects. One embodiment of the present invention does not necessarily achieve all the above effects. Other effects will be apparent from and can be derived from the descriptions of the specification, the drawings, the claims, and the like.

BRIEF DESCRIPTION OF THE DRAWINGS

FIGS. 3A and 3B are schematic diagrams of an active matrix light-emitting device.

FIGS. 7A, 7B1, 7B2, 7C, and 7D illustrate electronic devices.

DETAILED DESCRIPTION OF THE INVENTION

Figure 1A:
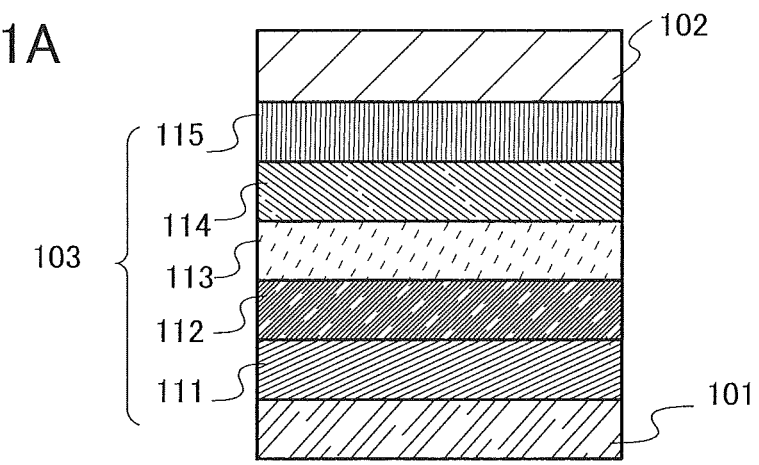
FIGS. 1A to 1C are schematic diagrams of light-emitting elements.

Embodiments of the present invention will be described below with reference to the drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments.

An organic compound of one embodiment of the present invention has a 2,2'-(pyridine-2,6-diyl)bipyrimidine skeleton in which the 2-positions of pyrimidine skeletons are bonded to the 2- and 6-positions of a pyridine skeleton. In the organic compound of one embodiment of the present invention, at least one aryl group having a fused structure with 10 to 16 carbon atoms is bonded to the 2,2'-(pyridine-2,6-diyl)bipyrimidine skeleton. Note that the aryl group having the fused structure may be bonded via a phenylene group.

The organic compound having the above-described structure has a favorable electron-transport property and therefore can be suitably used as an electron-transport layer, an electron-injection layer, and a host material in a light-emitting element. The organic compound has high heat resistance, with which a light-emitting element having high reliability can be provided.

It is particularly preferable that the organic compound having the above-described structure in one embodiment of the present invention be used for a layer in contact with the anode side of a charge-generation layer in a tandem light-emitting element or the like. In that case, a luminance decrease due to accumulation of driving time of the light-emitting element can be suppressed, and thus, the reliability of the light-emitting element can be improved. In addition, crosstalk can be suppressed, and this makes it easy to provide a display device having high display quality. The charge-generation layer will be described in detail in a later description of light-emitting elements.

The organic compound in which at least one aryl group having a fused structure with 10 to 16 carbon atoms is bonded to the 2,2'-(pyridine-2,6-diyl)bipyrimidine skeleton can be represented by the following general formula (G1).

[Chemical Formula 7]

(G1)

[Structural formula showing a pyridine ring in the center connected to two pyrimidine rings on either side, with substituents $R^1$ through $R^9$, $Ar^1$, $Ar^2$, and indices $m$ and $n$.]

In the general formula (G1), $Ar^1$ and $Ar^2$ represent a phenylene group, and n and m separately represent 0 or 1. $R^1$ to $R^3$ separately represent hydrogen or an aryl group having 6 to 16 carbon atoms, and at least one of $R^1$ to $R^3$ is an aryl group having a fused structure with 10 to 16 carbon atoms. $R^4$ to $R^9$ separately represent hydrogen, an alkyl group having 1 to 6 carbon atoms, or an aryl group having 6 to 10 carbon atoms.

The organic compound represented by the general formula (G1) preferably has a structure in which $R^1$ and $R^2$ are each a naphthyl group, in which case the heat resistance is increased. That is, an organic compound represented by the following general formula (G2) is preferable.

[Chemical Formula 8]

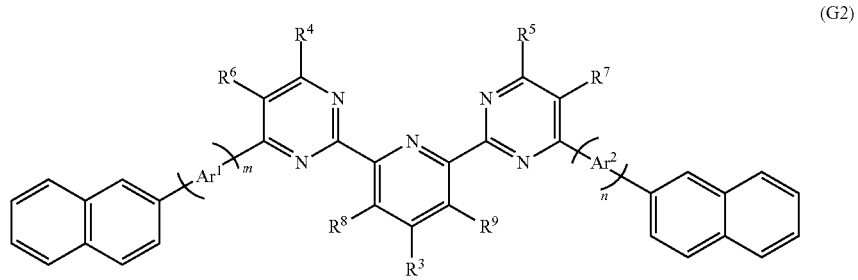

(G2)

In the general formula (G2), $Ar^1$ and $Ar^2$ represent a phenylene group, and n and m separately represent 0 or 1. $R^3$ to $R^9$ separately represent hydrogen, an alkyl group having 1 to 6 carbon atoms, or an aryl group having 6 to 10 carbon atoms.

In the organic compound represented by the general formula (G2), it is preferable that $R^3$ be hydrogen. It is also preferable that $R^6$ and $R^7$ be each hydrogen.

Note that in the general formula (G2), it is preferable that $R^4$ and $R^5$ be each a phenyl group.

Although the organic compound represented by the general formula (G2) exhibits favorable characteristics regardless of whether m and n are 0 or 1, a light-emitting element having a particularly long lifetime can be obtained when m and n are 1 and the organic compound is used in an electron-transport layer which is provided in contact with a charge-generation layer or an intermediate layer.

In the organic compound represented by the general formula (G1), $R^3$ is preferably a pyrenyl group, in which case the heat resistance is increased. That is, one embodiment of the present invention is an organic compound represented by the following general formula (G3).

[Chemical Formula 9]

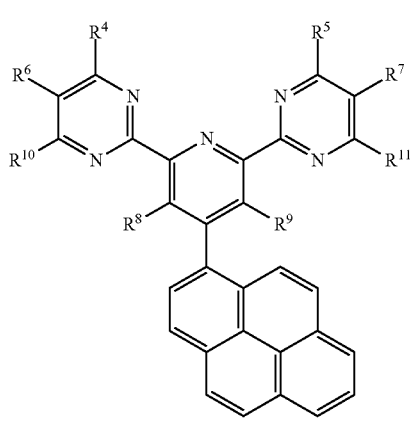

(G3)

In the general formula (G3), $R^4$ to $R^{11}$ separately represent hydrogen, an alkyl group having 1 to 6 carbon atoms, or an aryl group having 6 to 10 carbon atoms.

In the organic compound represented by the general formula (G3), it is preferable that $R^4$, $R^5$, $R^{10}$, and $R^{11}$ be each a phenyl group, in which case the chemical stability of the compound can be maintained and an appropriate LUMO level for charge injection can be obtained.

In the organic compound represented by the general formula (G3), it is preferable that $R^6$, $R^7$, $R^8$, and $R^9$ be each hydrogen, in which case the steric structure of the compound is not easily twisted and a favorable charge-transport property can be obtained.

Note that when the organic compound represented by the general formula (G3) is used for a layer in contact with the anode side of a charge-generation layer, a display device in which crosstalk is particularly effectively suppressed and which has high display quality can be obtained.

Specific examples of the alkyl group having 1 to 6 carbon atoms include a methyl group, an ethyl group, an n-propyl group, an iso-propyl group, an n-butyl group, an iso-butyl group, a sec-butyl group, a tert-butyl group, a pentyl group, a hexyl group, and a cyclohexyl group.

Specific examples of the aryl group having 6 to 16 carbon atoms include a phenyl group, a biphenyl group, a naphthyl group, a fluorenyl group, a phenathrenyl group, a triphenylenyl group, an anthracenyl group, a perylenyl group, and a pyrenyl group. Specific examples of the aryl group having 6 to 10 carbon atoms include a phenyl group and a naphthyl group. Specific examples of the aryl group having a fused structure with 10 to 16 carbon atoms include a naphthyl group, a fluorenyl group, a phenanthrenyl group, a triphenylenyl group, an anthracenyl group, a perylenyl group, and a pyrenyl group.

Specific examples of the organic compound having the above-described structure include organic compounds listed below.

[Chemical Formulae 10]
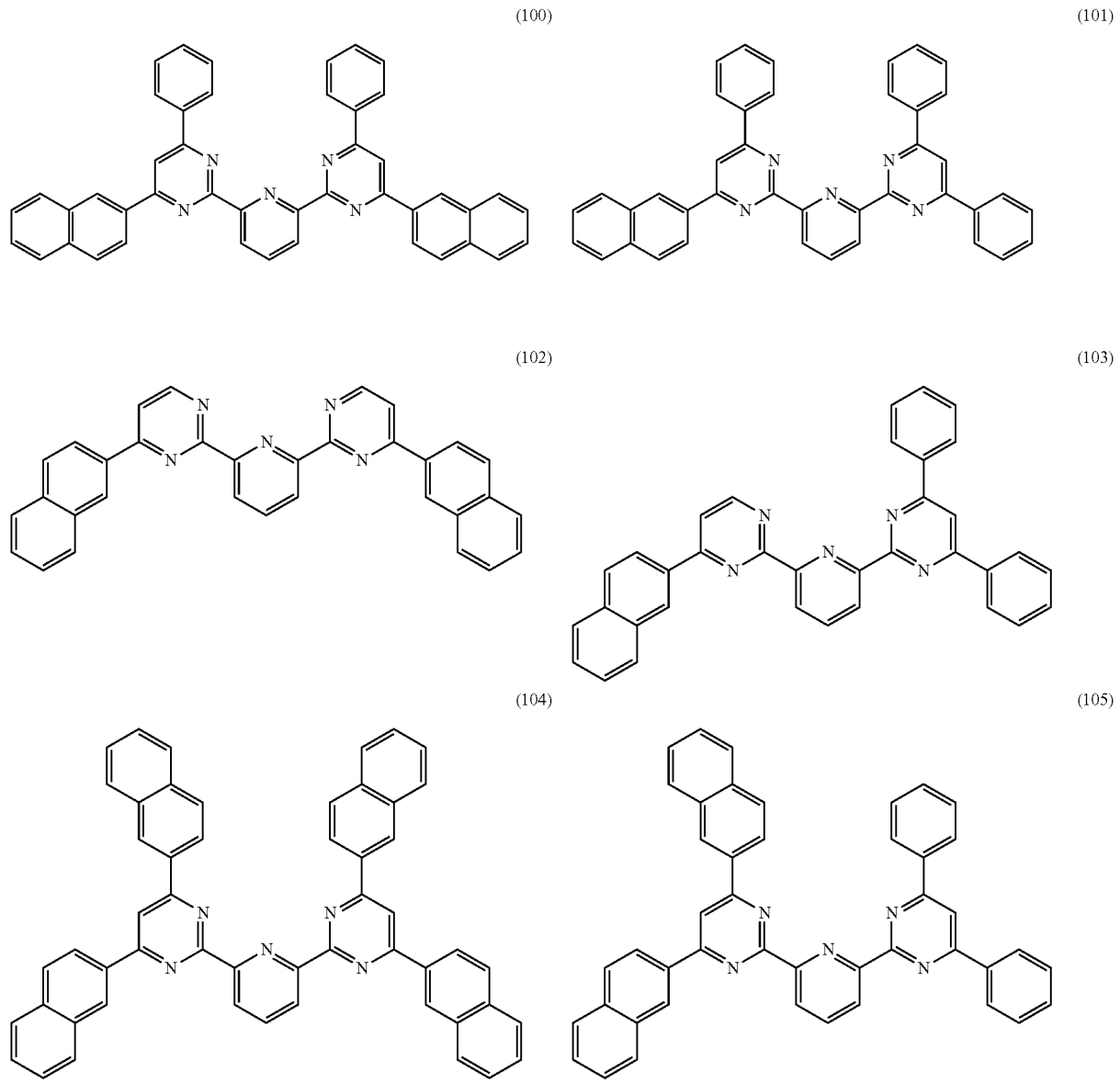
[Chemical Formulae 11]
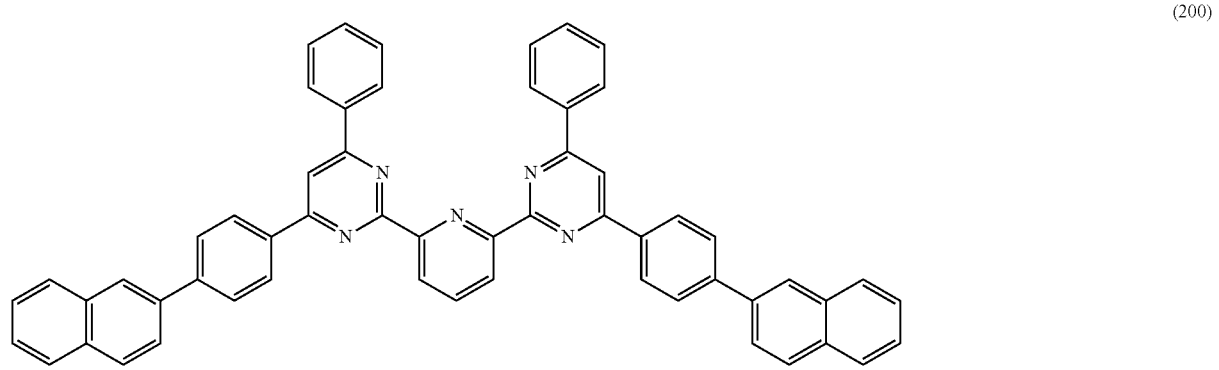

-continued
(201)
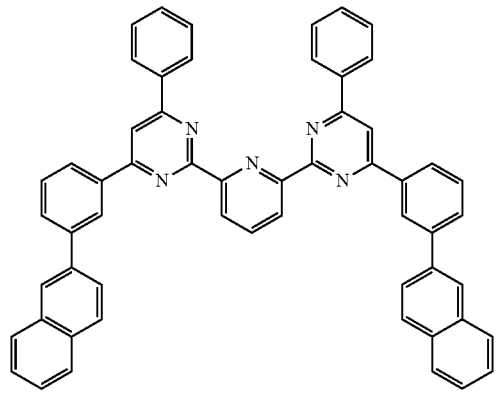
(202)
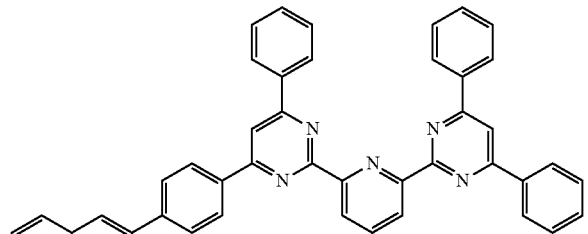
(203)
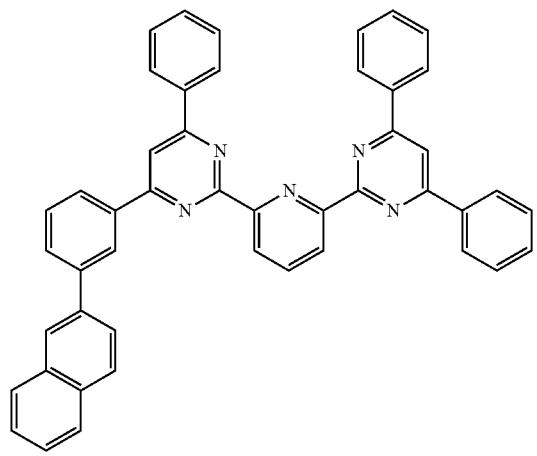
(204)
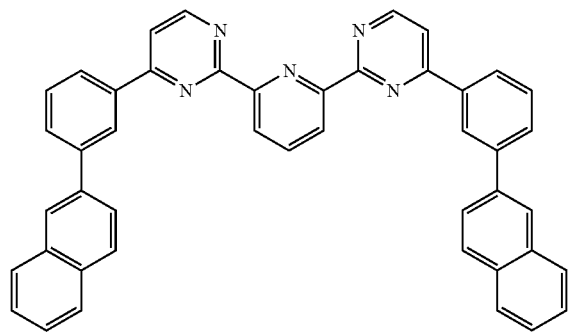
(205)
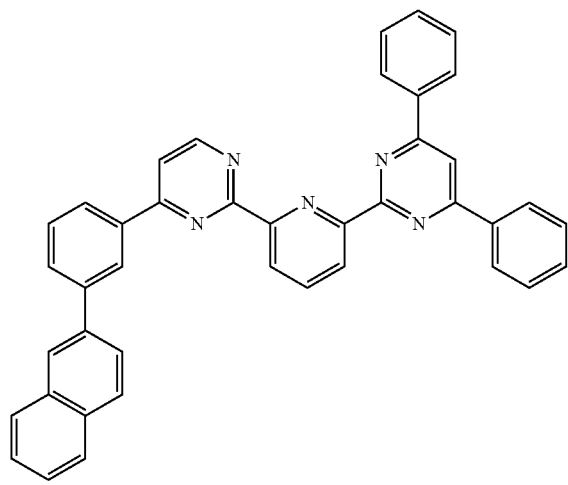

[Chemical Formulae 12]
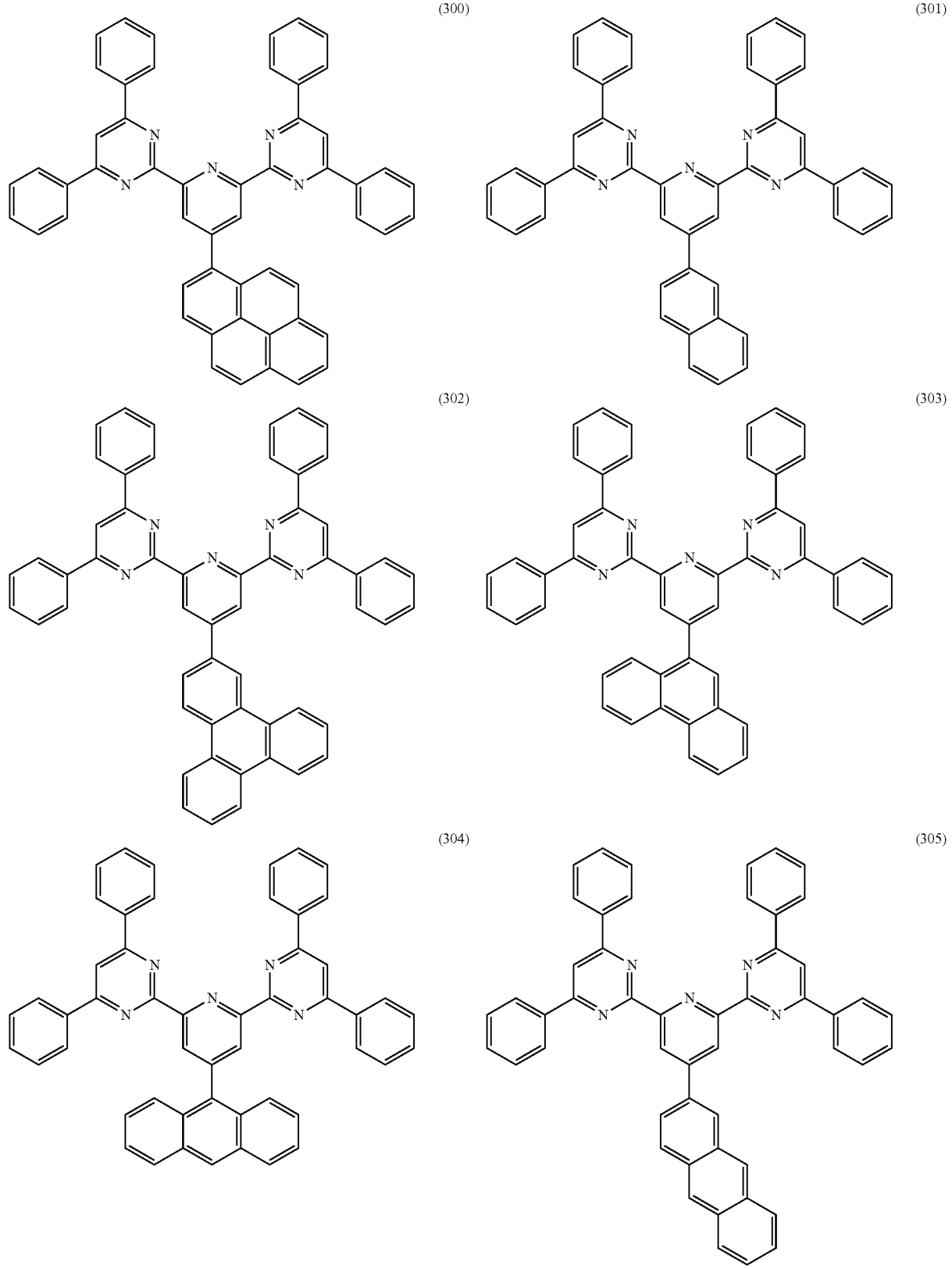

[Chemical Formulae 13]
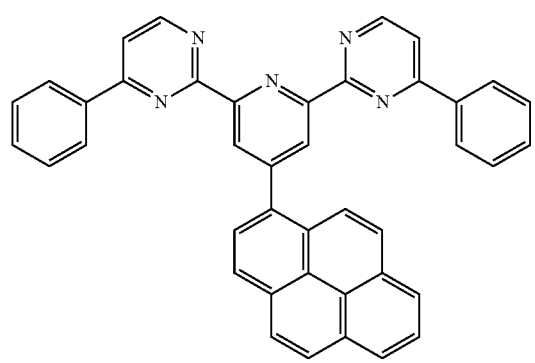 (306)
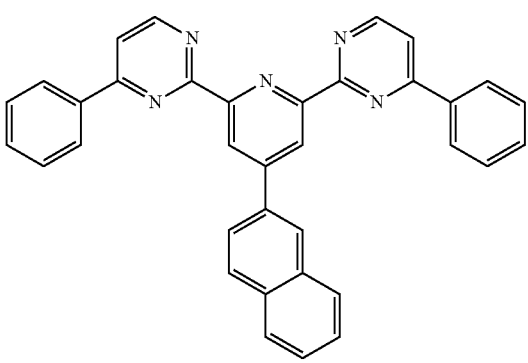 (307)
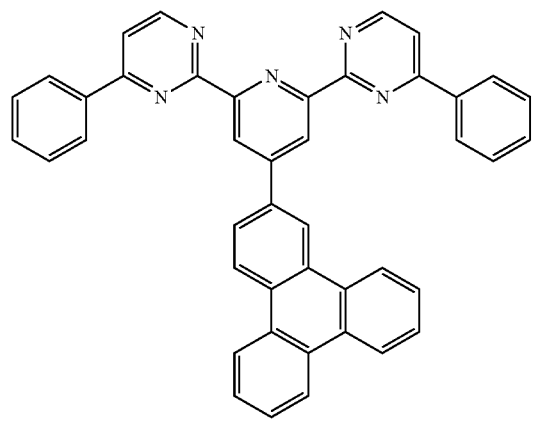 (308)
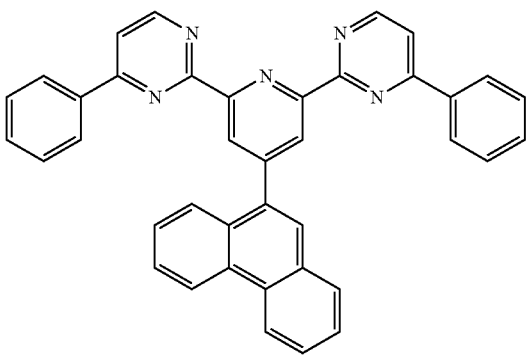 (309)
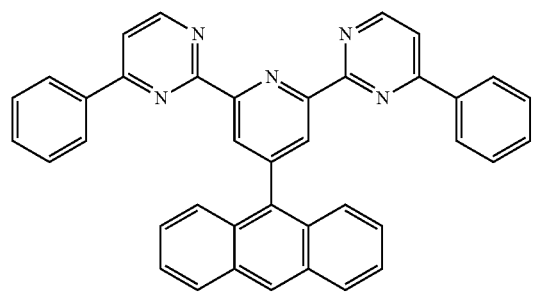 (310)
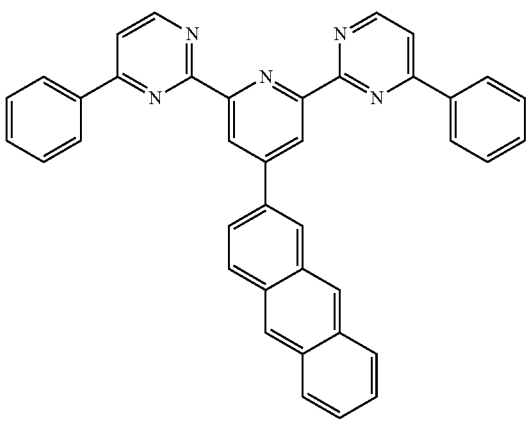 (311)

The organic compound represented by the general formula (G1) can be obtained by coupling of a halogenated pyridine compound (A1) with pyrimidine boronic acids (A2) and (A2') as illustrated in the following synthesis scheme. Alternatively, the organic compound can be synthesized by reaction of a pyridine dicarboxamidine compound with a chalcone derivative in a solvent in the presence of a base.

[Chemical Formula 14]

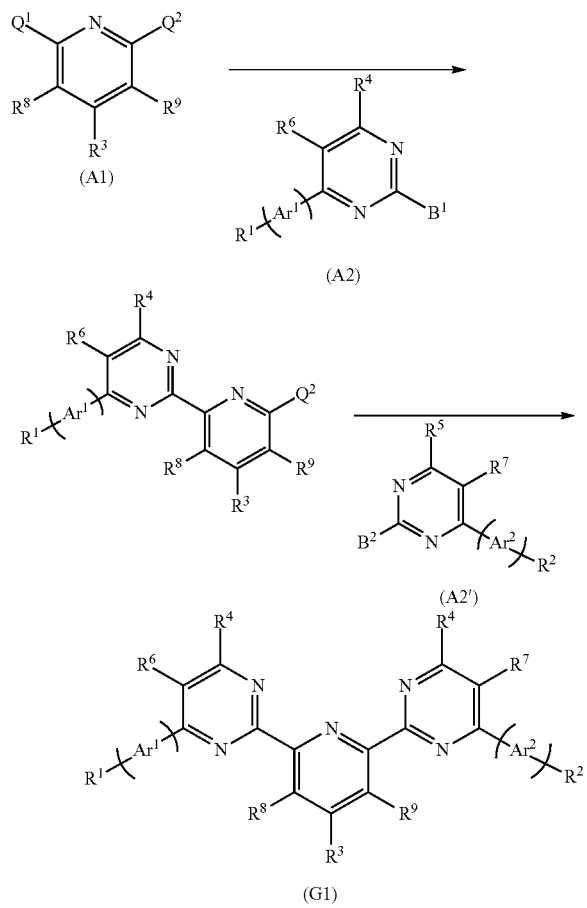

(G1)

In the above synthetic scheme, $Q^1$ and $Q^2$ represent a halogen. In addition, $B^1$ and $B^2$ represent a boronic acid, a boronic ester, a cyclic-triolborate salt, or the like. As the cyclic-triolborate salt, a lithium salt, a potassium salt, or a sodium salt may be used. $Ar^1$ and $Ar^2$ represent a phenylene group, and n and m separately represent 0 or 1. $R^1$ to $R^3$ separately represent hydrogen or an aryl group having 6 to 16 carbon atoms, at least one of which is an aryl group with a fused structure. $R^4$ to $R^9$ separately represent hydrogen, an alkyl group having 1 to 6 carbon atoms, or an aryl group having 6 to 10 carbon atoms.

Depending on the halogen represented by $Q^1$ and $Q^2$, reactions with the boronic acids can be caused in a given order or at the same time. Since a wide variety of compounds (A1) and (A2) are commercially available or their synthesis is feasible, a great variety of the organic compounds represented by the general formula (G1) can be synthesized. Thus, a feature of the organic compound of one embodiment of the present invention is the abundance of variations.

Although the example of a method for synthesizing the organic compound of one embodiment of the present invention is described above, the present invention is not limited thereto and any other synthesis method may be employed.

Embodiment 1

In this embodiment, a detailed example of the structure of the light-emitting element containing the organic compound of one embodiment of the present invention will be described below with reference to FIG. 1A.

The light-emitting element in this embodiment includes, between a pair of electrodes, an EL layer including a plurality of layers. Any of the plurality of layers contains the organic compound of one embodiment of the present invention. In this embodiment, the light-emitting element includes a first electrode 101, a second electrode 102, and an EL layer 103 which is provided between the first electrode 101 and the second electrode 102. Note that in this embodiment, the following description is made on the assumption that the first electrode 101 functions as an anode and that the second electrode 102 functions as a cathode.

Since the first electrode 101 functions as the anode, the first electrode 101 is preferably formed using any of metals, alloys, electrically conductive compounds, and mixtures thereof which have a high work function (specifically, a work function of 4.0 eV or more) or the like. Specifically, for example, indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like can be given. Films of these electrically conductive metal oxides are usually formed by a sputtering method but may be formed by application of a sol-gel method or the like. In an example of the formation method, a film of indium oxide-zinc oxide is formed by a sputtering method using a target in which 1 wt % to 20 wt % of zinc oxide is added to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like can be given. Graphene can also be used. Note that when a composite material described later is used for a layer which is in contact with the first electrode 101 in the EL layer 103, an electrode material can be selected regardless of its work function.

Figure 1B:
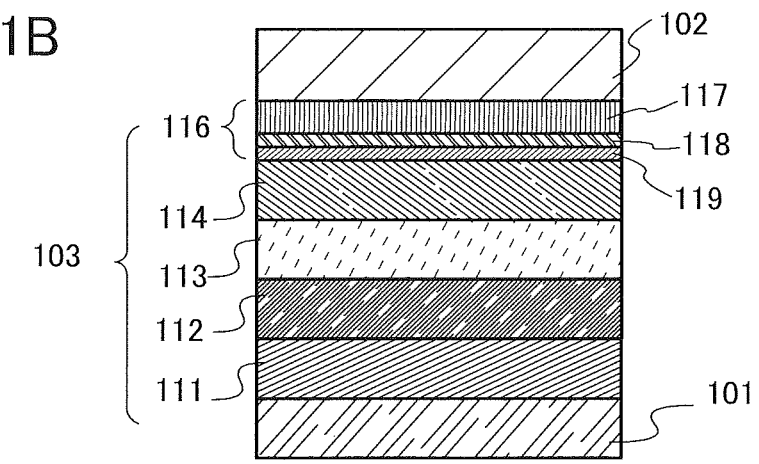

It is preferable that the EL layer 103 have a stacked-layer structure. There is no particular limitation on the stacked-layer structure as long as the organic compound of one embodiment of the present invention is contained in any of the stacked layers. For example, the EL layer 103 can be formed by combining a hole-injection layer, a hole-transport layer, a light-emitting layer, an electron-transport layer, an electron-injection layer, a carrier-blocking layer, a charge-generation layer, and the like as appropriate. In this embodiment, the EL layer 103 has either of the following two structures: a structure in which a hole-injection layer 111, a hole-transport layer 112, a light-emitting layer 113, an electron-transport layer 114, and an electron-injection layer 115 are stacked in this order over the first electrode 101 as illustrated in FIG. 1A, and a structure in which the hole-injection layer 111, the hole-transport layer 112, the light-emitting layer 113, the electron-transport layer 114, and a charge-generation layer 116 are stacked over the first electrode 101 as illustrated in FIG. 1B. Among the layers, as a host material of the light-emitting layer, the electron-transport layer, or the electron-injection layer, the organic compound of one embodiment of the present invention is preferably used; however, one embodiment of the present invention is not limited thereto. Specific examples of materials used for each layer are given below.

The hole-injection layer 111 contains a substance with a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

Alternatively, a composite material in which a substance having a hole-transport property contains a substance having an acceptor property can be used for the hole-injection layer 111. Note that the use of such a substance having a hole-transport property which contains a substance having an acceptor property enables selection of a material used to form an electrode regardless of its work function. In other words, besides a material having a high work function, a material having a low work function can also be used for the first electrode 101. Examples of the substance having an acceptor property include compounds having an electron-withdrawing group (a halogen group or a cyano group) such as 7,7,8,8-tetracyano-2,3,5,6-tetrafluoroquinodimethane (abbreviation: $F_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of hetero atoms, like HAT-CN, is thermally stable and preferable. In addition, transition metal oxides can be given. Oxides of the metals that belong to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these oxides, molybdenum oxide is particularly preferable in that it is stable in the air, has a low hygroscopic property, and is easy to handle.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm$^2$/Vs or more is preferably used. Organic compounds that can be used as the substance having a hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of $1\times10^{-6}$ cm$^2$/Vs or more and which has 14 to 42 carbon atoms is particularly preferable.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing a hole-injection layer, a high hole-injection property can be achieved to allow a light-emitting element to be driven at a low voltage.

Note that the hole-injection layer may be formed of the above-described acceptor material alone or of the above-described acceptor material and another material in combination. In this case, the acceptor material extracts electrons from the hole-transport layer, so that holes can be injected into the hole-transport layer. The acceptor material transfers the extracted electrons to the anode.

The hole-transport layer 112 contains a substance having a hole-transport property. Examples of the substance having a hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]

triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP). The substances mentioned here have a high hole-transport property and are mainly ones that have a hole mobility of $10^{-6}$ cm$^2$/Vs or more. An organic compound given as an example of the substance having a hole-transport property in the composite material described above can also be used for the hole-transport layer 112. A high molecular compound such as poly(N-vinylcarbazole) (abbreviation: PVK) and poly(4-vinyltriphenylamine) (abbreviation: PVTPA) can also be used. Note that the layer that contains the substance having a hole-transport property is not limited to a single layer, and may be a stack of two or more layers including any of the above substances.

The light-emitting layer 113 may be a layer that contains a fluorescent substance and emits fluorescence, a layer that contains a phosphorescent substance and emits phosphorescence, or a layer that contains a substance emitting thermally activated delayed fluorescence (TADF) and emits TADF. Furthermore, the light-emitting layer 113 may be a single layer or include a plurality of layers containing different light-emitting substances.

Examples of materials that can be used as the fluorescent substance in the light-emitting layer 113 are as follows. Other various fluorescent substances can also be used.

The examples include 5,6-bis[4-(10-phenyl-9-anthryl)phenyl]-2,2'-bipyridine (abbreviation: PAP2BPy),
5,6-bis[4'-(10-phenyl-9-anthryl)biphenyl-4-yl]-2,2'-bipyridine (abbreviation: PAPP2BPy),
N,N'-bis[4-(9-phenyl-9H-fluoren-9-yl)phenyl]-N,N'-diphenyl-pyrene-1,6-diamine (abbreviation: 1,6FLPAPm),
N,N'-bis(3-methylphenyl)-N,N'-bis[3-(9-phenyl-9H-fluoren-9-yl)phenyl]-pyrene-1,6-diamine (abbreviation: 1,6mMemFLPAPm),
[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA),
4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP),
4-(10-phenyl-9-anthryl)-4'-(9-phenyl-9H-carbazol-3-yl)triphenylamine (abbreviation: PCBAPA),
N,N''-(2-tert-butylanthracene-9,10-diyldi-4,1-phenylene)bis[N,N,N'-triphenyl-1,4-phenylenediamine] (abbreviation: DPABPA),
N,9-diphenyl-N-[4-(9,10-diphenyl-2-anthryl)phenyl]-9H-carbazol-3-amine (abbreviation: 2PCAPPA),
N-[4-(9,10-diphenyl-2-anthryl)phenyl]-N,N',N'-triphenyl-1,4-phenylenediamine (abbreviation: 2DPAPPA),
N,N,N',N',N'',N'',N''',N'''-octaphenyldibenzo[g,p]chrysene-2,7,10,15-tetraamine (abbreviation: DBC1), coumarin 30,
N-(9,10-diphenyl-2-anthryl)-N,9-diphenyl-9H-carbazol-3-amine (abbreviation: 2PCAPA),
N-[9,10-bis(1,1'-biphenyl-2-yl)-2-anthryl]-N,9-diphenyl-9H-carbazol-3-amine (abbreviation: 2PCABPhA),
N-(9,10-diphenyl-2-anthryl)-N,N',N'-triphenyl-1,4-phenylenediamine (abbreviation: 2DPAPA),
N-[9,10-bis(1,1'-biphenyl-2-yl)-2-anthryl]-N,N',N'-triphenyl-1,4-phenylenediamine (abbreviation: 2DPABPhA),
9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene,
5,12-bis(1,1'-biphenyl-4-yl)-6,11-diphenyltetracene (abbreviation: BPT),
2-(2-{2-[4-(dimethylamino)phenyl]ethenyl}-6-methyl-4H-pyran-4-ylidene)propanedinitrile (abbreviation: DCM1),
2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2),
N,N,N',N'-tetrakis(4-methylphenyl)tetracene-5,11-diamine (abbreviation: p-mPhTD),
7,14 diphenyl-tetrakis(4-methylphenyl)acenaphtho[1,2-a]fluoranthene-3,10-diamine (abbreviation: p-mPhAFD),
2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI),
2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB),
2-(2,6-bis{2-[4-(dimethylamino)phenyl]ethenyl}-4H-pyran-4-ylidene)propanedinitrile (abbreviation: BisDCM), and
2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM). Condensed aromatic diamine compounds typified by pyrenediamine compounds such as 1,6FLPAPm and 1,6mMemFLPAPrn are particularly preferable because of their high hole-trapping property, high emission efficiency, and high reliability.

Examples of materials that can be used as the phosphorescent substance in the light-emitting layer 113 are as follows.

The examples include organometallic iridium complexes having 4H-triazole skeletons, such as
tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]),
tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having 1H-triazole skeletons, such as
tris[3-methyl-1-(2-methylphenyl)-5-phenyl-1H-1,2,4-triazolato]iridium(III) (abbreviation: [Ir(Mptz1-mp)$_3$]) and
tris(1-methyl-5-phenyl-3-propyl-1H-1,2,4-triazolato)iridium(III) (abbreviation: [Ir(Prptz1-Me)$_3$]); organometallic iridium complexes having imidazole skeletons, such as fac-tris[1-(2,6-diisopropylphenyl)-2-phenyl-1H-imidazole]iridium(III) (abbreviation: [Ir(iPrpmi)$_3$]) and
tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N, C$^{2'}$]iridium(III)tetrakis(1-pyrazolyl)borate (abbreviation: FIr6), bis[2-(4',6'-difluorophenyl)pyridinato-N,C$^{2'}$]iridium(III)picolinate (abbreviation: FIrpic),
bis{2-[3',5'-bis(trifluoromethyl)phenyl]pyridinato-N, C$^{2'}$}iridium(III)picolinate (abbreviation: [Ir(CF$_3$ppy)$_2$(pic)]), and
bis[2-(4',6'-difluorophenyl)pyridinato-N,C$^{2'}$]iridium(III) acetylacetonate (abbreviation: FIr(acac)). These are compounds emitting blue phosphorescent light and have an emission peak at 440 nm to 520 nm.

Other examples include organometallic iridium complexes having pyrimidine skeletons, such as tris(4-methyl- 6-phenylpyrimidinato)iridium(III) (abbreviation: [Ir(mppm)₃]), tris(4-t-butyl-6-phenylpyrimidinato iridium (III) (abbreviation: [Ir(tBuppm)₃]), (acetylacetonato)bis(6-methyl-4-phenylpyrimidinato)iridium(III) (abbreviation: [Ir(mppm)₂(acac)]),
(acetylacetonato)bis(6-tert-butyl-4-phenylpyrimidinato) iridium(III) (abbreviation: [Ir(tBuppm)₂(acac)]),
(acetylacetonato)bis[6-(2-norbornyl)-4-phenylpyrimidinato] iridium(III) (abbreviation: [Ir(nbppm)₂(acac)]),
(acetylacetonato)bis[5-methyl-6-(2-methylphenyl)-4-phenylpyrimidinato]iridium(III) (abbreviation: [Ir(mpmppm)₂(acac)]), and
(acetylacetonato)bis(4,6-diphenylpyrimidinato)iridium(III) (abbreviation: [Ir(dppm)₂(acac)]); organometallic iridium complexes having pyrazine skeletons, such as (acetylacetonato)bis(3,5-dimethyl-2-phenylpyrazinato)iridium(III) (abbreviation: [Ir(mppr-Me)₂(acac)]) and
(acetylacetonato)bis(5-isopropyl-3-methyl-2-phenylpyrazinato)iridium(III) (abbreviation: [Ir(mppr-iPr)₂(acac)]); organometallic iridium complexes having pyridine skeletons, such as tris(2-phenylpyridinato-N,C²')iridium(III) (abbreviation: [Ir(ppy)₃]),
bis(2-phenylpyridinato-N,C²')iridium(III)acetylacetonate (abbreviation: [Ir(ppy)₂(acac)]), bis(benzo[h]quinolinato) iridium(III)acetylacetonate (abbreviation: [Ir(bzq)₂(acac)]), tris(benzo[h]quinolinato)iridium(III) (abbreviation: [Ir(bzq)₃]),
tris(2-phenylquinolinato-N,C²')iridium(III) (abbreviation: [Ir(pq)₃]), and
bis(2-phenylquinolinato-N,C²')iridium(III)acetylacetonate (abbreviation: [Ir(pq)₂(acac)]); and rare earth metal complexes such as tris(acetylacetonato)(monophenanthroline) terbium(III) (abbreviation: [Tb(acac)₃(Phen)]). These are mainly compounds emitting green phosphorescent light and have an emission peak at 500 nm to 600 nm Note that organometallic iridium complexes having pyrimidine skeletons have distinctively high reliability and emission efficiency and thus are especially preferable.

Other examples include organometallic iridium complexes having pyrimidine skeletons, such as
(diisobutyrylmethanato)bis[4,6-bis(3-methylphenyl)pyrimidinato]iridium(III) (abbreviation: [Ir(5mdppm)₂(dibm)]),
bis[4,6-bis(3-methylphenyl)pyrimidinato](dipivaloylmethanato)iridium(III) (abbreviation: [Ir(5mdppm)₂(dpm)]),
bis[4,6-di(naphthalen-1-yl)pyrimidinato](dipivaloylmethanato)iridium(III) (abbreviation: [Ir(d1npm)₂(dpm)]); organometallic iridium complexes having pyrazine skeletons, such as (acetylacetonato)bis(2,3,5-triphenylpyrazinato)iridium(III) (abbreviation: [Ir(tppr)₂(acac)]),
bis(2,3,5-triphenylpyrazinato)(dipivaloylmethanato)iridium (III) (abbreviation: [Ir(tppr)₂(dpm)]), and
(acetylacetonato)bis[2,3-bis(4-fluorophenyl)quinoxalinato] iridium(III) (abbreviation: [Ir(Fdpq)₂(acac)]); organometallic iridium complexes having pyridine skeletons, such as
tris(1-phenylisoquinolinato-N,C²')iridium(III) (abbreviation: [Ir(piq)₃]) and bis(1-phenylisoquinolinato-N,C²') iridium(III) acetylacetonate (abbreviation: [Ir(piq)₂(acac)]); platinum complexes such as
2,3,7,8,12,13,17,18-octaethyl-21H,23H-porphyrin platinum (II) (abbreviation: PtOEP); and rare earth metal complexes such as
tris(1,3-diphenyl-1,3-propanedionato)(monophenanthroline)europiumn(III) (abbreviation: [Eu(DBM)₃(Phen)]) and tris [1-(2-thenoyl)-3,3,3-trifluoroacetonato](thonophenanthroline)europium(III) (abbreviation: [Eu(TTA)₃(Phen)]). These are compounds emitting red phosphorescent light and have an emission peak at 600 nm to 700 nm. Furthermore, organometallic iridium complexes having pyrazine skeletons can provide red light emission with favorable chromaticity.

As well as the above phosphorescent compounds, a variety of phosphorescent substances may be selected and used.

Examples of the TADF material include a fullerene, a derivative thereof, an acridine derivative such as proflavine, eosin, or the like, and a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF₂(Proto IX)), a mesoporphyrin-tin fluoride complex (SnF₂(Meso IX)), a hematoporphyrin-tin fluoride complex (SnF₂(Hemato IX)), a coproporphyrin tetramethyl ester-tin fluoride complex (SnF₂(Copro III-4Me)), an octaethylporphyrin-tin fluoride complex (SnF₂(OEP)), an etioporphyrin-tin fluoride complex (SnF₂(Etio I)), and an octaethylporphyrin-platinum chloride complex (PtCl₂(OEP)), which are shown in the following structural formulae.

[Chemical Formulae 15]

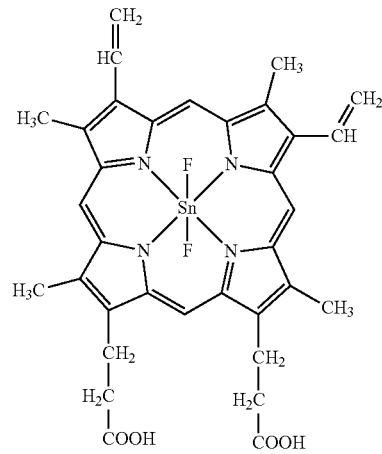

SnF₂(Proto IX)

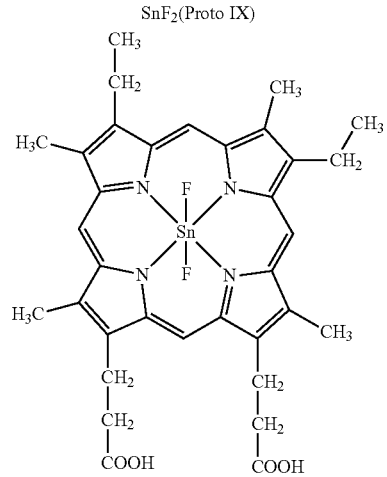

SnF₂(Meso IX)

-continued

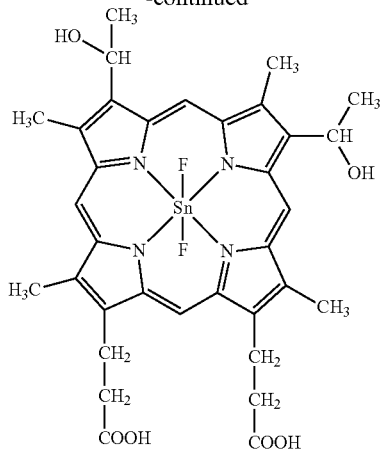

SnF₂(Hemato IX)

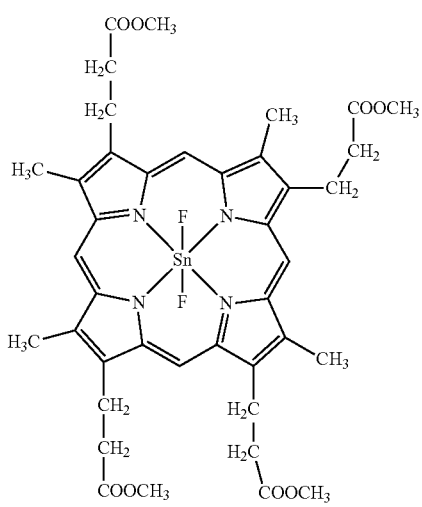

SnF₂(Copro III-4Me)

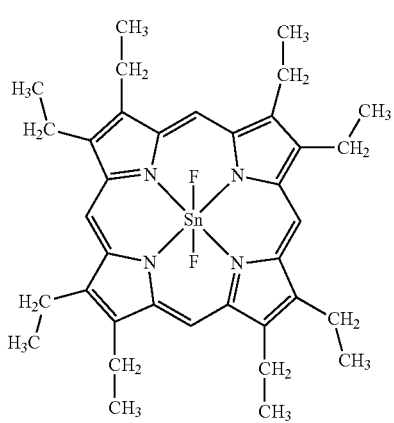

SnF₂(OEP)

-continued

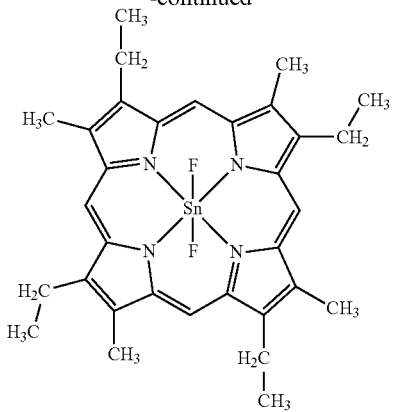

SnF₂(Etio I)

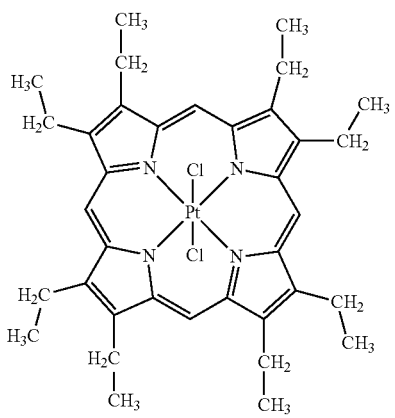

PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (PIC-TRZ) shown in the following structural formula, can be used. The heterocyclic compound is preferably used because of the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the energy difference between the $S_1$ level and the $T_1$ level becomes small.

[Chemical Formula 16]

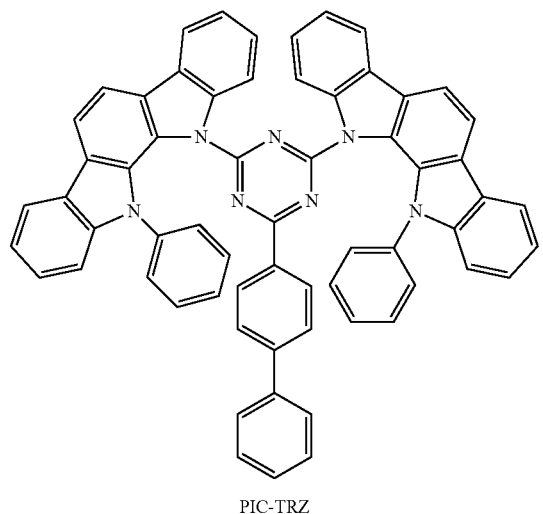

PIC-TRZ

A variety of carrier-transport materials can be used as the host material of the light-emitting layer. As the carrier-transport material, any of substances having a hole-transport property and substances having an electron-transport property listed below and the like can be used. It is needless to say that it is possible to use a material having a hole-transport property, a material having an electron-transport property, or a bipolar material other than the substances listed below.

The following are examples of materials having a hole-transport property: compounds having aromatic amine skeletons, such as
4,4'-bis[N-(1-naphthyl)-N-phenylamino]biphenyl (abbreviation: NPB),
N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP),
4-phenyl-3'-(9-phenylfluoren-9-yl)triphenylamine (abbreviation: mBPAFLP),
4-phenyl-4'-(9-phenyl-9H-carbazol-3-yl)triphenylamine (abbreviation: PCBA1BP),
4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB),
4,4'-di(1-naphthyl)-4''-(9-phenyl-9H-carbazol-3-yl)triphenylamine (abbreviation: PCBNBB),
9,9-dimethyl-N-phenyl-N-[4-(9-phenyl-9H-carbazol-3-yl)phenyl]fluoren-2-amine (abbreviation: PCBAF), and
N-phenyl-N-[4-(9-phenyl-9H-carbazol-3-yl)phenyl]spiro-9,9'-bifluoren-2-amine (abbreviation: PCBASF); compounds having carbazole skeletons, such as
1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4''-(benzene-1,3,5-triyl)tri(dibenzothiophene) (abbreviation: DBT3P-II),
2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as
4,4',4''-(benzene-1,3,5-triyl)tri(dibenzofuran) (abbreviation: DBF3P-II) and
4-{3-[3-(9-phenyl-9H-fluoren-9-yl)phenyl]phenyl}dibenzofuran (abbreviation: mmDBFFLBi-II). Among the above materials, compounds having aromatic amine skeletons and compounds having carbazole skeletons are preferable because these compounds are highly reliable and have a high hole-transport property to contribute to a reduction in drive voltage.

The following are examples of materials having an electron-transport property: the organic compound of one embodiment of the present invention; metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq),
bis[2-(2-benzoxazolyl)phenolato]zinc(II) (abbreviation: ZnPBO), and
bis[2-(2-benzothiazolyl)phenolato]zinc(II) (abbreviation: ZnBTZ); heterocyclic compounds having polyazole skeletons, such as
2-(4-biphenylyl)-5-(4-tert-butylphenyl)-1,3,4-oxadiazole (abbreviation: PBD),
3-(4-biphenylyl)-4-phenyl-5-(4-tert-butylphenyl)-1,2,4-triazole (abbreviation: TAZ),
1,3-bis[5-(p-tert-butylphenyl)-1,3,4-oxadiazol-2-yl]benzene (abbreviation: OXD-7),
9-[4-(5-phenyl-1,3,4-oxadiazol-2-yl)phenyl]-9H-carbazole (abbreviation: CO11),
2,2',2''-(1,3,5-benzenetriyl)tris(1-phenyl-1H-benzimidazole) (abbreviation: TPBI), and
2-[3-(dibenzothiophen-4-yl)phenyl]1-phenyl-1H-benzimidazole (abbreviation: mDBTBIm-II); heterocyclic compounds having diazine skeletons, such as
2-[3-(dibenzothiophen-4-yl)phenyl]dibenzo[fh]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II),
2-[3'-(9H-carbazol-9-yl)biphenyl-3-yl]dibenzo[fh]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having pyridine skeletons, such as
3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above compounds, heterocyclic compounds having diazine skeletons and heterocyclic compounds having pyridine skeletons have high reliability and are thus preferable. Heterocyclic compounds having diazine (pyrimidine or pyrazine) skeletons have a high electron-transport property and contribute to a decrease in drive voltage.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed by these mixed materials. It is preferable that the combination of these materials be selected so as to form an exciplex that exhibits light emission whose wavelength overlaps with a wavelength of a lowest-energy-side absorption band of the light-emitting material, in which case energy is transferred smoothly, light emission can be obtained efficiently, and the drive voltage is reduced.

The light-emitting layer 113 having the above-described structure can be formed by co-evaporation by a vacuum evaporation method, or a gravure printing method, an offset printing method, an inkjet method, a spin coating method, a dip coating method, or the like using a mixed solution of the host material and the light-emitting substance.

The electron-transport layer 114 contains a substance having an electron-transport property. As the substance having an electron-transport property, it is possible to use any of the above-listed substances having an electron-transport property that can be used as a host material. The organic compound of one embodiment of the present invention can be suitably used. It is particularly preferable that the organic compound of one embodiment of the present invention be contained at least in a portion of the electron-transport layer 114 in contact with the electron-injection layer 115 because the reliability of the light-emitting element can be improved.

Between the electron-transport layer 114 and the light-emitting layer 113, a layer that controls transport of electron carriers may be provided. This is a layer formed by addition of a small amount of a substance having a high electron-trapping property to the aforementioned materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. An electride may also be used for the electron-injection layer 115. Examples of the electride include a substance in which electrons are added at high concentration to calcium oxide-aluminum oxide. Note that a layer that is formed using a substance having an electron-transport property and contains an alkali metal or an alkaline earth metal is preferably used as the electron-injection layer 115, in which case electron injection from the second electrode 102 is efficiently performed. Note that it is further preferable to use the organic compound of one embodiment of the present invention as the substance having an electron-transport property.

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes a layer (a p-type layer 117) containing any of the composite materials given above as examples of materials that can be used for the hole-injection layer 111. The p-type layer 117 may be formed by stacking a film containing the above-described acceptor material and a film containing the above-described hole-transport material. When a potential is applied to the p-type layer, electrons are injected into the electron-transport layer 114 and holes are injected into the second electrode 102 serving as a cathode; thus, the light-emitting element operates. When a layer containing the organic compound of one embodiment of the present invention exists in the electron-transport layer 114 so as to be in contact with the charge-generation layer 116, a luminance decrease due to accumulation of driving time of the light-emitting element can be suppressed, and thus, the light-emitting element can have a long lifetime.

Note that the charge-generation layer 116 preferably includes either an electron-relay layer 118 or an electron-injection buffer layer 119 or both in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is set to be between the LUMO level of an acceptor substance in the p-type layer 117 and the LUMO level of a substance contained in a layer of the electron-transport layer 114 in contact with the charge-generation layer 116. As a specific value of the energy level, the LUMO level of the substance having an electron-transport property contained in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used. Furthermore, the organic compound of one embodiment of the present invention can be used.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the electrode may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, a spin coating method, or the like may be used.

Different methods may be used to form the electrodes or the layers described above.

In the light-emitting element having the above-described structure, current flows due to a potential difference generated between the first electrode 101 and the second electrode 102, and holes and electrons recombine in the light-emitting layer 113, which is a layer containing a substance having a high light-emitting property, so that light is emitted.

Light generated in the light-emitting layer is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer in contact with a side closer to the recombination region in the light-emitting layer 113, are formed using a substance having a wider band gap than the light-emitting substance of the light-emitting layer or the emission center substance included in the light-emitting layer.

Next, an embodiment of a light-emitting element with a structure in which a plurality of light-emitting units are stacked (hereinafter this type of light-emitting element is also referred to as a stacked element) is described with reference to FIG. 1C. In this light-emitting element, a plurality of light-emitting units are provided between a first electrode and a second electrode. One light-emitting unit has a structure similar to that of the EL layer 103, which is illustrated in FIG. 1A. In other words, the light-emitting element illustrated in FIG. 1A includes a single light-emitting unit; the light-emitting element in this embodiment includes a plurality of light-emitting units.

Figure 1C:
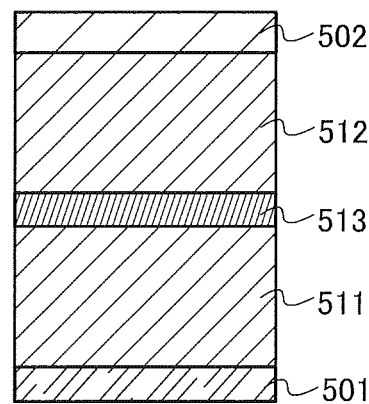

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the above-described structure of the charge-generation layer 116. Since the composite material of an organic compound and a metal oxide is superior in carrier-injection property and carrier-transport property, low-voltage driving or low-current driving can be achieved. Note that when a surface of a light-emitting unit on the anode side is in contact with the charge-generation layer 513, the charge-generation layer 513 can also serve as a hole-injection layer of the light-emitting unit; thus, a hole-transport layer is not necessarily formed in the light-emitting unit.

In the case where the electron-injection buffer layer 119 is provided, the electron-injection buffer layer serves as the electron-injection layer in the light-emitting unit on the anode side; therefore, the light-emitting unit does not further need an electron-injection layer.

Note that when a layer in contact with a surface of the charge-generation layer 513 on the anode side in a light-emitting unit contains the organic compound of one embodiment of the present invention, a luminance decrease due to accumulation of driving time can be suppressed, and thus, the light-emitting element can have high reliability.

The light-emitting element having two light-emitting units is described with reference to FIG. 1C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide a light-emitting element which can emit light with high luminance with the current density kept low and has a long lifetime. Moreover, a light-emitting device having low power consumption, which can be driven at low voltage, can be achieved.

Furthermore, when emission colors of light-emitting units are made different, light emission of a desired color can be provided from the light-emitting element as a whole. For example, in a light-emitting element having two light-emitting units, the emission colors of the first light-emitting unit may be red and green and the emission color of the second light-emitting unit may, be blue, so that the light-emitting element can emit white light as the whole element.

The above-described structure can be combined with any of the structures in this embodiment and the other embodiments.

The light-emitting element having the above structure in this embodiment has high reliability and high heat resistance.

Embodiment 2

In this embodiment, a light-emitting device including the light-emitting element containing the organic compound of one embodiment of the present invention is described.

Figure 2A:
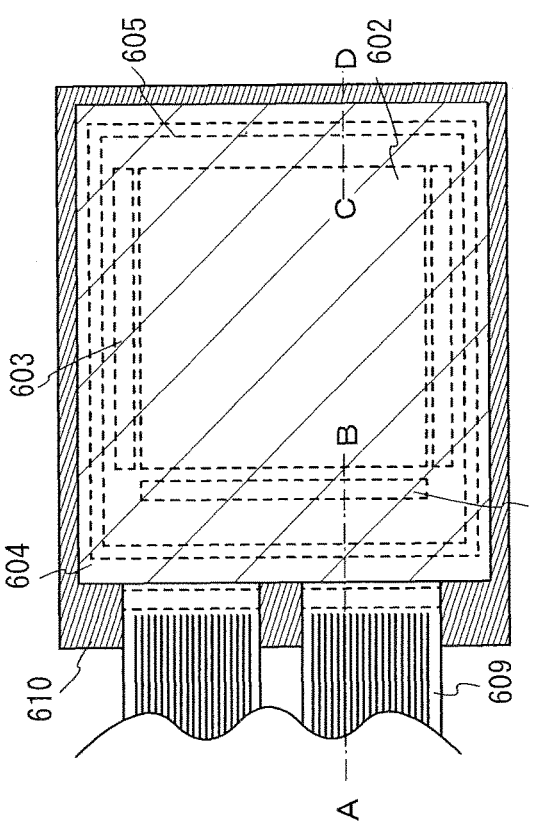
FIGS. 2A and 2B are schematic diagrams of an active matrix light-emitting device.
Figure 2B:
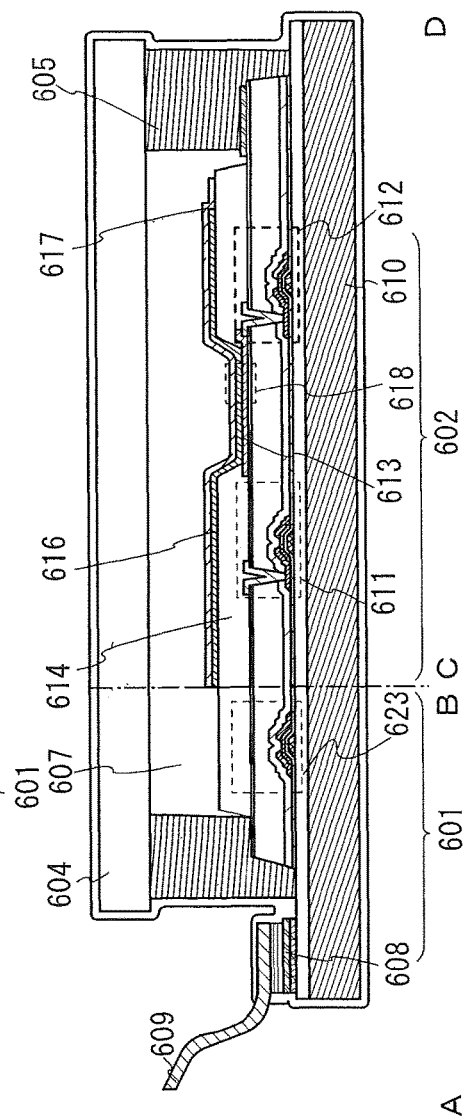

In this embodiment, the light-emitting device manufactured using the light-emitting element containing the organic compound of one embodiment of the present invention is described with reference to FIGS. 2A and 2B. Note that FIG. 2A is a top view of the light-emitting device and FIG. 2B is a cross-sectional view taken along the lines A-B and C-D in FIG. 2A. This light-emitting device includes a driver circuit portion (source line driver circuit) 601, a pixel portion 602, and a driver circuit portion (gate line driver circuit) 603, which are to control light emission of a light-emitting element and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure will be described with reference to FIG. 2B. The driver circuit portions and the pixel portion are formed over an element substrate 610; FIG. 2B shows the source line driver circuit 601, which is a driver circuit portion, and one pixel in the pixel portion 602.

The element substrate 610 may be manufactured using a substrate containing glass, quartz, an organic resin, a metal, an alloy, a semiconductor, or the like.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with an extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic is used as a material of the insulator 614, only the upper end portion of the insulator 614 preferably has a curved surface with a curvature radius (0.2 µm to 3 µm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 1. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element is the light-emitting element containing the organic compound of one embodiment of the present invention. In the light-emitting device of this embodiment, the pixel portion, which includes a plurality of light-emitting elements, may include both the light-emitting element containing the organic compound of one embodiment of the present invention and a light-emitting element having a different structure.

The sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with a filler, or may be filled with an inert gas (such as nitrogen or argon), or the sealing material 605. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), poly(vinyl fluoride) (PVF), polyester, and acrylic can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting device manufactured using the light-emitting element containing the organic compound of one embodiment of the present invention can be obtained.

The light-emitting device in this embodiment is fabricated using the light-emitting element containing the organic compound of one embodiment of the present invention and thus can have favorable characteristics. Specifically, since the light-emitting element containing the organic compound of one embodiment of the present invention has high heat resistance, the light-emitting device can have high heat resistance. In addition, since the light-emitting element can be easily mass-produced, the light-emitting device can be provided at low cost.

FIGS. 3A and 3B each illustrate an example of a light-emitting device in which full color display is achieved by formation of a light-emitting element exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is aligned and fixed to the substrate 1001. Note that the coloring layers and the black layer are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
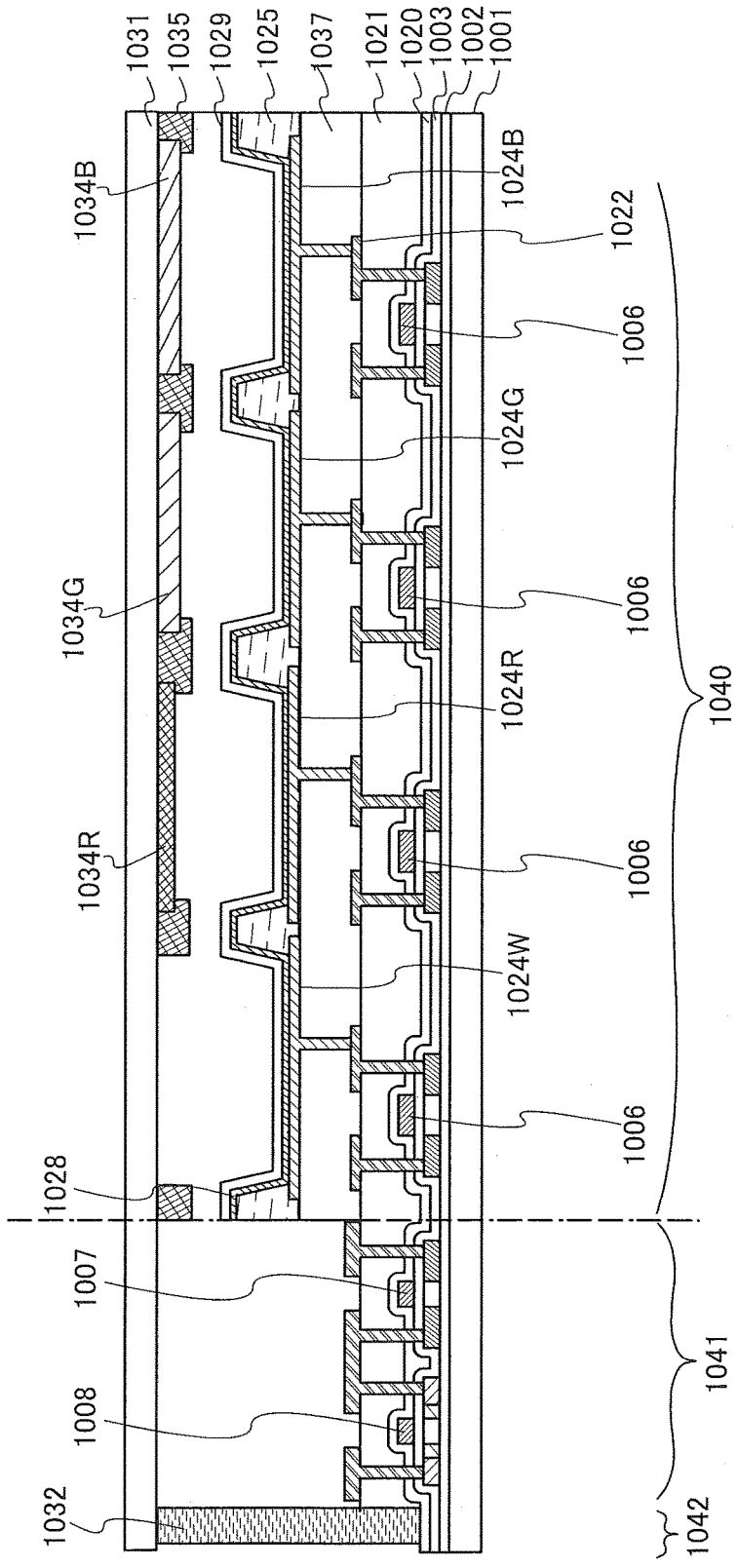
FIG. 4 is a schematic diagram of an active matrix light-emitting device.

The above-described light-emitting device is a light-emitting device having a structure in which light is extracted from the substrate 1001 side where FETs are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting elements each serve as an anode here, but may serve as a cathode. Furthermore, in the case of a light-emitting device having a top emission structure as illustrated in FIG. 4, the first electrodes are preferably reflective electrodes. The EL layer 1028 is formed to have a structure similar to the structure of the EL layer 103, which is described in Embodiment 1, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer. Note that a light-transmitting substrate is used as the sealing substrate 1031. Although an example in which full color display is performed using four colors of red, green, blue, and white is shown here, there is no particular limitation and full color display using four colors of red, yellow, green, and blue or three colors of red, green, and blue may be performed.

In the light-emitting device having a top emission structure, a microcavity structure can be favorably employed. A light-emitting element with a microcavity structure is formed with the use of a reflective electrode as the first electrode and a semi-transmissive and semi-reflective electrode as the second electrode. The light-emitting element with a microcavity structure includes at least an EL layer between the reflective electrode and the semi-transmissive and semi-reflective electrode, which includes at least a light-emitting layer serving as a light-emitting region.

Note that the reflective electrode has a visible light reflectivity of 40% to 100%, preferably 70% to 100%, and a resistivity of $1 \times 10^{-2}$ Ωcm or lower. In addition, the semi-transmissive and semi-reflective electrode has a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting element, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting element described above may be combined with a plurality of EL layers; for example, a light-emitting element may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting device which displays images with subpixels of four colors, red, yellow, green, and blue, the light-emitting device can have favorable characteristics because the luminance can be increased owing to yellow light emission and each subpixel can employ a microcavity structure suitable for wavelengths of the corresponding color.

The light-emitting device in this embodiment is fabricated using the light-emitting element containing the organic compound of one embodiment of the present invention and thus can have favorable characteristics. Specifically, since the light-emitting element containing the organic compound of one embodiment of the present invention has high heat resistance, the light-emitting device can have high heat resistance.

Figure 5A:
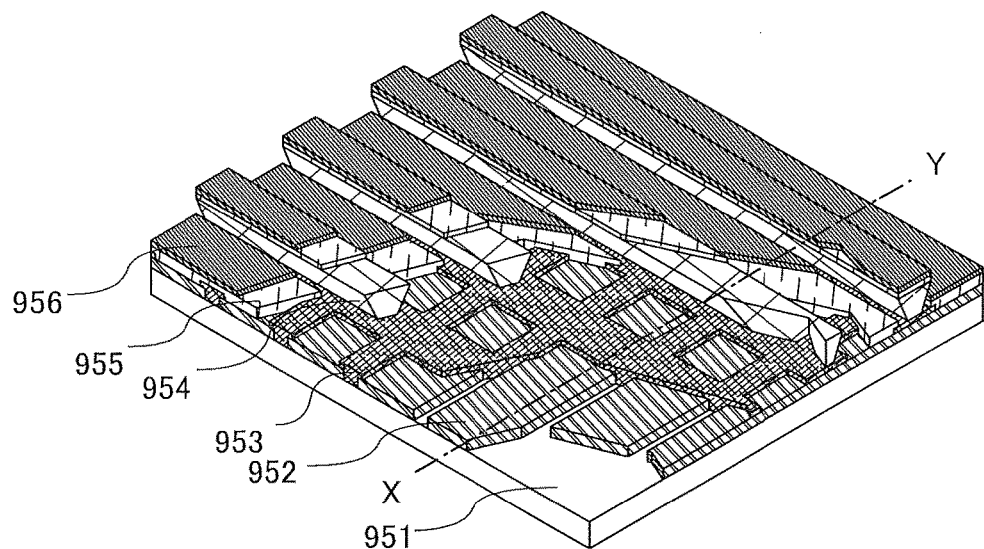
FIGS. 5A and 5B are schematic diagrams of a passive matrix light-emitting device.
Figure 5B:
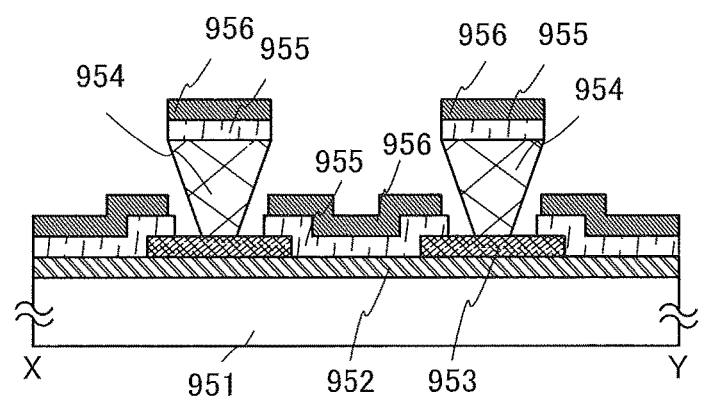

An active matrix light-emitting device is described above, whereas a passive matrix light-emitting device is described below. FIGS. 5A and 5B illustrate a passive matrix light-emitting device manufactured using the present invention. Note that FIG. 5A is a perspective view of the light-emitting device, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are a slope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting element due to static electricity or others. The passive-matrix light-emitting device also includes the light-emitting element containing the organic compound of one embodiment of the present invention; thus, the light-emitting device can have high heat resistance.

Since many minute light-emitting elements arranged in a matrix in the light-emitting device described above can each be controlled, the light-emitting device can be suitably used as a display device for displaying images.

This embodiment can be freely combined with any of the other embodiments.

Embodiment 3

Figure 6A:
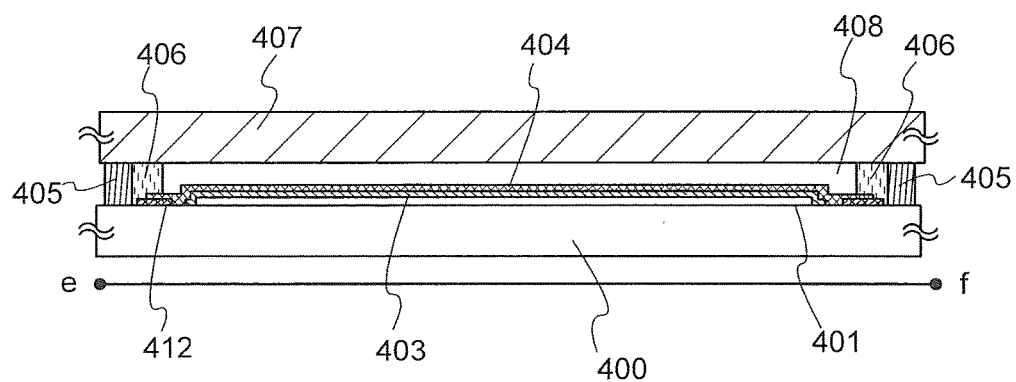
FIGS. 6A and 6B illustrate a lighting device.
Figure 6B:
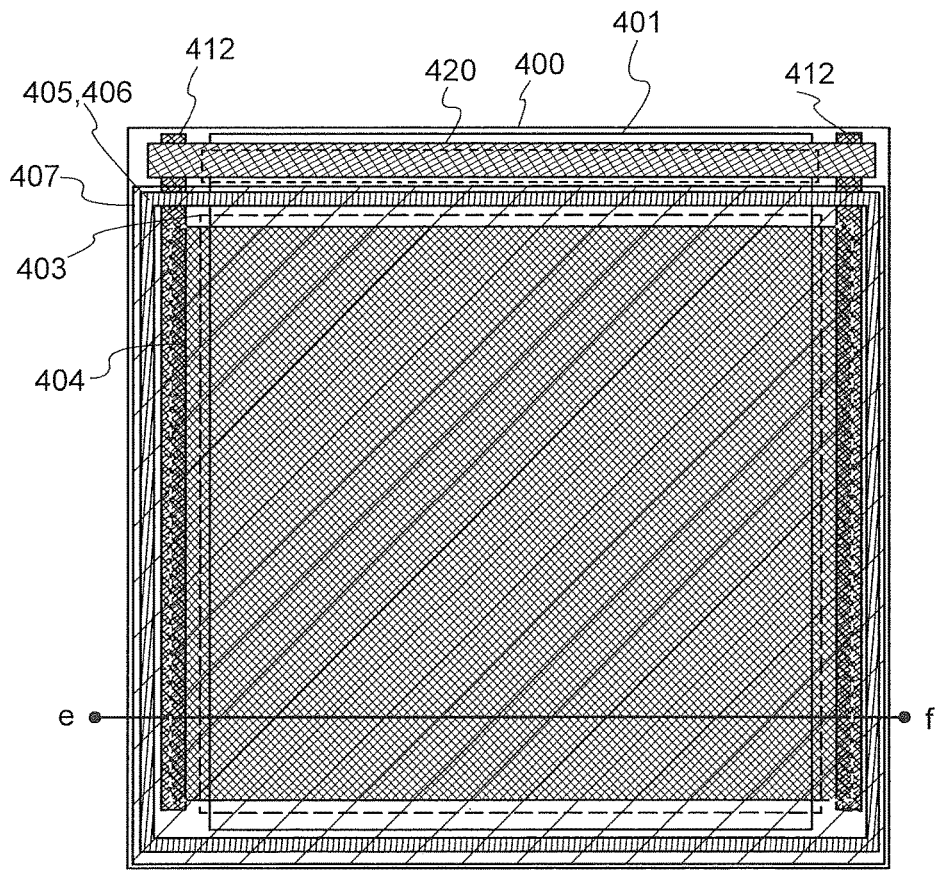

In this embodiment, an example in which the light-emitting element containing the organic compound of one embodiment of the present invention is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support and has a light-transmitting property. The first electrode 401 corresponds to the first electrode 101 in Embodiment 1. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 1, or the structure in which the light-emitting units 511 and 512 and the charge-generation layer 513 are combined. Refer to the descriptions for the structure.

The second electrode 404 is formed to cover the EL layer 403. The second electrode 404 corresponds to the second electrode 102 in Embodiment 1. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting element including the first electrode 401, the EL layer 403, and the second electrode 404. Since the light-emitting element is a light-emitting element with high emission efficiency, the lighting device in this embodiment can be a lighting device having low power consumption.

The substrate 400 provided with the light-emitting element having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting element containing the organic compound of one embodiment of the present invention; thus, the lighting device can have high reliability. The lighting device can also have high heat resistance.

Embodiment 4

In this embodiment, examples of electronic devices each including the light-emitting element containing the organic compound of one embodiment of the present invention will be described. The light-emitting element containing the organic compound of one embodiment of the present invention has high heat resistance and high reliability. As a result, the electronic devices described in this embodiment can each include a light-emitting portion having high reliability.

Examples of the electronic devices to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are given below.

Figure 7A:
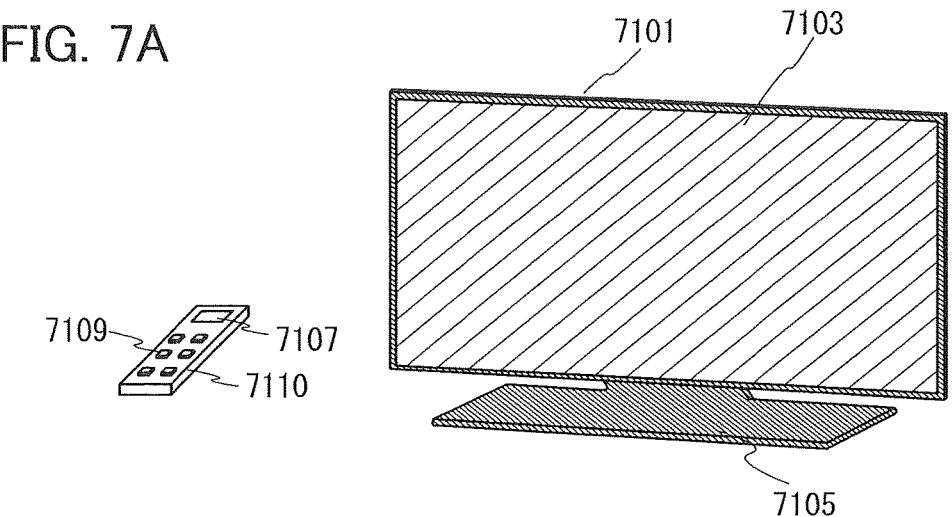
Figure 7A:
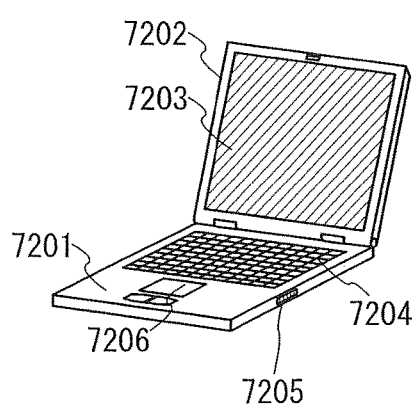
Figure 7A:
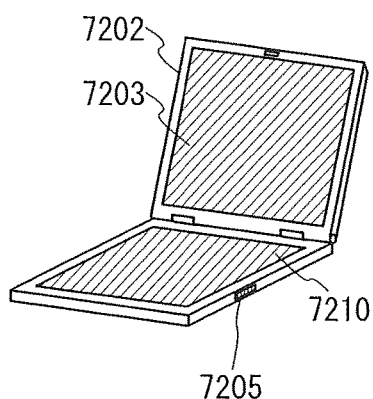

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements each containing the organic compound of one embodiment of the present invention are arranged in a matrix.

Operation of the television device can be performed with an operation switch of the housing 7101 or a separate remote controller 7110. With operation keys 7109 of the remote controller 7110, channels and volume can be controlled and images displayed on the display portion 7103 can be controlled. The remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured by arranging light-emitting elements similar to those described in Embodiment 1 in a matrix in the display portion 7203. The computer illustrated in FIG. 7B1 may have a structure illustrated in FIG. 7B2. The computer illustrated in FIG. 7B2 is provided with a second display portion 7210 instead of the keyboard 7204 and the pointing device 7206. The second display portion 7210 has a touch screen, and input can be performed by operation of images, which are displayed on the second display portion 7210, with a finger or a dedicated pen. The second display portion 7210 can also display images other than the display for input. The display portion 7203 may also have a touch screen. Connecting the two screens with a hinge can prevent troubles; for example, the screens can be prevented from being cracked or broken while the computer is being stored or carried.

Figure 7C:
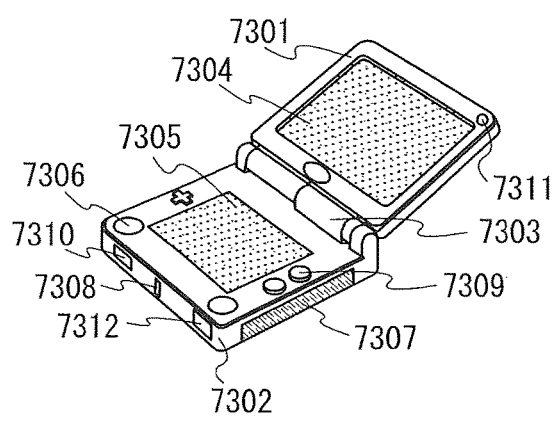

FIG. 7C illustrates a portable game machine having two housings, a housing 7301 and a housing 7302, which are connected with a joint portion 7303 so that the portable game machine can be folded. The housing 7301 incorporates a display portion 7304 in which the light-emitting elements each containing the organic compound of one embodiment of the present invention are arranged in a matrix, and the housing 7302 incorporates a display portion 7305. In addition, the portable game machine illustrated in FIG. 7C includes a speaker portion 7306, a recording medium insertion portion 7307, an LED lamp 7308, input means (an operation key 7309, a connection terminal 7310, a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion in which the light-emitting elements each containing the organic compound of one embodiment of the present invention are arranged in a matrix is used as either the display portion 7304 or the display portion 7305, or both, and the structure can include other accessories as appropriate. The portable game machine illustrated in FIG. 7C has a function of reading out a program or data stored in a recoding medium to display it on the display portion, and a function of sharing information with another portable game machine by wireless communication. Note that functions of the portable game machine illustrated in FIG. 7C are not limited to them, and the portable game machine can have various functions.

Figure 7D:
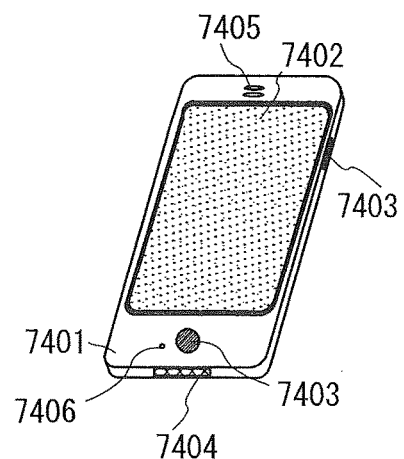

FIG. 7D illustrates an example of a portable terminal. The portable terminal is provided with a display portion 7402 incorporated in a housing 7401, operation buttons 7403, an external connection port 7404, a speaker 7405, a microphone 7406, and the like. Note that the portable terminal has the display portion 7402 in which the light-emitting elements each containing the organic compound of one embodiment of the present invention are arranged in a matrix.

When the display portion 7402 of the portable terminal illustrated in FIG. 7D is touched with a finger or the like, data can be input into the portable terminal. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode is selected for the display portion 7402 so that characters displayed on a screen can be input. In this case, it is preferable to display a keyboard or number buttons on almost the entire screen of the display portion 7402.

When a sensing device including a sensor such as a gyroscope or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Furthermore, by providing a backlight or a sensing light source which emits near-infrared light in the display portion, an image of a finger vein, or a palm vein can be taken.

Note that the structure described in this embodiment can be combined with any of the structures described in Embodiments 1 to 3 as appropriate.

As described above, the application range of the light-emitting device including the light-emitting element containing the organic compound of one embodiment of the present invention is wide so that this light-emitting device can be applied to electronic devices in a variety of fields. By using the light-emitting element containing the organic compound of one embodiment of the present invention, an electronic device having high heat resistance and high reliability can be obtained.

Figure 8:
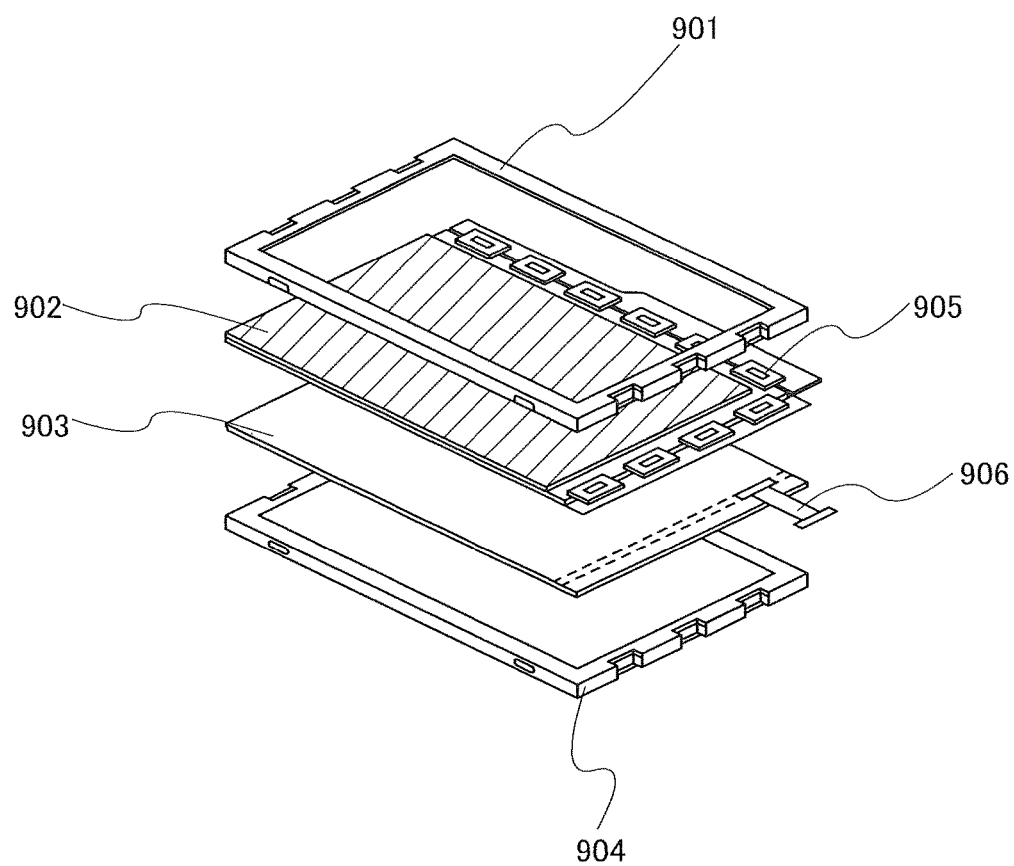
FIG. 8 illustrates a light source device.

FIG. 8 illustrates an example of a liquid crystal display device using the light-emitting element containing the organic compound of one embodiment of the present invention for a backlight. The liquid crystal display device illustrated in FIG. 8 includes a housing 901, a liquid crystal layer 902, a backlight unit 903, and a housing 904. The liquid crystal layer 902 is connected to a driver IC 905. The light-emitting element containing the organic compound of one embodiment of the present invention is used for the backlight unit 903, to which current is supplied through a terminal 906.

Figure 9:
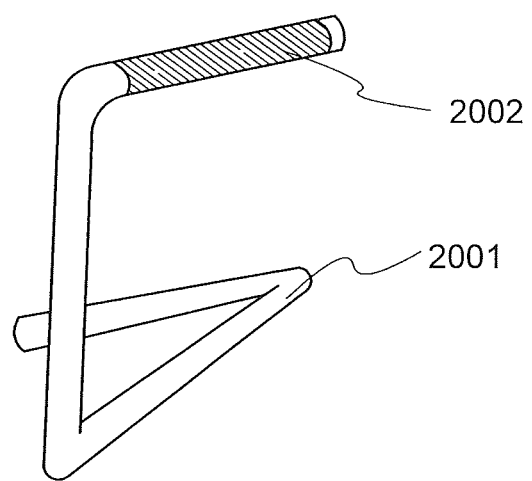
FIG. 9 illustrates a lighting device.

The light-emitting element containing the organic compound of one embodiment of the present invention is used for the backlight of the liquid crystal display device; thus, the backlight can have reduced power consumption. In addition, the use of the light-emitting element described in Embodiment 1 enables manufacture of a planar-emission lighting device and further a larger-area planar-emission lighting device; therefore, the backlight can be a larger-area backlight, and the liquid crystal display device can also be a larger-area device. Furthermore, the light-emitting device including the light-emitting element described in Embodiment 2 can be thinner than a conventional one; accordingly, the display device can also be thinner:

FIG. 9 illustrates an example in which the light-emitting element containing the organic compound of one embodiment of the present invention is used for a table lamp which is a lighting device. The table lamp illustrated in FIG. 9 includes a housing 2001 and a light source 2002, and the lighting device described in Embodiment 3 is used for the light source 2002.

Figure 10:
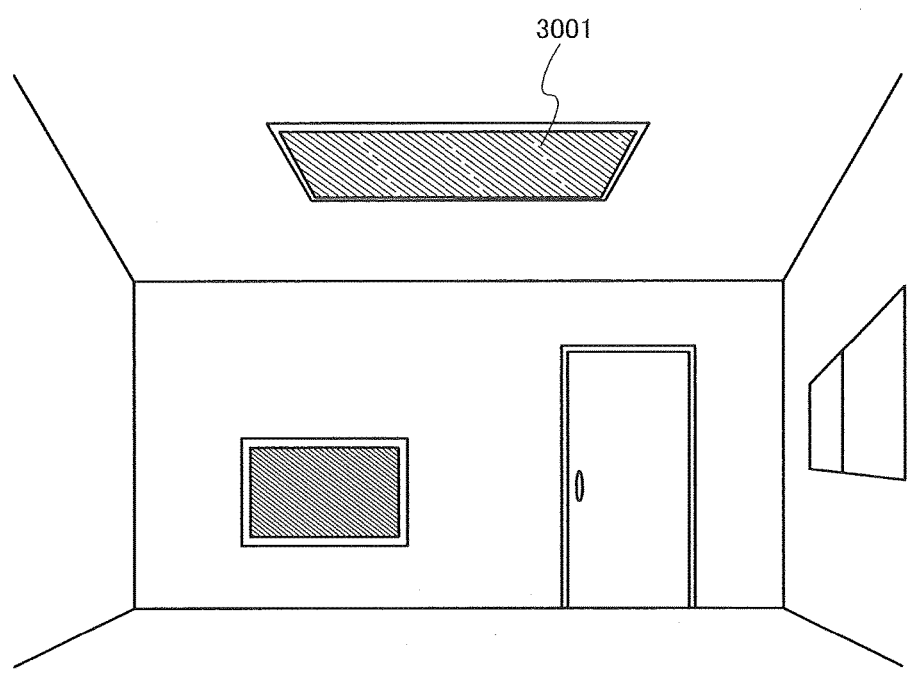
FIG. 10 illustrates a lighting device.

FIG. 10 illustrates an example in which the light-emitting element containing the organic compound of one embodiment of the present invention is used for an indoor lighting device 3001. Since the light-emitting element containing the organic compound of one embodiment of the present invention has high heat resistance, the lighting device can have high heat resistance. Furthermore, since the light-emitting element containing the organic compound of one embodiment of the present invention can have a large area, the light-emitting element can be used for a large-area lighting device. Furthermore, since the light-emitting element containing the organic compound of one embodiment of the present invention is thin, the light-emitting element can be used for a lighting device having a reduced thickness.

Figure 11:
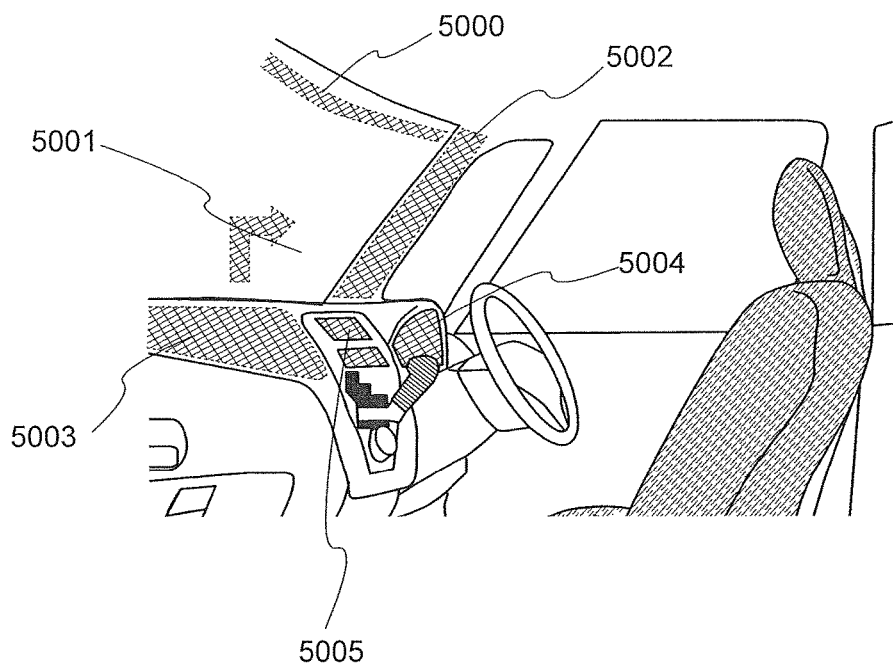
FIG. 11 illustrates in-vehicle display devices and lighting devices.

The light-emitting element containing the organic compound of one embodiment of the present invention can also be used for an automobile windshield or an automobile dashboard. FIG. 11 illustrates one mode in which the light-emitting element described in Embodiment 1 is used for an automobile windshield and an automobile dashboard. Display regions 5000 to 5005 each include the light-emitting element containing the organic compound of one embodiment of the present invention.

The display region 5000 and the display region 5001 are display devices provided in the automobile windshield in which the light-emitting elements each containing the organic compound of one embodiment of the present invention are incorporated. The light-emitting elements each containing the organic compound of one embodiment of the present invention can be formed into what is called a see-through display device, through which the opposite side can be seen, by including a first electrode and a second electrode formed of electrodes having a light-transmitting property. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device provided in a pillar portion in which the light-emitting elements each containing the organic compound of one embodiment of the present invention are incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel level, a gearshift state, and air-condition setting. The content or layout of the display can be freely changed by a user as appropriate. Note that such information can also be shown by the display regions 5000 to 5003. The display regions 5000 to 5005 can also be used as lighting devices.

The light-emitting element containing the organic compound of one embodiment of the present invention has high heat resistance. Accordingly, the light-emitting element containing the organic compound of one embodiment of the present invention can be suitably used for an in-vehicle light-emitting device or lighting device which is placed in a very high-temperature environment in midsummer or the like.

Figure 12A:
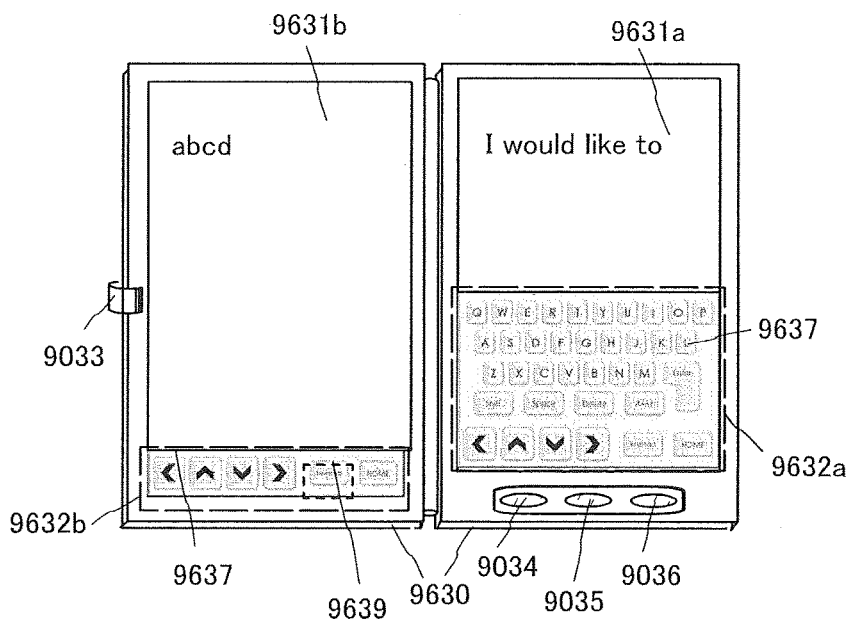
FIGS. 12A to 12C illustrate an electronic device.
Figure 12B:
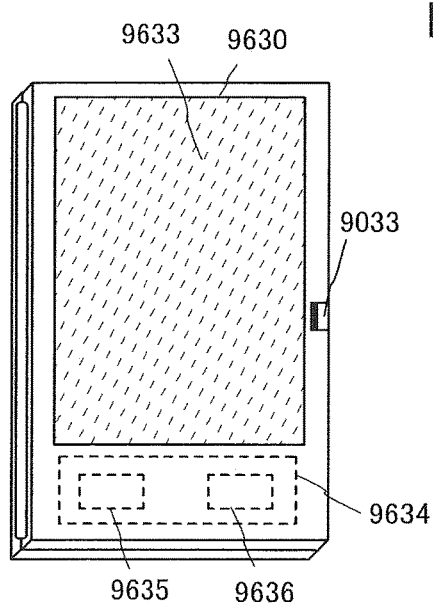

FIGS. 12A and 12B illustrate an example of a foldable tablet terminal. FIG. 12A illustrates the tablet terminal which is unfolded. The tablet terminal includes a housing 9630, a display portion 9631a, a display portion 9631b, a display mode switch 9034, a power switch 9035, a power-saving mode switch 9036, and a clasp 9033. Note that in the tablet terminal, one or both of the display portion 9631a and the display portion 9631b is/are formed using a light-emitting device which includes the light-emitting element containing the organic compound of one embodiment of the present invention.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard can be displayed on the entire region of the display portion 9631a so that the display portion 9631a is used as a touchscreen, and the display portion 9631b can be used as a display screen.

Like the display portion 9631a, part of the display portion 9631b can be a touchscreen region 9632b. When a switching button 9639 for showing/hiding a keyboard on the touchscreen is touched with a finger, a stylus, or the like, the keyboard can be displayed on the display portion 9631b.

Touch input can be performed in the touchscreen region 9632a and the touchscreen region 9632b at the same time.

The display mode switch 9034 can switch the display between portrait mode, landscape mode, and the like, and between monochrome display and color display, for example. The power-saving mode switch 9036 can control display luminance in accordance with the amount of external light in use of the tablet terminal sensed by an optical sensor incorporated in the tablet terminal. Another sensing device including a sensor such as a gyroscope or an acceleration sensor for sensing inclination may be incorporated in the tablet terminal, in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different, display quality. For example, higher definition images may be displayed on one of the display portions 9631a and 9631b.

FIG. 12B illustrates the tablet terminal which is folded. The tablet terminal in this embodiment includes the housing 9630, a solar cell 9633, a charge and discharge control circuit 9634, a battery 9635, and a DCDC converter 9636. In FIG. 12B, a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-twin use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that a structure in which the solar cell 9633 is provided on one or both surfaces of the housing 9630 is preferable because the battery 9635 can be charged efficiently.

Figure 12C:
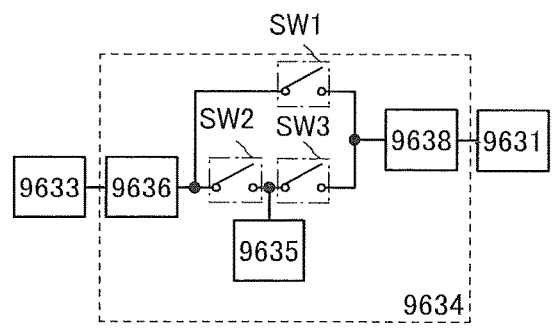

The structure and operation of the charge and discharge control circuit 9634 illustrated in FIG. 12B will be described with reference to a block diagram of FIG. 12C. FIG. 12C illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 12A to 12C as long as the display portion 9631 is included.

Example 1

Synthesis Example 1

In this example, a method for synthesizing 2,2'-(pyridine-2,6-diyl)bis[4-(2-naphthyl)-6-phenylpyrimidine] (abbreviation: 2,6(N-PPm)2Py), which is represented by the structural formula (100), will be described. The structure of 2,6(N-PPm)2Py is shown below.

[Chemical Formula 17]

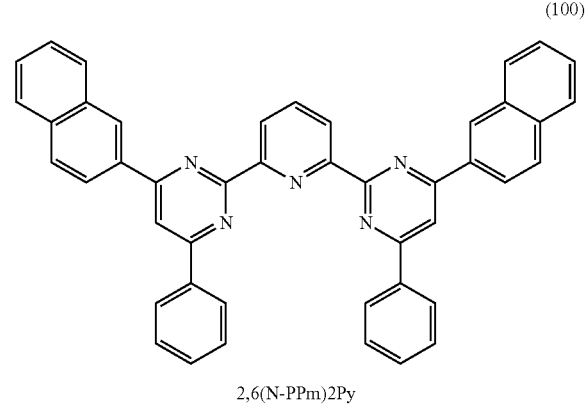

2,6(N-PPm)2Py (100)

Step 1: Synthesis of 2,6-pyridinedicarboxamidine dihydrochloride

First, 5.0 g (39 mmol) of 2,6-pyridinedicarbonitrile and 75 mL of methanol (dehydrated) were put into a 300-mL three-neck flask. Then, 194 mg (3.6 mmol) of sodium methoxide was added to this mixture, and the mixture was stirred under a nitrogen stream at room temperature for 24 hours. After a predetermined time had elapsed, 4.1 g (77 mmol) of ammonium chloride was added to the mixture, and the mixture was stirred under a nitrogen stream at room temperature for 24 hours. After the reaction, ethyl acetate was added to the reaction mixture, and the mixture was irradiated with ultrasonic waves and crushed into pieces, and then suction filtered to give 8.6 g of a white solid which was a target substance in a yield of 93%. The obtained white solid was identified as 2,6-pyridinedicarboxamidine dihydrochloride by nuclear magnetic resonance (NMR) spectroscopy. The reaction scheme of the step 1 is illustrated in (a-1) below.

[Chemical Formula 18]

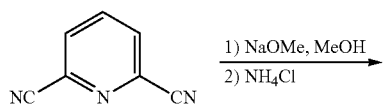

(a-1)

-continued

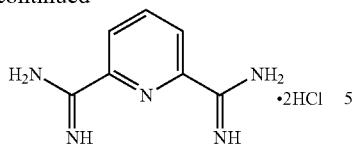

Step 2: Synthesis of
3-(2-naphthyl)-1-phenyl-2-propen-1-one

First, 10.0 g (64 mmol) of 2-naphthoaldehyde, 300 mL of ethanol, and 30 mL of a 3M aqueous solution of sodium hydroxide were put into a 500-mL three-neck flask. Then, 7.7 g (64 mmol) of acetophenone was added dropwise to this mixture, and the mixture was stirred under a nitrogen stream at room temperature for 72 hours to cause a reaction. After the reaction, the reaction mixture was suction filtered to give a solid. The solid was washed with ethanol to give 12.8 g of a yellow solid in a yield of 77%. The obtained yellow solid was identified as 3-(2-naphthyl)-1-phenyl-2-propen-1-one by nuclear magnetic resonance (NMR) spectroscopy. The reaction scheme of the step 2 is illustrated in (b-1) below.

(b-1)

[Chemical Formula 19]

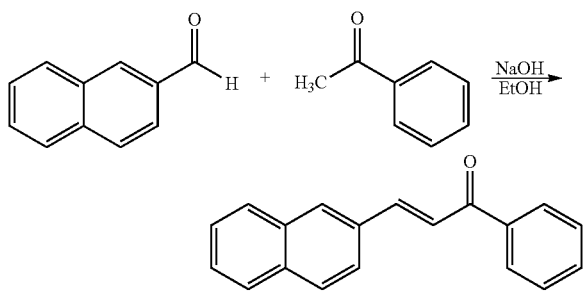

Step 3: Synthesis of 2,2'-(pyridine-2,6-diyl)bis[4-(2-naphthyl)-6-phenylpyrimidine] (abbreviation: 2,6 (N-PPm)2Py)

First, 3.7 g (15.5 mmol) of 2,6-pyridinedicarbonitrile, 8.0 g (31 mmol) of 3-(2-naphthyl)-1-phenyl-2-propen-1-one, 140 mL of ethanol, and 47 mL of water were put into a 1000-mL three-neck flask. Then, 3.7 g (93 mmol) of sodium hydroxide was added to this mixture, and the mixture was heated and refluxed under a nitrogen stream for 23 hours to cause a reaction. After the reaction, water and chloroform were added to the mixture, and the mixture was subjected to extraction. The obtained organic layer was washed with water and a saturated aqueous solution of sodium chloride. Anhydrous magnesium sulfate was added to the organic layer for drying. This mixture was subjected to gravity filtration, and the filtrate was concentrated to give a solid. The solid was purified by silica column chromatography. As the developing solvent, first, dichloromethane, then, a 1:1 dichloromethane-ethyl acetate mixed solvent, and lastly, ethyl acetate were used. A fraction of the obtained target substance was concentrated to give a solid. Ethanol was added to the obtained solid, and the mixture was suction filtered to give a solid. Recrystallization of the obtained solid from a toluene/ethanol mixed solvent was performed to give 0.56 g of a white solid in a yield of 6%. By a train sublimation method, 0.56 g of the obtained solid was purified under a pressure of $7.0 \times 10^{-3}$ Pa at 325° C. for 23 hours. After the sublimation purification, 0.40 g of a white solid which was a target substance was obtained at a collection rate of 71%. The synthesis scheme of the step 3 is illustrated in (c-1) below.

(c-1)

[Chemical Formula 20]

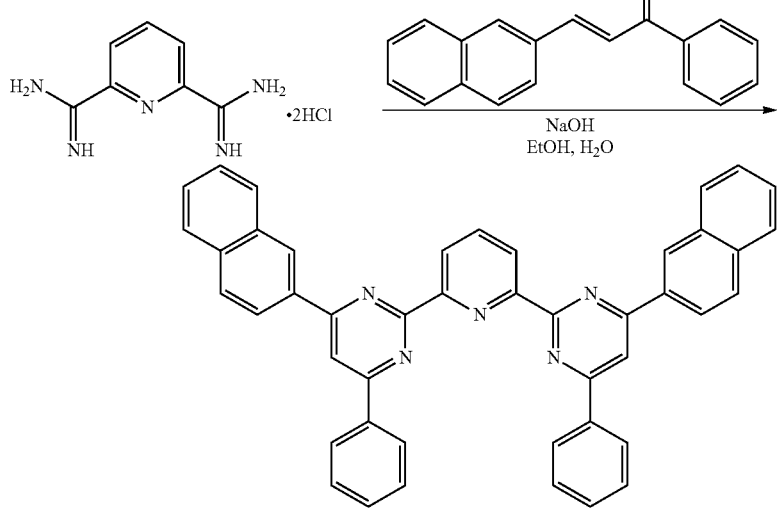

(100) 2,6(N-PPm)2Py

Figure 13A:
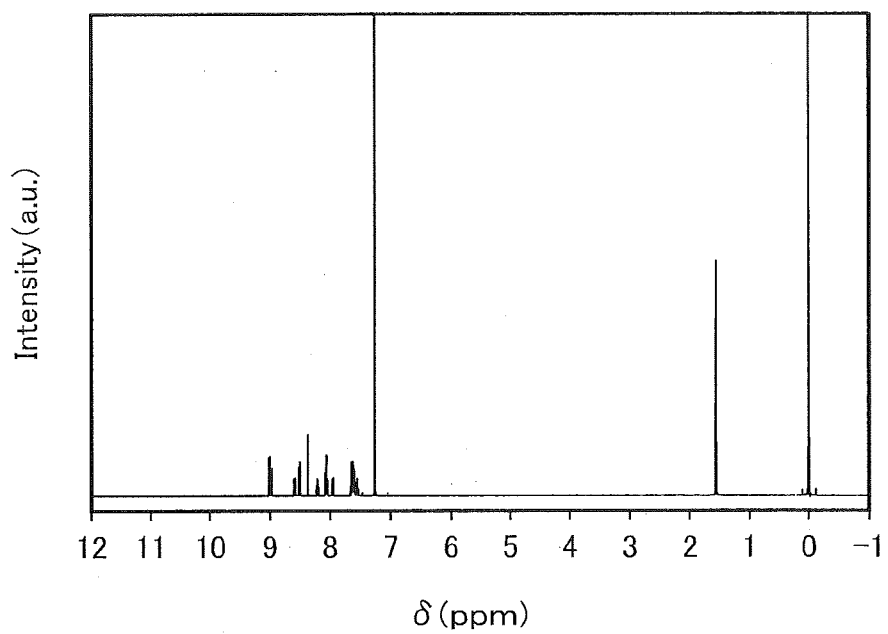
FIGS. 13A and 13B show $^1$H-NMR charts of 2,6(N-PPm)2Py.
Figure 13B:
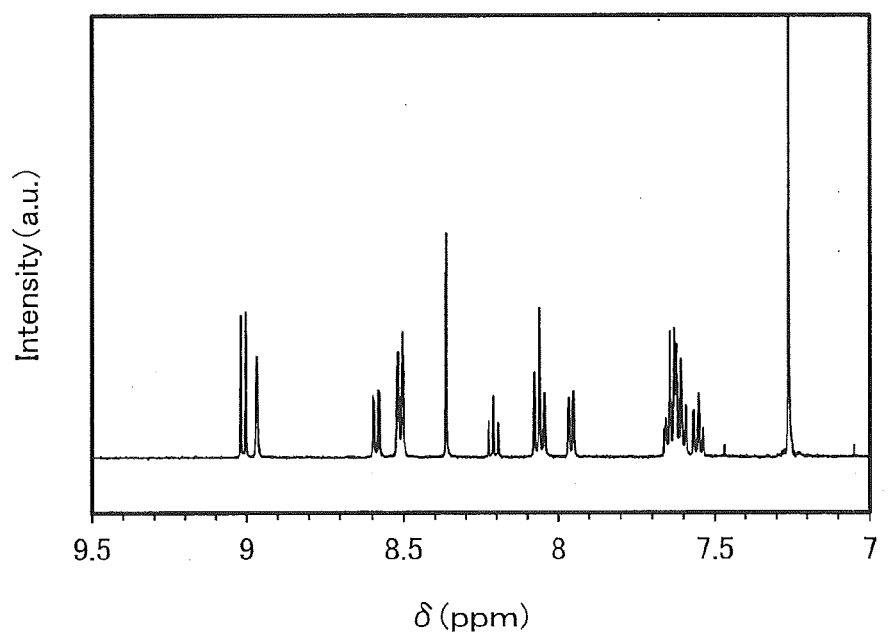

Protons ($^1$H) of the white solid which was obtained through the step 3 described above was measured by nuclear magnetic resonance (NMR) spectroscopy. The obtained values are shown below. FIGS. 13A and 13B show the $^1$H-NMR charts. FIG. 13B is a chart where the range of from 7 ppm to 9.5 ppm in FIG. 13A is enlarged. These results reveal that 2,6(N-PPm)2Py, which is the organic compound of one embodiment of the present invention represented by the structural formula (100), was obtained in this synthesis example.

$^1$H-NMR δ (CDCl$_3$): 7.54 (t, 2H), 7.59-7.66 (m, 8H), 7.96 (d, 2H), 8.06 (t, 4H), 8.21 (t, 1H), 8.36 (s, 2H), 8.51 (d, 4H), 8.59 (d, 2H), 8.97 (s, 2H), 9.01 (d, 2H).

Thermogravimetry-differential thermal analysis (TG-DTA) of 2,6(N-PPm)2Py was performed. A high vacuum differential type differential thermal balance (TG/DTA 2410SA, manufactured by Broker AXS K.K.) was used for the measurement. The measurement was carried out under a nitrogen stream (a flow rate of 200 mL/min) and a normal pressure at a temperature rising rate of 10° C./min. From the relationship between weight and temperature (thermogravimetry), it has been found that no weight loss is observed at temperatures up to 500° C., which is indicative of high heat resistance.

Next, 2,6(N-PPm)2Py obtained was analyzed by liquid chromatography mass spectrometry (LC/MS). In the LC/MS analysis, liquid chromatography (LC) separation was carried out with ACQUITY UPLC (registered trademark) (manufactured by Waters Corporation) and mass spectrometry (MS) analysis was carried out with Xevo G2 Tof MS (manufactured by Waters Corporation). ACQUITY UPLC (registered trademark) BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. Furthermore, a sample was prepared in such a manner that 2,6(N-PPm)2Py was dissolved in chloroform at a given concentration and the solution was diluted with acetonitrile. The injection amount was 5.0 μL.

In the LC separation, a gradient method in which the composition of mobile phases is changed was employed. The ratio of Mobile Phase A to Mobile Phase B was 60:40 for 0 to 1 minute after the start of the measurement, and then the composition was changed such that the ratio of Mobile Phase A to Mobile Phase B after 10 minutes from the start of the measurement was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 640.25 which underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIG. 14.

Figure 14:
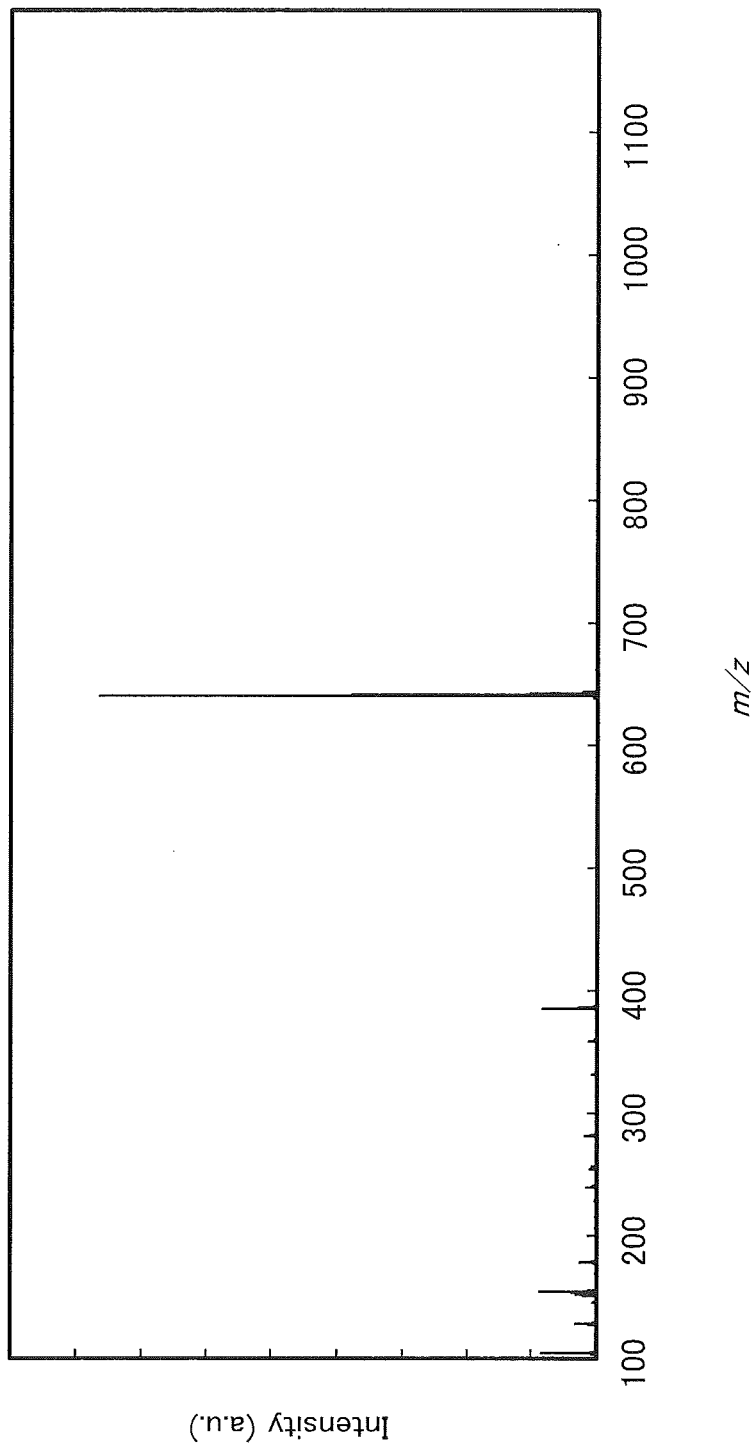
FIG. 14 shows results of LC/MS analysis of 2,6(N-PPm)2Py.

FIG. 14 shows that product ions of 2,6(N-PPm)2Py are mainly detected around z=385, 154, and 104. The results in FIG. 14 show characteristics derived from 2,6(N-PPm)2Py and therefore can be regarded as important data for identifying 2,6(N-PPm)2Py contained in a mixture.

It can be presumed that the product ion around m/z=385 is a cation in a state where two naphthalenes were eliminated from 2,6(N-PPm)2Py and includes 2,2'-(pyridine-2,6-diyl)bis(4-phenylpyrimidine). It can also be presumed that the product ion around m/z=154 is a cation in a state where one benzene and one phenylpyrimidine were additionally eliminated and the product ion around m/z=104 is a cation in a state where a pyrimidine ring or a pyridine ring is cleaved. These results suggest that 2,6(N-PPm)2Py includes benzene, naphthalene, phenylpyrimidine, a pyridine ring, and a pyrimidine ring.

Example 2

Synthesis Example 2

In this example, a method for synthesizing 2,2'-(pyridine-2,6-diyl)bis{4-[4-(2-naphthyl)phenyl]-6-phenylpyrimidine} (abbreviation: 2,6(NP-PPm)2Py), which is represented by the structural formula (200), will be described. The structure of 2,6(NP-PPm)2Py is shown below.

[Chemical Formula 21]

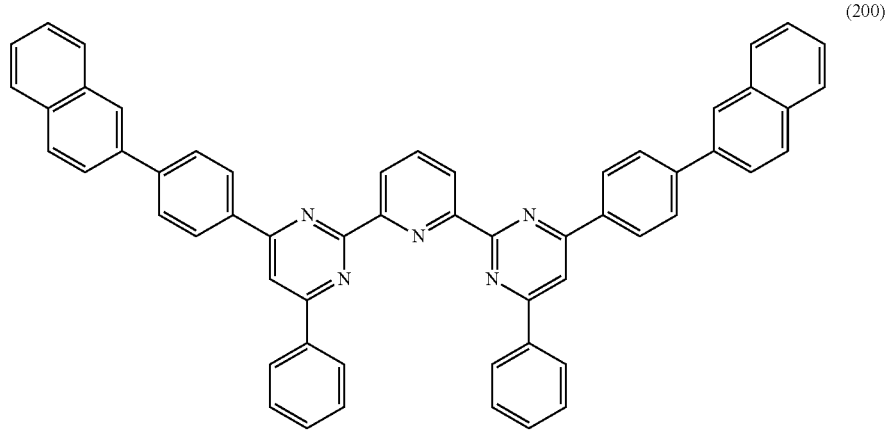

(200)

2,6(NP-PPm)2Py

Step 1: Synthesis of 2,6-pyridinedicarboxamidine dihydrochloride

This step is similar to the step 1 in Synthesis example 1.

Step 2: Synthesis of 4-bromochalcone

First, 13.0 g (70.0 mmol) of 4-bromobenzaldehyde, 8.4 g (70.0 mmol) of acetophenone, 100 mL of ethanol, and 30 mL of a 3M aqueous solution of sodium hydroxide were put into a 300-mL three-neck flask, and the mixture was stirred under a nitrogen stream at room temperature for 17 hours. After the reaction, the reaction mixture was suction filtered to give a solid. The solid was washed with ethanol to give 17.5 g of a yellow solid in a yield of 87%. The obtained yellow solid was identified as 4-bromochalcone by nuclear magnetic resonance (NMR) spectroscopy. The synthesis scheme of the step 2 is illustrated in (b-2) below.

[Chemical Formula 22]

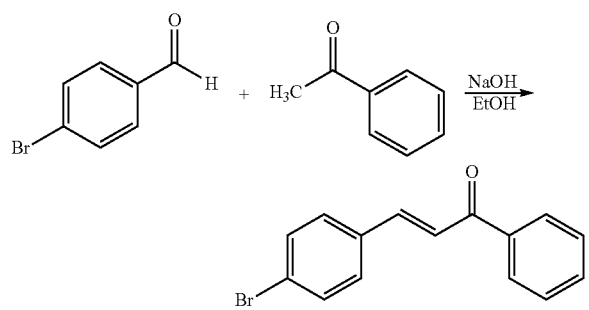

(b-2)

Step 3: Synthesis of 2,2'-(pyridine-2,6-diyl)bis[4-(4-bromophenyl)-6-phenylpyrimidine]

First, 5.0 g (21.2 mmol) of 2,6-pyridinedicarboxamidine, 17.5 g (60.9 mmol) of 4-bromochalcone, 175 mL of ethanol, and 58 mL of water were put into a 500-mL three-neck flask. Then, 5.1 g (127 mmol) of sodium hydroxide was added to this mixture, and the mixture was heated and refluxed under a nitrogen stream for 11 hours to cause a reaction. After the reaction, water and chloroform were added to the reacted solution, and the mixture was subjected to extraction. The obtained organic layer was washed with water and a saturated aqueous solution of sodium chloride. Anhydrous magnesium sulfate was added to the organic layer for drying. This mixture was subjected to gravity filtration, and the filtrate was concentrated to give an oily substance. The obtained oily substance was purified by silica column chromatography. As the developing solvent, first, dichloromethane, and then, a 4:1 dichloromethane-ethyl acetate mixed solvent were used. A fraction of the obtained target substance was concentrated to give a solid. Ethyl acetate was added to the obtained solid, and the mixture was irradiated with ultrasonic waves and crushed into pieces, and then suction filtered to give 4.4 g of a white solid in a yield of 29%. The obtained white solid was identified as 2,2'-(pyridine-2,6-diyl)bis[4-(4-bromophenyl)-6-phenylpyrimidine] by nuclear magnetic resonance (NMR) spectroscopy. The synthesis scheme of the step 3 is illustrated in (c-2) below.

[Chemical Formula 23]

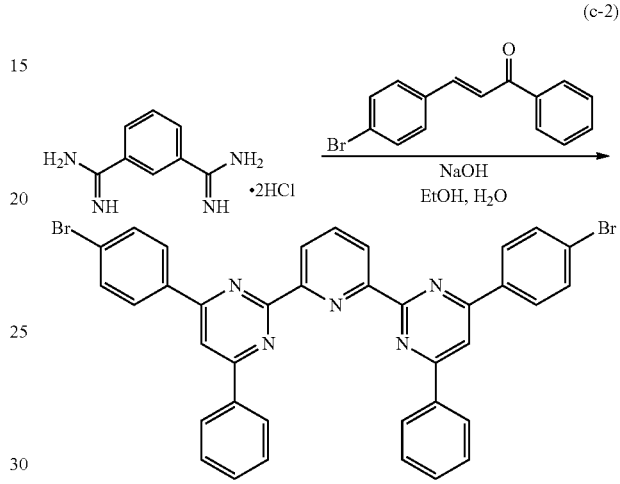

(c-2)

<Step 4: Synthesis of 2,2'-(pyridine-2,6-diyl)bis{4-[4-(2-naphthyl)phenyl]-6-phenylpyrimidine} (abbreviation: 2,6(NP-PPm)2Py)

First, 2.4 g (3.5 mmol) of 2,2'-(pyridine-2,6-diyl)bis[4-(4-bromophenyl)-6-phenylpyrimidine], 1.5 g (8.8 mmol) of 2-naphthaleneboronic acid, 1.9 g (8.8 mmol) of tripotassium phosphate, 0.086 g (0.21 mmol) of 2-dicyclohexylphosphino-2',6'-dimethoxybiphenyl (S-Phos), and 50 mL of toluene were put into a 300-mL three-neck flask, and the atmosphere in the flask was replaced with nitrogen. The mixture was stirred to be degassed while the pressure in the flask was reduced. After the degassing, the atmosphere in the flask was replaced with nitrogen, 0.024 g (0.11 mmol) of palladium(II) acetate was added, and the mixture was stirred under a nitrogen stream at 100° C. for 16 hours to cause a reaction. The obtained reaction mixture was suction filtered to give a solid. The obtained solid was washed with water and ethanol. The obtained solid was dissolved in toluene by heating, and the toluene solution was filtered through a filter aid in which Celite (produced by Wako Pure Chemical Industries, Ltd., Catalog No. 531-16855, the same shall apply hereinafter), alumina, and Celite were stacked in this order. The obtained filtrate was concentrated to obtain a solid. The obtained solid was recrystallized with toluene to give 2.1 g of a white solid in a yield of 75%. By a train sublimation method, 1.9 g of the obtained solid was purified under a pressure of $1.6 \times 10^{-3}$ Pa at 415° C. for 14.5 hours. After the sublimation purification, 1.7 g of a white solid which was a target substance was obtained at a collection rate of 86%. The synthesis scheme of the step 4 is illustrated in (d-2) below.

[Chemical Formula 24]

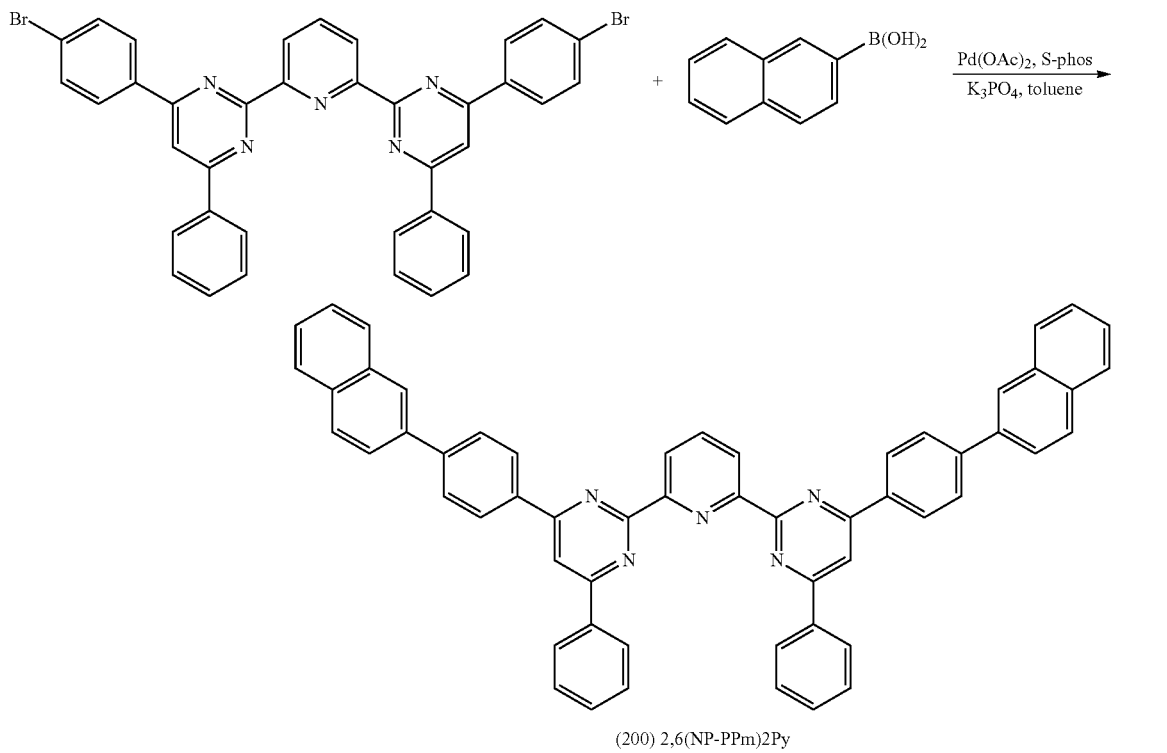

(d-2)

(200) 2,6(NP-PPm)2Py

Figure 15A:
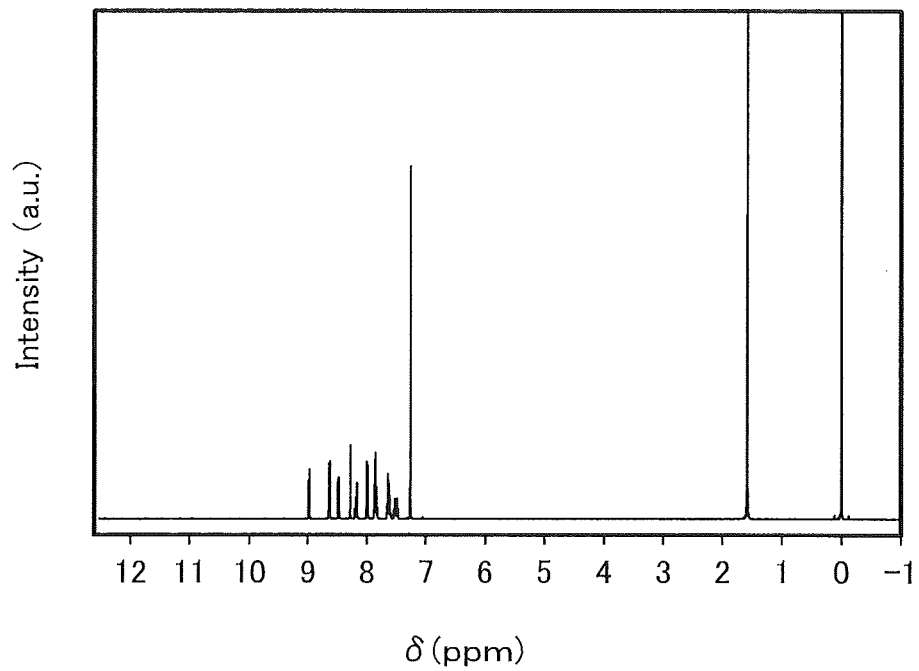
FIGS. 15A and 15B show $^1$H-NMR charts of 2,6(NP-PPm)2Py.
Figure 15B:
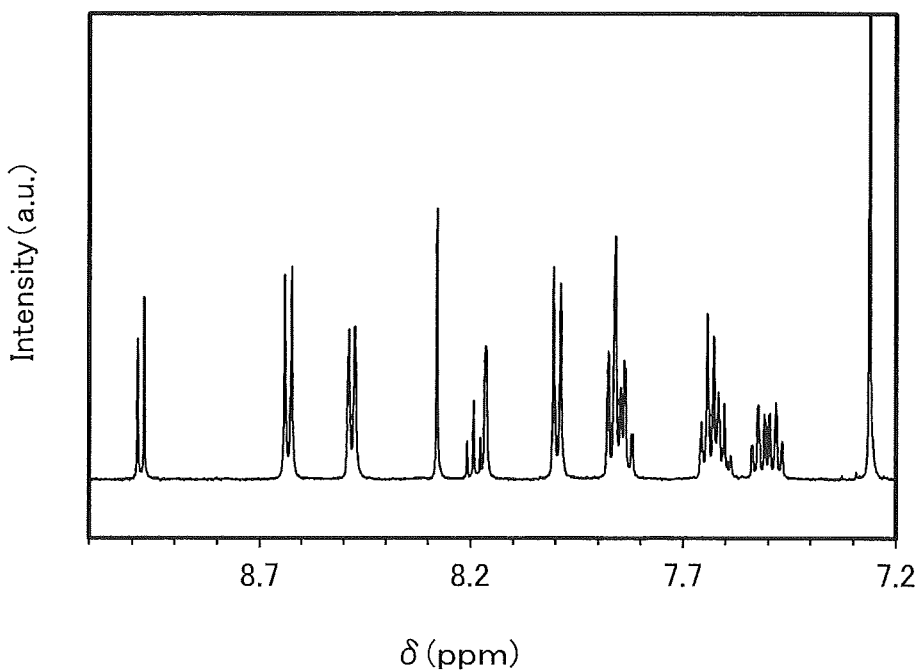

Protons ($^1$H) of the white solid which was obtained through the step 4 described above was measured by nuclear magnetic resonance (NMR) spectroscopy. The obtained values are shown below. FIGS. 15A and 15B show the $^1$H-NMR charts. FIG. 15B is a chart where the range of from 7.2 ppm to 9.1 ppm on the horizontal axis in FIG. 15A is enlarged. These results reveal that 2,6(NP-PPm)2Py, which is the organic compound of one embodiment of the present invention represented by the structural formula (200), was obtained in this synthesis example.

$^1$H-NMR δ (CDCl$_3$): 7.47-7.54 (m, 4H), 7.59-7.66 (m, 6H), 7.82-7.88 (m, 8H), 8.00 (d, 4H), 8.16-8.21 (m, 3H), 8.30 (s, 2H), 8.48 (d, 4H), 8.63 (d, 4H), 8.98 (d, 2H).

Thermogravimetry-differential thermal analysis (TG-DTA) of 2,6(NP-PPm)2Py obtained was performed. A high vacuum differential type differential thermal balance (TG/DTA 2410SA, manufactured by Bruker AXS K.K.) was used for the measurement. The measurement was carried out under a nitrogen stream (a flow rate of 200 mL/min) and a normal pressure at a temperature rising rate of 10° C./min. From the relationship between weight and temperature (thermogravimetry), it has been found that no weight loss is observed at temperatures up to 500° C., which is indicative of high heat resistance.

In the analysis by LC/MS, liquid chromatography (LC) separation was carried out with ACQUITY UPLC (registered trademark) (manufactured by Waters Corporation) and mass spectrometry (MS) analysis was carried out with Xevo G2 Tof MS (manufactured by Waters Corporation). ACQUITY UPLC (registered trademark) BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. Furthermore, a sample was prepared in such a manner that 2,6(NP-PPm)2Py was dissolved in chloroform at a given concentration and the solution was diluted with acetonitrile. The injection amount was 5.0 μL.

In the LC separation, a gradient method in which the composition of mobile phases is changed was employed. The ratio of Mobile Phase A to Mobile Phase B was 65:35 for 0 to 1 minute after the start of the measurement, and then the composition was changed such that the ratio of Mobile Phase A to Mobile Phase B after 10 minutes from the start of the measurement was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 792.31 which underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIG. 16.

Figure 16:
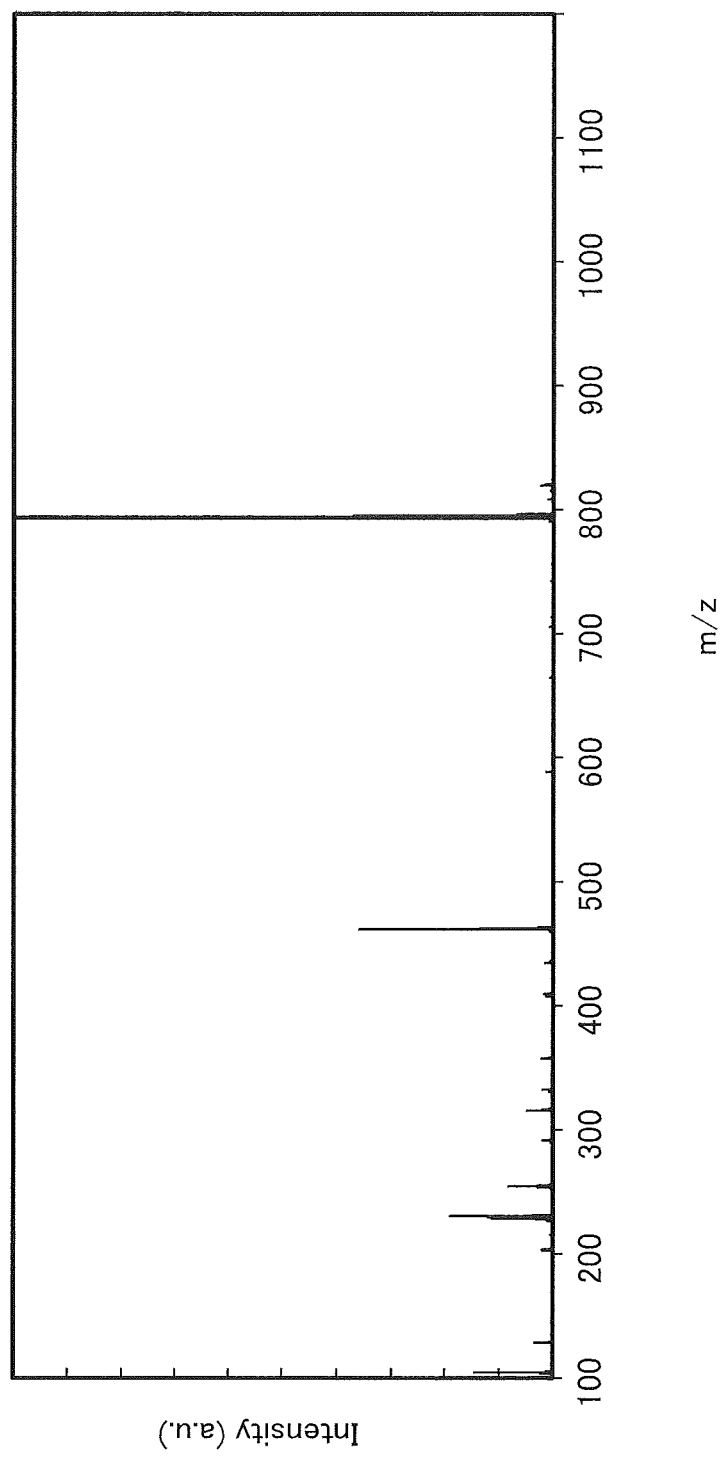
FIG. 16 shows results of LC/MS analysis of 2,6(NP-PPm)2Py.

FIG. 16 shows that product ions of 2,6(NP-PPm)2Py are mainly detected around m/z=461. The results in FIG. 16 show characteristics derived from 2,6(NP-PPm)2Py and therefore can be regarded as important data for identifying 2,6(NP-PPm)2Py contained in a mixture.

It can be presumed that the product ion around m/z=461 is a cation in a state where naphthalene and phenylnaphthalene were eliminated from 2,6(NP-PPm)2Py and includes 2,2'-(pyridine-2,6-diyl)(4-phenylpyrimidine)(4,6-diphenylpyrimidine). These results suggest that 2,6(NP-PPm)2Py includes naphthalene and phenylnaphthalene.

Example 3

Synthesis Example 3

In this example, a method for synthesizing 2,2'-[4-(1-pyrenyl)pyridine-2,6-diyl]bis(4,6-diphenylpyrimidine) (abbreviation: Pm-2,6(P2Pm)2Py), which is represented by the structural formula (300), will be described. The structure of Pm-2,6(P2Pm)2Py is shown below.

[Chemical Formula 25]

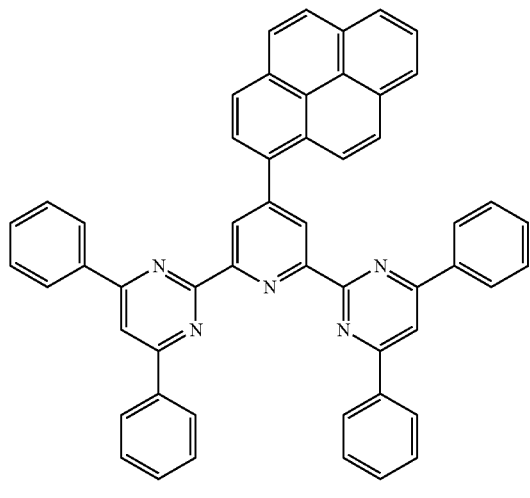

Pm-2,6(P2Pm)2Py
(300)

Step 1: Synthesis of 4-chloro-2,6-pyridinedicarboxamidine dihydrochloride

First, 15.0 g (91.7 mmol) of 4-chloro-2,6-pyridinedicarbonitrile and 200 mL of methanol (dehydrated) were put into a 500-mL three-neck flask. Then, 456 mg (8.4 mmol) of sodium methoxide was added to this mixture, and the mixture was stirred under a nitrogen stream at room temperature for 16 hours. After a predetermined time had elapsed, 9.8 g (183 mmol) of ammonium chloride was added to the mixture, and the mixture was stirred under a nitrogen stream at room temperature for two days. After the reaction, the reacted mixture was concentrated, ethyl acetate was added, and the mixture was irradiated with ultrasonic waves and crushed into pieces, and then suction filtered to give 18.7 g of a white solid in a yield of 75%. The obtained white solid was identified as 4-chloro-2,6-pyridinedicarboxamidine dihydrochloride by nuclear magnetic resonance (NMR) spectroscopy. The synthesis scheme of the step 1 is illustrated in (a-3) below.

[Chemical Formula 26]

(a-3)

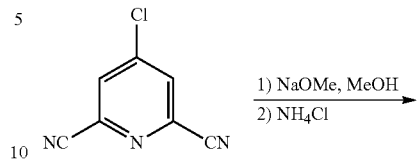

Step 2: Synthesis of 2,2'-(4-chloro-pyridine-2,6-diyl)bis(4,6-diphenylpyrimidine)>

First, 10.0 g (37.0 mmol) of 4-chloro-2,6-pyridinedicarboxamidine dihydrochloride, 23.1 g (110 mmol) of calcone, 305 mL of ethanol, and 87 mL of water were put into a 1000-mL three-neck flask. Then, 8.9 g (222 mmol) of sodium hydroxide was added to this mixture, and the mixture was heated and refluxed under a nitrogen stream for 18 hours. After the reaction, water and chloroform were added to the reacted solution, and the mixture was subjected to extraction. The obtained organic layer was washed with water and a saturated aqueous solution of sodium chloride. Anhydrous magnesium sulfate was added to the organic layer for drying. This mixture was subjected to gravity filtration, and the filtrate was concentrated to give an oily substance. The obtained oily substance was purified by silica column chromatography. As the developing solvent, first, dichloromethane, and then, a 4:1 dichloromethane-ethyl acetate mixed solvent were used. A fraction of the obtained target substance was concentrated to give a solid. Ethanol was added to the obtained solid, and the mixture was irradiated with ultrasonic waves and crushed into pieces, and then suction filtered to give 1.6 g of a white solid in a yield of 8%. The obtained white solid was identified as 2,2'(4-chloro-pyridine-2,6-diyl)bis(4,6-diphenylpyrimidine) by nuclear magnetic resonance (NMR) spectroscopy. The synthesis scheme of the step 2 is illustrated in (b-3) below.

[Chemical Formula 27]

(b-3)

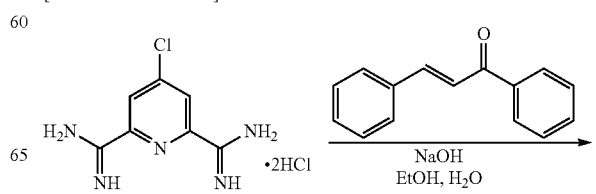

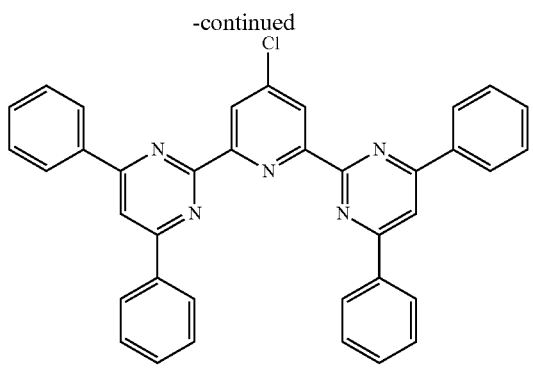

Step 3: 2,2'-[4-(1-pyrenyl)pyridine-2,6-diyl]bis(4,6-diphenylpyrimidine) (abbreviation: Pm-2,6(P2Pm)2Py)

First, 1.2 g (2.1 mmol) of 2,2'-(4-chloro-pyridine-2,6-diyl)bis(4,6-diphenylpyrimidine), 0.617 g (2.5 mmol) of 1-pyreneboronic acid, 1.1 g (5.2 mmol) of tripotassium phosphate, 0.052 g (0.125 mmol) of 2-dicyclohexylphosphino-2',6'-dimethoxybiphenyl (S-Phos), and 100 mL of toluene were put into a reaction container, and the atmosphere in the reaction container was replaced with nitrogen. The mixture was stirred to be degassed while the pressure in the reaction container was reduced. After the degassing, the atmosphere in the reaction container was replaced with nitrogen, 0.028 g (0.126 mmol) of palladium(II) acetate was added, and the mixture was stirred under a nitrogen stream at 100° C. for 14 hours. Toluene was added to the reacted mixture, and the toluene solution was filtered through a filter aid in which Celite, alumina, and Celite were stacked in this order. Furthermore, the filter aid was washed with 2 L of a 9:1 toluene-ethyl acetate mixed solvent. The obtained filtrate was concentrated to obtain a solid. The obtained solid was purified by silica column chromatography. As the developing solvent, a 10:1 toluene-ethyl acetate mixed solvent was used. A fraction of the obtained target substance was concentrated to give a solid. The obtained solid was recrystallized with toluene to give 0.47 g of a pale yellow solid in a yield of 30%. The solid obtained through the above step and a solid obtained through a similar procedure were mixed to give 0.71 g of the mixture. By a train sublimation method, the mixture was purified under a pressure of $4.7 \times 10^{-3}$ Pa at 350° C. for 7 hours. After the sublimation purification, 0.47 g of a pale yellow solid which was a target substance was obtained at a collection rate of 66%. Then, 0.45 g of the obtained solid was subjected to sublimation purification again under a pressure of $3.5 \times 10^{-2}$ Pa while being heated at 365° C. for 7 hours. After the sublimation purification, 0.32 g of the pale yellow solid which was the target substance was obtained at a collection rate of 71%. The synthesis scheme of the step 3 is illustrated in (c-3) below.

[Chemical Formula 28]

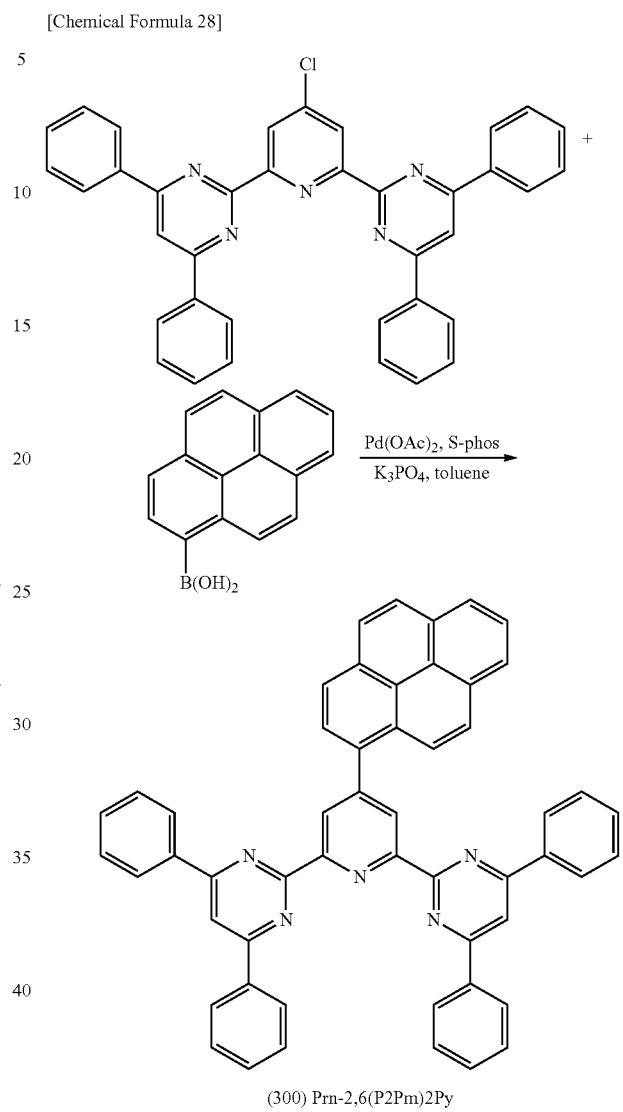

(300) Prn-2,6(P2Pm)2Py

Figure 17A:
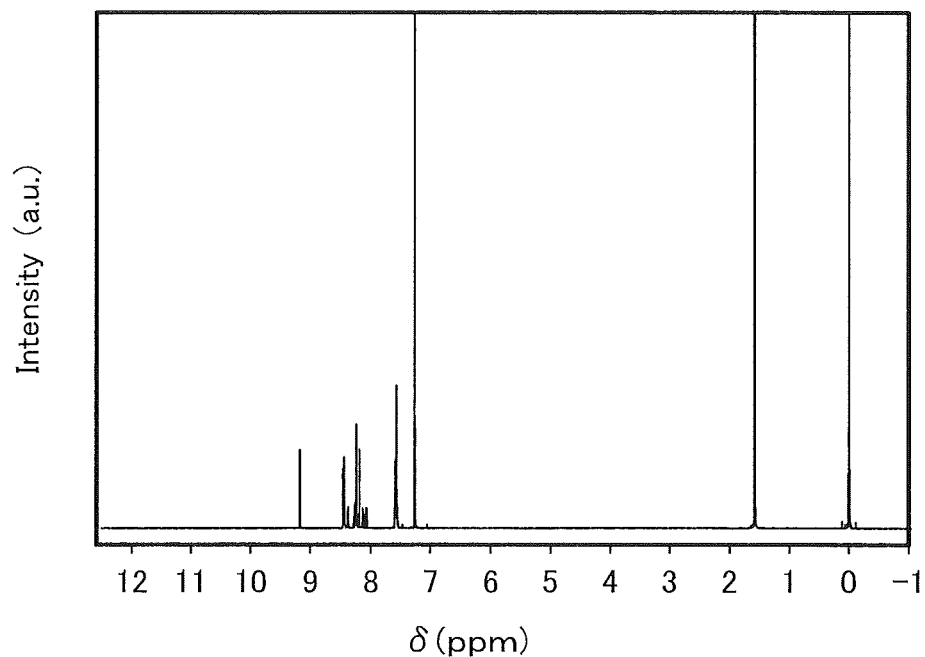
FIGS. 17A and 17B show $^1$H-NMR charts of Prn-2,6(P2Pm)2Py.
Figure 17B:
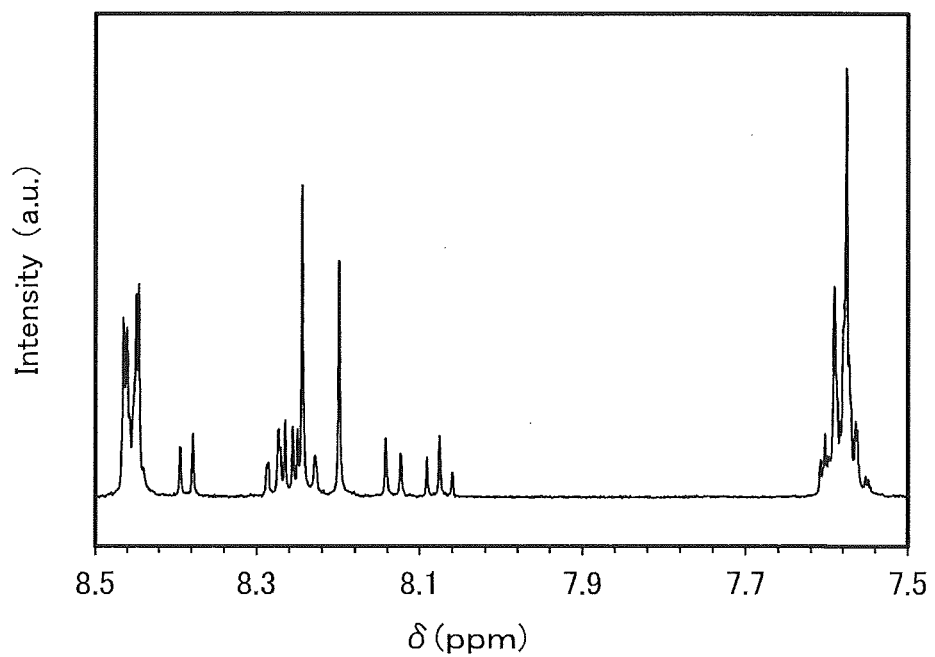

Protons ($^1$H) of the pale yellow solid which was obtained through the step 3 described above was measured by nuclear magnetic resonance (NMR) spectroscopy. The obtained values are shown below. FIGS. 17A and 17B show the $^1$H-NMR charts. FIG. 17B is a chart where the range of from 7.5 ppm to 8.5 ppm on the horizontal axis in FIG. 17A is enlarged. These results reveal that Pm-2,6(P2Pm)2Py, which is the organic compound of one embodiment of the present invention represented by the structural formula (300), was obtained in this synthesis example.

$^1$H-NMR δ (CDCl$_3$): 7.55-7.60 (m, 12H), 8.08 (t, 1H), 8.13 (d, 1H), 8.20 (s, 2H), 8.23-8.27 (m, 6H), 8.39 (d, 1H), 8.45-8.47 (m, 8H), 9.18 (s, 2H).

Thermogravimetry-differential thermal analysis (TG-DTA) of Prn-2,6(P2Pm)2Py obtained was performed. A high vacuum differential type differential thermal balance (TG/DTA 2410SA, manufactured by Bruker AXS K.K.) was used for the measurement. The measurement was carried out under a nitrogen stream (a flow rate of 200 mL/min) and a normal pressure at a temperature rising rate of 10° C./min.

From the relationship between weight and temperature (thermogravimetry), it has been found that no weight loss is observed at temperatures up to 500° C., which is indicative of high heat resistance.

In the analysis by LC/MS, liquid chromatography (LC) separation was carried out with ACQUITY UPLC (registered trademark) (manufactured by Waters Corporation) and mass spectrometry (MS) analysis was carried out with Xevo G2 Tof MS (manufactured by Waters Corporation). ACQUITY UPLC (registered trademark) BEH C8 (2.1×100 mm, 1.7 μm) was used as a colunm for the LC separation, and the column temperature was 40° C. Acetonitrile was used for Mobile Phase A and a 0.1% formic acid aqueous solution was used for Mobile Phase B. Furthermore, a sample was prepared in such a manner that Prn-2,6(P2Pm) 2Py was dissolved in chloroform at a given concentration and the solution was diluted with acetonitrile. The injection amount was 5.0 μL.

In the LC separation, a gradient method in which the composition of mobile phases is changed was employed. The ratio of Mobile Phase A to Mobile Phase B was 70:30 for 0 to 1 minute after the start of the measurement, and then the composition was changed such that the ratio of Mobile Phase A to Mobile Phase B after 10 minutes from the start of the measurement was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 740.28 which underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIG. 18.

Figure 18:
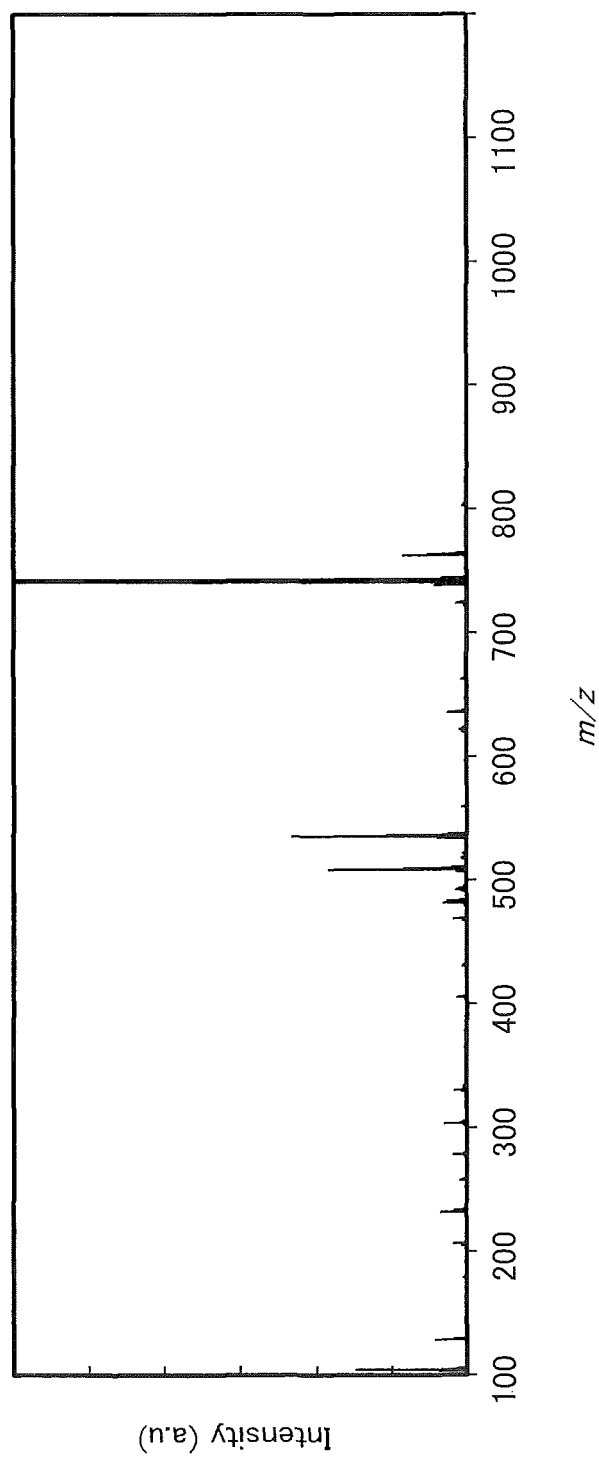
FIG. 18 shows results of LC/MS analysis of Pm-2,6(P2Pm)2Py.

FIG. 18 shows that product ions of Pm-2,6(P2Pm)2Py are mainly detected around m/z=535 and 508. The results in FIG. 18 show characteristics derived from Pm-2,6(P2Pm) 2Py and therefore can be regarded as important data for identifying Pm-2,6(P2Pm)2Py contained in a mixture.

It can be presumed that the product ion around m/z=535 is a cation in a state where one pyrimidine ring in Prn-2,6 (P2Pm)2Py is cleaved, and it can also be presumed that the product ion around m/z=508 is a cation in a state where CN is further eliminated and diphenylpyrimidine is eliminated from Prn-2,6(P2Pm)2Py. These results suggest that Prn-2,6 (P2Pm)2Py includes diphenylpyrimidine.

Example 4

In this example, a light-emitting element 1 containing 2,2'-(pyridine-2,6-diyl)bis[4-(2-naphthyl)-6-phenylpyrimidine] (abbreviation: 2,6(N-PPm)2Py), which is represented by the structural formula (100) and is synthesized in Synthesis example 1, a light-emitting element 2 containing 2,2'-(pyridine-2,6-diyl)bis{4-[4-(2-naphthyl)phenyl]-6-phenylpyrimidine} (abbreviation: 2,6(NP-PPm)2Py), which is represented by the structural formula (200) and is synthesized in Synthesis example 2, and a comparative light-emitting element 1 containing 2,2'-(pyridine-2,6-diyl)bis(4, 6-diphenylpyrimidine) (abbreviation: 2,6(P2Pm)2Py) will be described. Structure formulae of organic compounds used in the light-emitting elements 1 and 2 and the comparative light-emitting element 1 are shown below.

[Chemical Formulae 29]

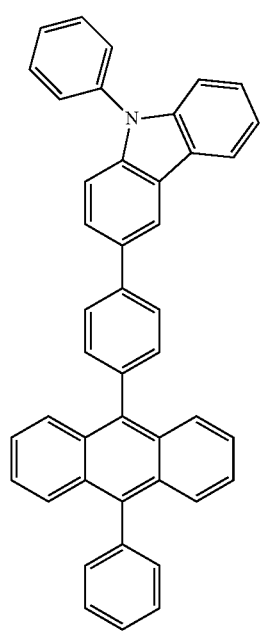

PCzPA
(i)

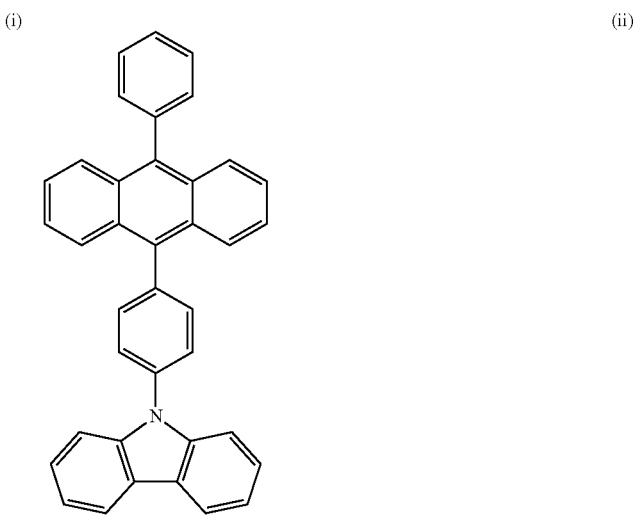

CzPA
(ii)

-continued
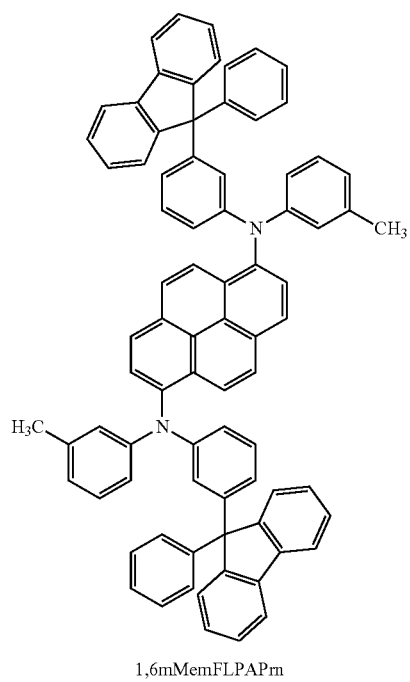
1,6mMemFLPAPrn
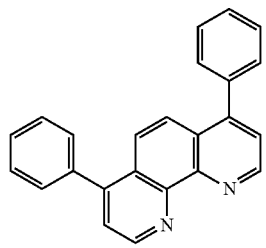
BPhen
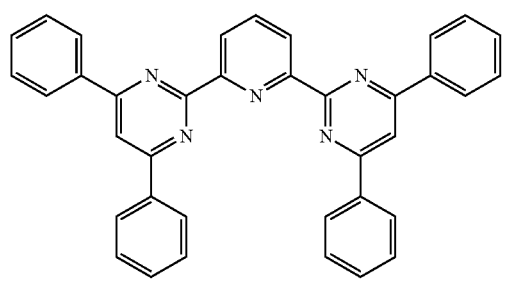
2,6(P2Pm)2Py
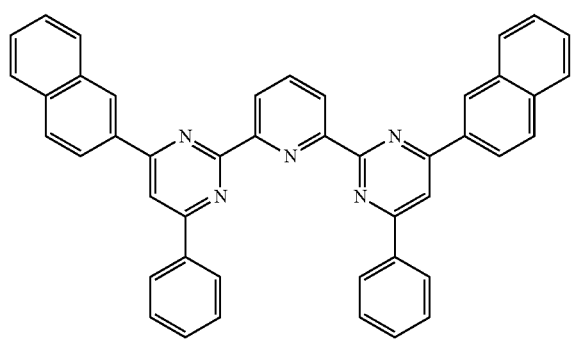
2,6(N-PPm)2Py
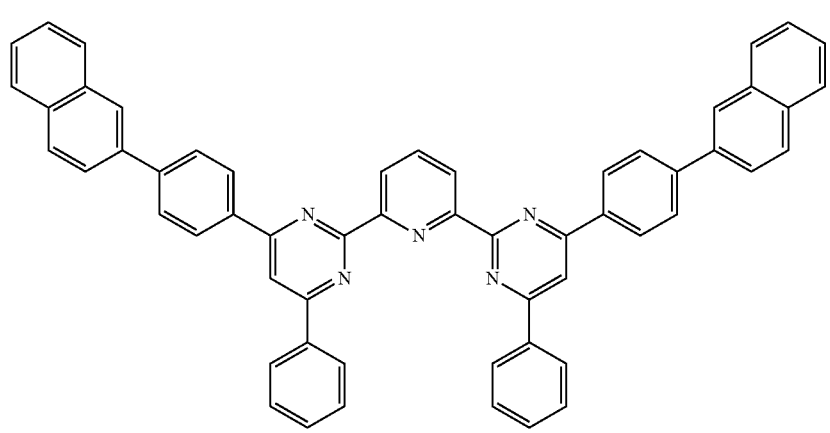
2,6(NP-PPm)2Py (Method for Manufacturing Light-Emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 functions as an anode of the light-emitting element.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to about $10^{-4}$ Pa. After that, over the first electrode 101, 9-phenyl-3-[4-(10-phenyl-9-anthryl)phenyl]-9H-carabzole (abbreviation: PCzPA) represented by the above structural formula (i) and molybdenum(VI) oxide were deposited by co-evaporation by an evaporation method using resistance heating, so that the hole-injection layer 111 was formed. The thickness of the hole-injection layer 111 was set to 50 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 10 nm over the hole-injection layer 111 to form the hole-transport layer 112.

Then, the electron-transport layer 114 was formed over the light-emitting layer 113 in such a manner that a 10 nm thick film of CzPA was formed and a 15 nm thick film of 2,6(N-PPm)2Py represented by the structural formula (100) was formed.

After the formation of the electron-transport layer 114, an electron-injection buffer layer was formed by evaporation of lithium oxide ($Li_2O$) to a thickness of 0.1 nm, and an electron-relay layer was formed by deposition of copper phenanthroline (abbreviation: CuPc) represented by the above structural formula (v) to a thickness of 2 nm. Then, a p-type layer was formed by co-evaporation of PCzPA and molybdenum oxide to a thickness of 20 nm. The weight ratio of PCzPA to molybdenum oxide was adjusted to 4:2. Note that the electron-injection buffer layer, the electron-relay layer, and the p-type layer may be collectively referred to as a charge-generation layer in some cases.

Lastly, aluminum was deposited by evaporation to a thickness of 200 nm to form the second electrode 102 functioning as a cathode. Thus, the light-emitting element 1 in this example was manufactured.

(Method for Manufacturing Light-Emitting Element 2)

The light-emitting element 2 was manufactured in the same manner as the light-emitting element 1 except for changing 2,6(N-PPm)2Py in the electron-transport layer of the light-emitting element 1 to 2,6(NP-PPm)2Py represented by the structural formula (200).

(Method for Manufacturing Comparative Light-Emitting Element 1)

The comparative light-emitting element 1 was manufactured in the same manner as the light-emitting element 1 except for changing 2,6(N-PPm)2Py in the electron-transport layer of the light-emitting element 1 to 2,6(P2Pm)2Py represented by the structural formula (v).

The element structures of the light-emitting elements 1 and 2 and the comparative light-emitting element 1 are shown in a table below.

TABLE 1

| Hole-injection layer | Hole-transport layer | Light-emitting layer | Electron-transport layer | | Electron-injection buffer layer | Electron-relay layer | p-Type layer |
|---|---|---|---|---|---|---|---|
| PCzPA:MoOx 4:2 | PCzPA | CzPA: 1,6mMem FLPAPrn 1:0.04 | CzPA | *1 | $Li_2O$ | CuPc | PCzPA:MoOx 4:2 |
| 50 nm | 10 nm | 25 nm | 10 nm | 15 nm | 0.1 nm | 2 nm | 20 nm |

*1 Light-emitting element 1: 2,6(N-PPm)2Py
Light-emitting element 2: 2,6(NP-PPm)2Py
Comparative light-emitting element 1: 2,6(P2Pm)2Py Furthermore, over the hole-transport layer 112, the light-emitting layer 113 was formed by co-evaporation of 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6 mMemFLPAPm) represented by the above structural formula (iii) with a weight ratio of 1:0.04 (=CzPA:1,6mMemFLPAPm) to a thickness of 25 nm.

The light-emitting elements 1 and 2 and the comparative light-emitting element 1 were each sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, reliability of these light-emitting elements was measured. Note that the measurements were carried out at room temperature (in an atmosphere kept at 25° C.).

Table 2 shows main characteristics of the light-emitting elements 1 and 2 and the comparative light-emitting element 1 at around 1000 cd/m².

TABLE 2

|  | Voltage (V) | Current (mA) | Current density (mA/cm²) | Chromaticity x | Chromaticity y | Current efficiency (cd/A) | External quantum efficiency (%) |
| --- | --- | --- | --- | --- | --- | --- | --- |
| Light-emitting element 1 | 3.7 | 0.72 | 18 | 0.14 | 0.18 | 5.9 | 4.7 |
| Light-emitting element 2 | 4.4 | 0.81 | 20 | 0.14 | 0.20 | 5.3 | 4.1 |
| Comparative light-emitting element 1 | 3.1 | 0.53 | 13 | 0.14 | 0.19 | 5.8 | 4.5 |

It can be found from Table 2 that each of the light-emitting elements is a blue light-emitting element with favorable characteristics.

Figure 19:
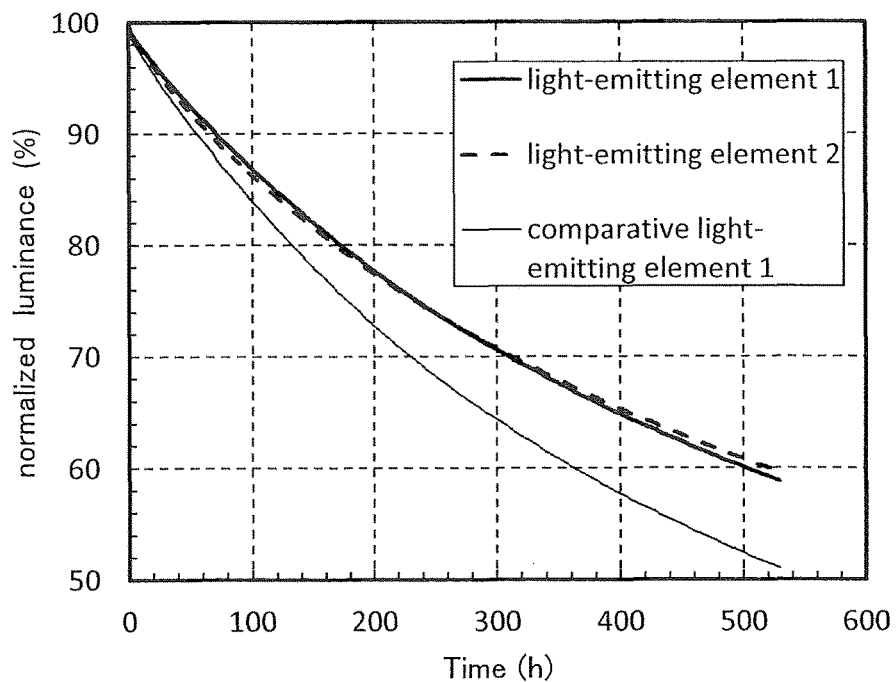
FIG. 19 shows time dependence of normalized luminance of a light-emitting element 1, a light-emitting element 2, and a comparative light-emitting element 1.

FIG. 19 shows changes in luminance of the light-emitting elements with driving time under the conditions where the initial luminance was 5000 cd/m² and the current density was constant. As shown in FIG. 19, the light-emitting elements 1 and 2, each of which is a light-emitting element of one embodiment of the present invention, clearly show higher reliability than the comparative light-emitting element 1. This means that a light-emitting element which includes a charge-generation layer and a layer containing the organic compound of one embodiment of the present invention in contact with the anode side of the charge-generation layer shows very high reliability. Although 2,6(P2Pm)2Py contained in the comparative light-emitting element 1 has a structure highly similar to those of 2,6(N-PPm)2Py and 2,6(NP-PPm)2Py contained in the light-emitting elements 1 and 2, the most important difference is the presence or absence of a naphthyl group that is an aryl group having 10 carbon atoms. Owing to the presence of this aryl group, the light-emitting elements 1 and 2 containing 2,6(N-PPm)2Py and 2,6(NP-PPm)2Py show high reliability.

In addition, 2,6(N-PPm)2Py and 2,6(NP-PPm)2Py have high heat resistance; thus, the light-emitting elements 1 and 2 have high heat resistance.

The charge-generation layer including the electron-injection buffer layer, the electron-relay layer, and the p-type layer provided in each of the light-emitting elements 1 and 2 has a structure similar to a charge-generation layer provided between light-emitting units in a tandem light-emitting element. That is, a tandem light-emitting element can also have a long lifetime like the light-emitting elements 1 and 2 when a layer in contact with the anode side of the charge-generation layer contains the organic compound of one embodiment of the present invention.

Example 5

In this example, a light-emitting element 3 containing 2,2'-(pyridine-2,6-diyl)bis{4-[4-(2-naphthyl)phenyl]-6-phenylpyrimidine} (abbreviation: 2,6(NP-PPm)2Py), which is represented by the structural formula (200) and is synthesized in Synthesis example 2, will be described. Structure formulae of organic compounds used in the light-emitting element 3 are shown below.

[Chemical Formulae 30]

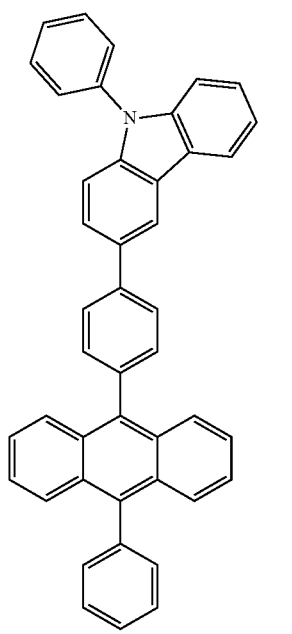

PCzPA

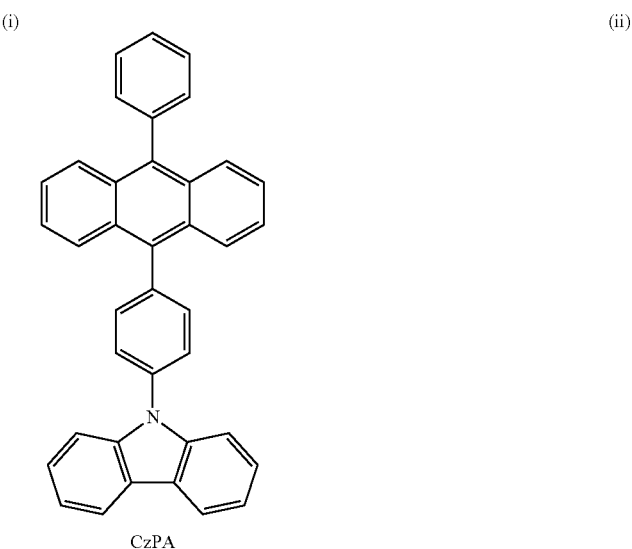

CzPA (iii)

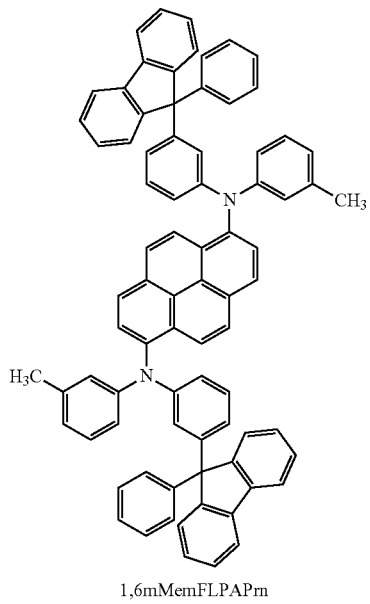

1,6mMemFLPAPrn (200)

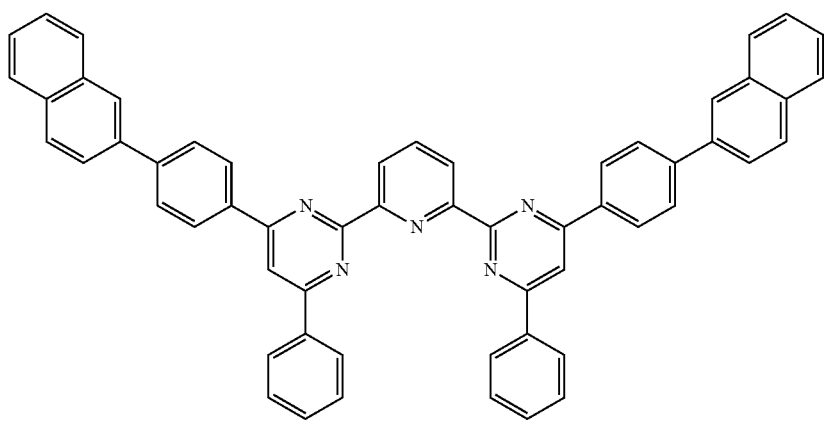

2,6(NP-PPm)2Py (iv)

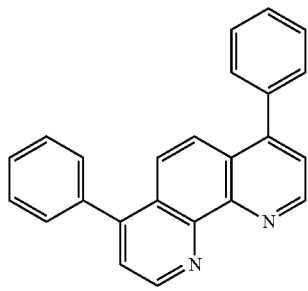

BPhen (Method for Manufacturing Light-Emitting Element 3)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 functions as an anode of the light-emitting element.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. The pressure in the vacuum evaporation apparatus was reduced to about $10^{-4}$ Pa. After that, over the first electrode 101, 9-phenyl-3-[4-(10-phenyl-9-anthryl)phenyl]-9H-carabzole (abbreviation: PCzPA) represented by the above structural formula (i) and molybdenum(VI) oxide were deposited by co-evaporation by an evaporation method using resistance heating, so that the hole-injection layer 111 was formed. The thickness of the hole-injection layer 111 was set to 50 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 10 nm over the hole-injection layer 111 to form the hole-transport layer 112.

Furthermore, over the hole-transport layer 112, the light-emitting layer 113 was formed by co-evaporation of 9-[4-(10-phenyl-9-anthryl)phenyl]-9H-carbazole (abbreviation: CzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPm) represented by the above structural formula (iii) with a weight ratio of 1:0.04 (=CzPA:1, 6mMemFLPAPrn) to a thickness of 25 nm.

Then, the electron-transport layer 114 was formed over the light-emitting layer 113 in such a manner that a 25 nm thick film of 2,6(NP-PPm)2Py represented by the structural formula (200) was formed.

After the formation of the electron-transport layer 114, an electron-injection buffer layer was formed by evaporation of lithium oxide ($Li_2O$) to a thickness of 0.1 nm, and an electron-relay layer was formed by deposition of copper phenanthroline (abbreviation: CuPc) represented by the above structural formula (v) to a thickness of 2 nm. Then, a p-type layer was formed by co-evaporation of PCzPA and molybdenum oxide to a thickness of 20 nm. The weight ratio of PCzPA to molybdenum oxide was adjusted to 4:2. Note that the electron-injection buffer layer, the electron-relay layer, and the p-type layer may be collectively referred to as a charge-generation layer in some cases.

Lastly, aluminum was deposited by evaporation to a thickness of 200 nm to form the second electrode 102 functioning as a cathode. Thus, the light-emitting element 3 in this example was manufactured.

The element structure of the light-emitting element 3 is shown in a table below.

The light-emitting element 3 was sealed using a glass substrate in a glove box containing a nitrogen atmosphere so as not to be exposed to the air (specifically, a sealing material was applied to surround the element and UV treatment and heat treatment at 80° C. for 1 hour were performed at the time of sealing). Then, reliability of these light-emitting elements was measured. Note that the measurements were carried out at room temperature (in an atmosphere kept at 25° C.).

Table 4 shows main characteristics of the light-emitting element 3 at around 1000 cd/m$^2$.

TABLE 4

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 3 | 4.4 | 0.72 | 18 | 0.14 | 0.19 | 5.5 | 4.2 |

It can be found from Table 4 that the light-emitting element 3 is a blue light-emitting element with favorable characteristics.

Figure 20:
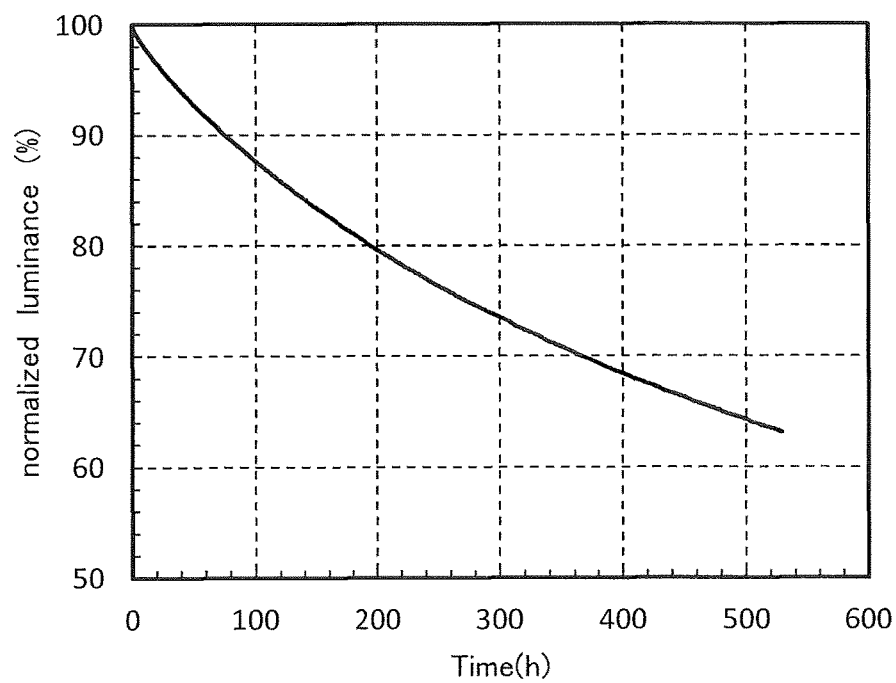
FIG. 20 shows time dependence of normalized luminance of a light-emitting element 3.

FIG. 20 shows a change in luminance of the light-emitting element with driving time under the conditions where the initial luminance was 5000 cd/m$^2$ and the current density was constant. As shown in FIG. 20, the light-emitting element 3, which is a light-emitting element of one embodiment of the present invention, shows very high reliability. This means that a light-emitting element which includes a charge-generation layer and a layer containing the organic compound of one embodiment the present invention in contact with the anode side of the charge-generation layer shows very high reliability.

In addition, 2,6(NP-PPm)2Py has high heat resistance; thus, the light-emitting element 3 has high heat resistance.

The charge-generation layer provided in the light-emitting element 3 has a structure similar to a charge-generation layer provided between light-emitting units in a tandem light-emitting element. That is, a tandem light-emitting element can have long lifetime like the light-emitting element 3 when a layer in contact with the anode side of the charge-generation layer contains the organic compound of one embodiment of the present invention.

This application is based on Japanese Patent Application serial no. 2014-265483 filed with Japan Patent Office on Dec. 26, 2014, the entire contents of which are hereby incorporated by reference.

TABLE 3

| Hole-injection layer | Hole-transport layer | Light-emitting layer | Electron-transport layer | Electron-injection buffer layer | Electron-relay layer | p-Type layer |
|---|---|---|---|---|---|---|
| PCzPA:MoOx 4:2 | PCzPA | CzPA: 1,6mMem FLPAPrn 1:0.04 | 2,6(NP-PPm) 2Py | $Li_2O$ | CuPc | PCzPA:MoOx 4:2 |
| 50 nm | 10 nm | 25 nm | 25 nm | 0.1 nm | 2 nm | 20 nm |

What is claimed is:

1. An organic compound represented by a general formula (G1):

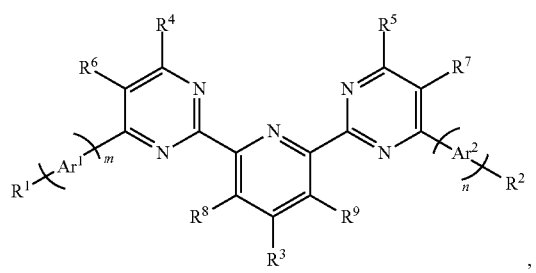

wherein Ar¹ and Ar² represent a phenylene group, and n and m separately represent 0 or 1, wherein $R^1$ to $R^3$ separately represent hydrogen or an aryl group having 6 to 16 carbon atoms, at least one of $R^1$ to $R^3$ being an aryl group with a fused structure having 10 to 16 carbon atoms, and wherein $R^4$ to $R^9$ separately represent hydrogen, an alkyl group having 1 to 6 carbon atoms, or an aryl group having 6 to 10 carbon atoms.

2. The organic compound according to claim 1, wherein $R^1$ and $R^2$ are each a naphthyl group.

3. The organic compound according to claim 1, wherein n and m are 0, and wherein $R^3$ is a pyrenyl group.

4. The organic compound according to claim 1, wherein $R^3$ is hydrogen.

5. The organic compound according to claim 1, wherein $R^4$ and $R^5$ are each a phenyl group.

6. The organic compound according to claim 1, wherein $R^6$ to $R^9$ are each hydrogen.

7. The organic compound according to claim 1, wherein the organic compound is represented by any one of structural formulae (100), (200), and (300):

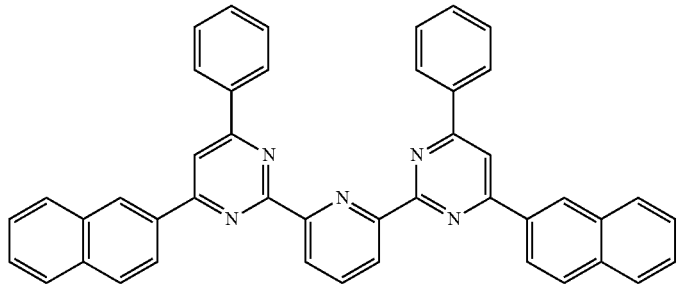

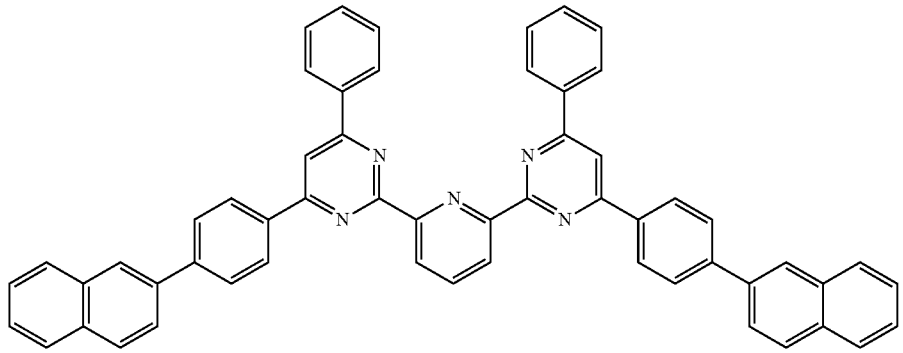

-continued

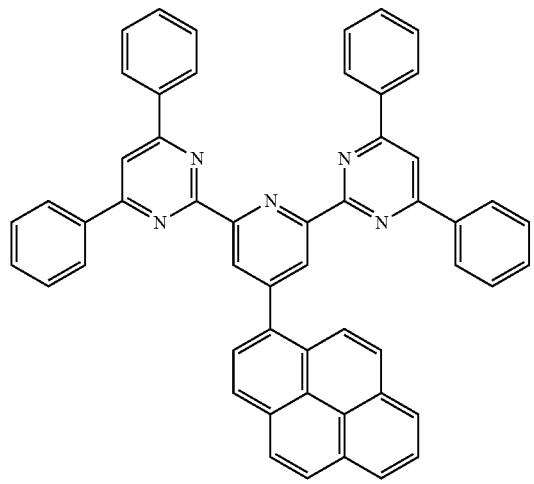
(300)

8. A light-emitting element comprising:
a first electrode;
a layer over the first electrode; and
a second electrode over the layer,
wherein the layer comprises an organic compound represented by a general formula (G1):

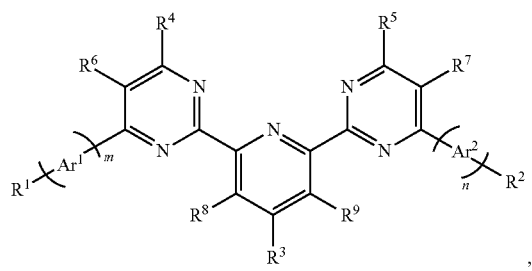
(G1)

wherein $Ar^1$ and $Ar^2$ represent a phenylene group, and n and m separately represent 0 or 1, wherein $R^1$ to $R^3$ separately represent hydrogen or an aryl group having 6 to 16 carbon atoms, at least one of $R^1$ to $R^3$ being an aryl group with a fused structure having 10 to 16 carbon atoms, and wherein $R^4$ to $R^9$ separately represent hydrogen, an alkyl group having 1 to 6 carbon atoms, or an aryl group having 6 to 10 carbon atoms.

9. The light-emitting element according to claim 8, wherein $R^1$ and $R^2$ are each a naphthyl group.

10. The light-emitting element according to claim 8, wherein n and m are 0, and
wherein $R^3$ is a pyrenyl group.

11. The light-emitting element according to claim 8, wherein $R^3$ is hydrogen.

12. The light-emitting element according to claim 8, wherein $R^4$ and $R^5$ are each a phenyl group.

13. The light-emitting element according to claim 8, wherein $R^6$ to $R^9$ are each hydrogen.

14. The light-emitting element according to claim 8, wherein the organic compound is represented by any one of structural formulae (100), (200), and (300):

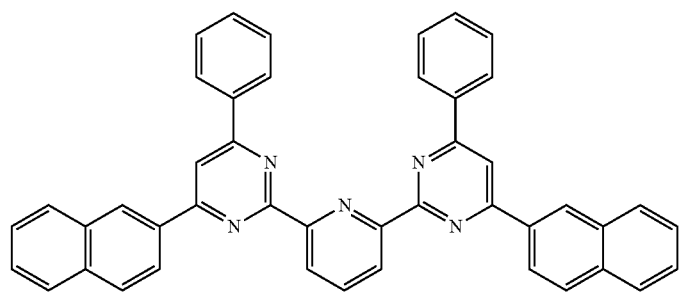
(100)

-continued

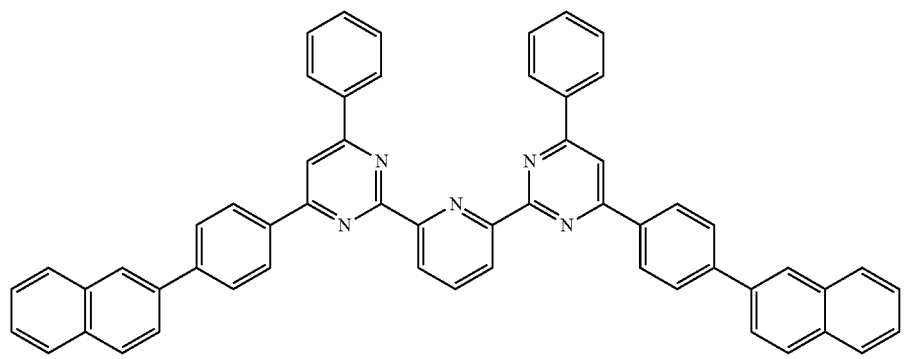
(200)

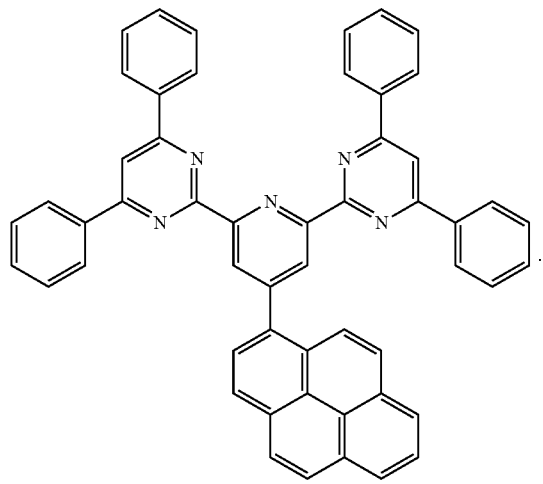
(300)

15. The light-emitting element according to claim 8, wherein the organic compound is in an electron-transport layer.

16. The light-emitting element according to claim 8, wherein the organic compound is in an electron-injection layer.

17. A light-emitting device comprising:

the light-emitting element according to claim 8; and
a unit for controlling the light-emitting element.

* * * * *

UNITED STATES PATENT AND TRADEMARK OFFICE
CERTIFICATE OF CORRECTION

PATENT NO. : 9,929,352 B2
APPLICATION NO. : 14/976443
DATED : March 27, 2018
INVENTOR(S) : Hideko Inoue et al.

Page 1 of 1

It is certified that error appears in the above-identified patent and that said Letters Patent is hereby corrected as shown below:

In the Claims

-- Claim 3, Column 74, Line 11: delete "in" and insert -- m --.

Signed and Sealed this
Tenth Day of July, 2018

Andrei Iancu
*Director of the United States Patent and Trademark Office*